(12) United States Patent
Viola et al.

(10) Patent No.: US 11,672,877 B2
(45) Date of Patent: Jun. 13, 2023

(54) IN VIVO IMMUNOIMAGING OF INTERFERON-GAMMA

(71) Applicant: Wayne State University, Detroit, MI (US)

(72) Inventors: Nerissa Viola, Canton, MI (US); Heather Gibson, Ferndale, MI (US)

(73) Assignee: Wayne State University, Detroit, MI (US)

( * ) Notice: Subject to any disclaimer, the term of this patent is extended or adjusted under 35 U.S.C. 154(b) by 361 days.

(21) Appl. No.: 16/640,456

(22) PCT Filed: Aug. 23, 2018

(86) PCT No.: PCT/US2018/047742
§ 371 (c)(1),
(2) Date: Feb. 20, 2020

(87) PCT Pub. No.: WO2019/040740
PCT Pub. Date: Feb. 28, 2019

(65) Prior Publication Data
US 2020/0206371 A1 Jul. 2, 2020

Related U.S. Application Data

(60) Provisional application No. 62/549,231, filed on Aug. 23, 2017.

(51) Int. Cl.
*A61K 51/10* (2006.01)
*C07K 16/24* (2006.01)

(52) U.S. Cl.
CPC ...... *A61K 51/1021* (2013.01); *A61K 51/1093* (2013.01); *C07K 16/249* (2013.01)

(58) Field of Classification Search
None
See application file for complete search history.

(56) References Cited

U.S. PATENT DOCUMENTS

| 5,720,937 A | 2/1998 | Hudziak et al. |
|---|---|---|
| 9,682,142 B2 | 6/2017 | Ferlin et al. |
| 2014/0186362 A1* | 7/2014 | Ferlin ...................... A61P 1/04 424/142.1 |

(Continued)

OTHER PUBLICATIONS

Gibson, H. et al., IFNγ PET Imaging as a Predictive Tool for Monitoring Response to Tumor Immunotherapy, Cancer Research, 78(19): 5706-5717, Aug. 16, 2018.

(Continued)

*Primary Examiner* — Jennifer Lamberski
(74) *Attorney, Agent, or Firm* — Julie K. Staple; Dinsmore & Shohl LLP

(57) ABSTRACT

Methods for in vivo immunoimaging including: (a) administering a labeled-antibody conjugate to a subject, wherein the labeled-antibody conjugate includes: an antibody that specifically recognizes and binds to IFN-γ, and a detection label conjugated to the antibody, wherein the detection label is a radionuclide tracer or fluorophore; and (b) detecting the presence of the radiolabeled-antibody conjugate in the subject in vivo by imaging. Embodiments of the present disclosure are directed to labeled-antibody conjugates and therapeutic radionuclide-antibody conjugates.

11 Claims, 32 Drawing Sheets

Specification includes a Sequence Listing.

(56) References Cited

U.S. PATENT DOCUMENTS

2016/0199524 A1* 7/2016 Hernandez ......... C07K 16/3007
424/1.49

OTHER PUBLICATIONS

Herda, S. et al., The Sorting Receptor Sortilin Exhibits a Dual Function in Exocytic Trafficking of Interferon-γ and Granzyme A in T Cells, Immunity, 37(5): 854 866, Oct. 18, 2012.
Stybayeva, G. et al., Lensfree Holographic Imaging of Antibody Microarrays for High-Throughput Detection of Leukocyte Numbers and Function, Analytical Chemistry, 82(9): 3736-3744, May 1, 2010.
Arlauckas, S. et al., In vivo imaging reveals a tumor-associated macrophage-mediated resistance pathway in anti-PD-1 therapy, Science Translational Medicine, 9(389): eaal3604 (pp. 1-10), May 10, 2017.
Stanton, S. et al., Concurrent SPECT/PET-CT imaging as a method for tracking adoptively transferred T-cells in vivo, Journal for ImmunoTherapy of Cancer, 4:27, 5 pages, May 17, 2016.
Ghanekar, S. et al., Gamma Interferon Expression in CD8+ T Cells is a Marker for Circulating Cytotoxic T Lymphocytes That Recognize an HLA A2-Restricted Epitope of Human Cytomegalovirus Phosphoprotein pp65, Clinical and Diagnostic Laboratory Immunology, 8(3): 628-631, May 2001.

* cited by examiner

IN VIVO IMMUNOIMAGING OF INTERFERON-GAMMA

REFERENCE TO RELATED APPLICATION

This application claims priority from U.S. Provisional Patent Application Ser. No. 62/549,231, filed Aug. 23, 2017, the entire content of which is incorporated herein by reference.

SEQUENCE LISTING

The instant application contains a Sequence Listing which has been submitted electronically as a file in ASCII format and is hereby incorporated by reference in its entirety. Said ASCII format file, created on Aug. 23, 2018, is named 47WAY13152WO_ST25.txt and is 19,923 bytes in size.

FIELD OF THE INVENTION

The present disclosure generally relates to antibody conjugates, to methods for imaging antibody conjugates in vivo, methods and compositions relating to antibody conjugates, and to methods for assessing an effect of a composition or immune-mediated treatment for cancer, injury, or infection. The present disclosure specifically relates to antibody conjugates which specifically recognize interferon gamma (IFN-γ), to methods for imaging IFN-γ antibody conjugates in vivo, methods and compositions relating to IFN-γ antibody conjugates, and to methods for assessing an effect of a composition or immune-mediated treatment for cancer, injury, or infection.

BACKGROUND OF THE INVENTION

During adaptive cancer immunotherapy activated T cells infiltrating a tumor are the principal components of treatment providing a "search-and-destroy" mechanism through recognition of specific tumor-associated antigens (TAA). Recent emerging tumor-targeted immunotherapy strategies have met with positive and durable outcomes in the clinic, and yet at least half of cancer patients remain non-responsive thereby creating urgency to monitor and gauge an immunotherapy's success in a timely manner. The primary focus of these efforts lies in techniques to measure peripheral immune responses. These assays are typically restricted to one antigen, are non-standardized and may not reflect dynamic activity occurring within a tumor. There is an ongoing need for antibody conjugates that identify the presence of activated tumor-infiltrating T cells in vivo and methods of use thereof. Image-guided focal analysis of intratumoral immune activity according to aspects of the present invention, provides non-invasive, real-time efficacy predictions to aid in assessment of the effectiveness of an immunotherapy.

SUMMARY OF THE INVENTION

In particular, the disclosure demonstrates that the in vivo immunoimaging of interferon gamma (IFN-γ) identifies active T cells, such as activated tumor-infiltrating T cells, in vivo relative to agents that recognize other biomarkers.

Embodiments of the present disclosure are directed to methods of in vivo immunoimaging IFN-γ as a marker of activate T cells in a subject including: (a) administering a labeled-antibody conjugate to a subject, wherein the labeled-antibody conjugate includes: an antibody that specifically recognizes IFN-γ, and at least one detection label conjugated to the antibody, wherein the at least one detection label is a radionuclide; and (b) detecting the presence of the labeled-antibody conjugate in the subject in vivo by imaging.

Embodiments of the present disclosure are directed to labeled-antibody conjugates including: an antibody that specifically recognizes and binds to IFN-γ, and at least one detection label conjugated to the antibody, wherein the at least one detection label is a radionuclide tracer.

Embodiments of the present disclosure are directed to therapeutic radionuclide-antibody conjugates including: 1) an antibody that specifically recognizes and binds to IFN-γ, a bifunctional chelator conjugated to the antibody, and a radionuclide therapeutic agent complexed to the bifunctional chelator or 2) an antibody that specifically recognizes and binds to IFN-γ, a linker conjugated to the antibody, and a radionuclide therapeutic agent conjugated to the antibody via the linker.

It is to be understood that both the foregoing general description and the following detailed description describe various embodiments and are intended to provide an overview or framework for understanding the nature and character of the claimed subject matter. The accompanying drawings are included to provide a further understanding of the various embodiments and are incorporated into and constitute a part of this specification. The drawings illustrate the various embodiments described herein, and together with the description, serve to explain the principles and operations of the claimed subject matter.

DETAILED DESCRIPTION OF THE INVENTION

Figure 1A:
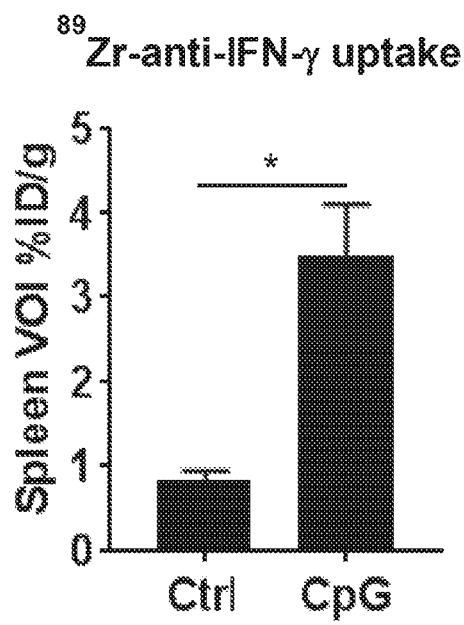
FIG. 1A is a graph showing that BALB/c mice treated with CpG-ODN and imaged with the $^{89}$Zr-anti-IFN-γ labeled-antibody conjugate 72 h post-injection (p.i.) displayed higher uptake in the spleen compared to control (Ctrl) untreated cohorts (n=3 each)

While the following terms are believed to be well understood by one of ordinary skill in the art, definitions are set forth to facilitate explanation of the presently-disclosed subject matter.

The term "label" refers to a chemical moiety that can be covalently attached to an antibody and that functions to provide a detectable signal, such as, e.g., radionuclide tracers.

The term "antibody" is used herein in its broadest sense and specifically refers to monoclonal antibodies, polyclonal antibodies, dimers, multimers, multispecific antibodies (e.g., bispecific antibodies), and antibody fragments, so long as they exhibit the desired biological activity (see e.g., Miller et al. (2003) J Immunology 170:4854-4861). Antibodies may be murine, human, humanized, chimeric, or derived from other species. An antibody is a protein that is capable of recognizing and binding to a specific antigen, such as, e.g., IFN-γ. (See e.g., Janeway, C., Travers, P., Walport, M., Shlomchik (2001) Immuno Biology, 5th Ed., Garland Publishing, New York). A target antigen may have numerous binding sites, also called epitopes, recognized by complementarity determining regions of antibodies. In embodiments, each antibody that specifically binds to a different epitope has a different structure. Thus, one antigen may have more than one corresponding antibody. An antibody includes a full-length immunoglobulin molecule or an immunologically-active portion of a full-length immunoglobulin molecule, such as, e.g., a molecule that contains an antigen binding site that immunospecifically recognizes and binds to an antigen of a target of interest or part thereof, such as, e.g., IFN-γ. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In some embodiments, however, the immunoglobulin is of rodent or human origin. According to embodiments, the antibody is an antibody fragment and in specific embodiments, the antibody fragment is a diabody.

The term "specifically recognizes and binds to" refers to antibodies that are capable of binding to an antigen of interest, such as, e.g., IFN-γ, with sufficient binding affinity such that the antibody is useful in targeting the antigen of interest. As an example, the antibodies may have a binding affinity $K_D$ of from about $10^{-4}$ to about $10^{-15}$, or from about $10^{-6}$ to about $10^{-13}$, or from about $10^{-7}$ to about $10^{-12}$, or from about $10^{-9}$ to about $10^{-10}$, for the antigen of interest. As another example, where the antibody is one that binds to IFN-γ, it will preferentially bind to IFN-γ as opposed to other antigens and/or extracellular components. As a further example, where the antibody is one that binds to IFN-γ, it may not significantly cross-react with other extracellular components. In embodiments, the extent of binding of the antibody to non-IFN-γ antigens and/or other extracellular components is less than about 10% (such as, e.g., 0% to about 9%), as determined by standard techniques known to those of ordinary skill in the art, such as, e.g., by flow cytometric analysis.

The terms "interferon gamma" and "IFN-γ" are synonyms that refer to a cytokine. IFN-γ is a member of the interferon family, which exhibits similar antiviral and anti-proliferative properties characteristic of interferons-α and -β (IFN-α and IFN-β). IFN-γ was originally discovered as a product induced upon mitogenic activation of lymphocytes. The recombinant production of human IFN-γ was first reported by Gray, Goeddel and co-workers (Gray et al., Nature 295:503-508, 1982), and is subject of U.S. Pat. Nos. 4,762,791, 4,929,544, 4,727,138, 4,925,793, 4,855,238, 5,582,824, 5,096,705, 5,574,137, and 5,595,888, each of which is hereby incorporated by reference in its entirety. The recombinant human IFN-γ of Gray and Goeddel as produced in *E. coli* consisted of 146 amino acids, the N-terminal position of the molecule commencing with the sequence CysTyrCys. It was later found that the native human IFN-γ (i.e., that arising from mitogen induction of human peripheral blood lymphocytes and subsequent purification) is a polypeptide that lacks the CysTyrCys N-terminus assigned by Gray et al., supra. The crystal structure of *E. coli*-derived recombinant human IFN-γ (rhIFN-γ) was determined (Ealick et al., Science 252:698-702, 1991), showing that the protein exists as a tightly intertwined non-covalent homodimer, in which the two identical polypeptide chains are oriented in an antiparallel manner. IFN-γ is known to exhibit a broad range of biological activities, including antitumor, antimicrobial and immunoregulatory activities. A particular form of recombinant human IFN-γ is commercially available as an immunomodulatory drug for the treatment of chronic granulomatous disease characterized by severe, recurrent infections of the skin, lymph nodes, liver, lungs, and bones due to phagocyte dysfunction (rhIFN-γ-1b, Actimmune®, Genentech, Inc. South San Francisco, Calif.). IFN-γ was subsequently approved for use in patients with severe, malignant osteopetrosis. IFN-γ may refer to IFN-γ of any species including both human and mouse IFN-7.

The term "bifunctional chelator" refers to a chemical moiety that attaches an antibody to a radionuclide. Bifunctional chelators may include a chelator covalently attached to a first linking group. Bifunctional chelators may function by complexing metal ions with the chelator and by covalently attaching the chelator to an antibody with the first linking group, as is known to those of ordinary skill in the art. For example, bifunctional chelators may be covalently attached to a primary amine group, a hydroxyl group, and/or a cysteine amino acid of an antibody. Examples of suitable chelators include: 1,4,7-triazacyclononane-N,N',N'-triacetic acid (i.e., NOTA), 1,4,7,10-tetraazacyclododecane-1,4,7,10-tetraacetic acid (i.e., DOTA), ethylenediaminetetraacetic acid (i.e., EDTA), diethylenetriaminepentaacetic acid (i.e., DTPA; CAS Reg. No. 67-43-6), 1,4,7,10-tetraazacyclododecane-1,4,7,10-tetraacetic acid (i.e., DOPA), N'-{5-[Acetyl (hydroxy)amino]pentyl}-N-[5-({4-[(5-aminopentyl)(hydroxy)amino]-4-oxobutanoyl}amino)pentyl]-N-hydroxysuccinamide (i.e., deferoxamine or DFO; CAS Reg. No. 70-51-9), 2,2'-(7-(1-carboxy-4-((2,5-dioxopyrrolidin-1-yl)oxy)-4-oxobutyl)-1,4,7-triazonane-1,4-diyl)diacetic acid (NODA), or a combination of any two or more thereof. Examples of suitable linking groups capable of attaching a chelator to a primary amine group, a hydroxyl group, and/or a cysteine amino acid of an antibody are known to those of skill in the art (see e.g., Denardo et al., 1998, Clin Cancer Res. 4(10):2483-90; Peterson et al., 1999, Bioconjug. Chem. 10(4):553-7; and Zimmerman et al., 1999, Nucl. Med. Biol. 26(8):943-50). Examples of suitable bifunctional chelators include 4-maleimidobutyramidobenzyl-DOTA (which can be prepared following the procedure of Axworthy et al (2000) Proc. Natl. Acad. Sci. USA 97(4):1802-1807), 1-isothiocyanatobenzyl-3-methyldiethylene triaminepentaacetic acid (i.e., MX-DTPA, see e.g., International Pub. No. WO 94/11026), p-SCN-Bn-Deferoxamine (i.e., p-SCN-Bn-DFO), or a combination of any two or more thereof (See also, US Patent Application Publication No. 2015/0017094, hereby incorporated by reference in its entirety). p-SCN-Bn-DFO has the following structure:

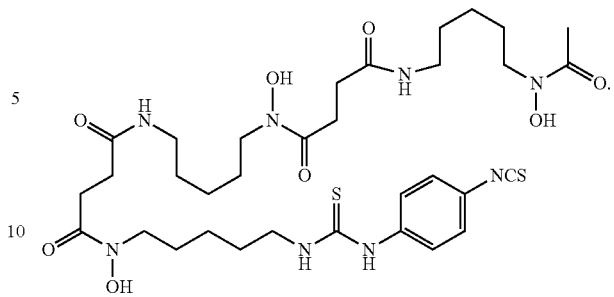

With regard to antibodies, the term "isolated" refers to an antibody that has been identified and separated and/or recovered from at least one contaminant component of its natural environment. Contaminant components may be materials that would interfere with diagnostic and/or therapeutic uses for the antibody, such as, e.g., enzymes, hormones, and/or other proteinaceous or nonproteinaceous solutes. In embodiments, the isolated antibody will be purified to greater than about 95% (such as, e.g., about 96% to about 100%) by weight of antibody as determined by the Lowry method, or to greater than about 99% by weight of antibody.

The term "monoclonal antibody" refers to an antibody obtained from a population of substantially homogeneous antibodies, wherein the individual antibodies in the population are identical except for naturally occurring post-translational modifications. Monoclonal antibodies may be highly specific, being directed against a single antigenic site. Furthermore, in contrast to polyclonal antibody preparations that include different antibodies directed against different antigenic determinants (such as, e.g., epitopes), each monoclonal antibody is directed against a single antigenic determinant on the antigen. Monoclonal antibodies may be synthesized uncontaminated by other antibodies. While monoclonal indicates the character of the antibody as being obtained from a substantially homogeneous population of antibodies, it is not intended to be construed as requiring production of the antibody by any particular method. For example, the monoclonal antibodies to be used in accordance with the present disclosure may be prepared by the Kohler hybridoma method (see e.g., Kohler et al. (1975) Nature 256:495), or they may be prepared by recombinant DNA methods (see e.g., U.S. Pat. Nos. 4,816,567 and 5,807,715, each of which is hereby incorporated by reference in its entirety). Further, monoclonal antibodies may be isolated from phage antibody libraries using standard techniques (see e.g., Clackson et al. (1991) Nature, 352:624-628 and Marks et al. (1991) J. Mol. Biol., 222:581-597).

The terms "antibody fragment" and "fragment" refer to a portion of a full length antibody that includes a region capable of recognizing and binding to a specific antigen, such as, e.g., the antigen binding, variable, or hypervariable (also known as complementarity determining) region thereof. Examples of antibody fragments include Fab, Fab', F(ab')₂, F(ab)₂, Fv, sFv, and scFv fragments; diabodies; linear antibodies; minibodies (see e.g., Olafsen et al. (2004) Protein Eng. Design & Sel. 17(4):315-323), fragments produced by a Fab expression library, anti-idiotypic (hereinafter, "anti-Id") antibodies, complementary determining region (hereinafter, "CDR") and epitope-binding fragments of any of the above that immunospecifically recognize and bind to IFN-γ, single-chain antibody molecules, and multispecific antibodies formed from antibody fragments.

The term "radiolabel" refers to a radionuclide moiety that can be attached to an antibody and that functions to provide a detectable signal, such as, e.g., radionuclide tracers. Radionuclide tracers include radioisotopes, which by virtue of radioactive decay, are detectable. Radionuclide tracers may be detected by various imaging techniques, such as, e.g., PET and single-photon emission computed tomography (hereinafter, "SPECT") imaging. In embodiments, radionuclide tracers have an energy of from about 20 to about 4,000 kiloelectronvolts (i.e., keV). Suitable radionuclide tracers include radionuclides that emit gamma radiation, positrons, or a combination of gamma radiation and positrons. In illustrative, non-limiting embodiments, radionuclide tracers have appropriate decay characteristics for optimizing image resolution and quantitative accuracy and/or have appropriate residualization. For example, radionuclide tracers may have a physical half-life (i.e., $t_{1/2}$) compatible with the time required for the antibody to achieve optimal specific:nonspecific binding ratios. Examples of radionuclide tracers suitable for PET imaging include $^{11}C$ ($t_{1/2}\sim$ 20 min), $^{13}N$ ($t_{1/2}\sim$ 10 min), $^{15}O$ ($t_{1/2-2}$ min), $^{18}F$ ($t_{1/2}\sim$ 1.83 h), $^{44}Sc$ ($t_{1/2-3.97}$ h), $^{45}Ti$ ($t_{1/2-3}$ h), $^{52}Mn$ ($t_{1/2-5.6}$ days), $^{64}Cu$ ($t_{1/2-12.7}$ h), $^{68}Ga$ ($t_{1/2}\sim$ 1.13 h), $^{76}Br$ ($t_{1/2}\sim$ 16.2 h), $^{82}Rb$ ($t_{1/2}\sim$ 1.27 min), $^{86}Y$ ($t_{1/2-14.7}$ h), $^{89}Zr$ ($t_{1/2-78.4}$ h), $^{124}I$ ($t_{1/2-\ 100.3}$ h), or a combination of any two or more thereof. Examples of radionuclide tracers suitable for SPECT imaging include $^{99m}Tc$ ($t_{1/2-6}$ h), $^{113m}In$ ($t_{1/2-2.80}$ days), $^{131}I$ ($t_{1/2-8}$ days), $^{177}Lu$ ($t_{1/2}\sim$ 6.64 days), $^{186}Re$ ($t_{1/2}\sim$ 3.7186 days), or a combination of any two or more thereof.

The term "therapeutic radionuclide" refers to a radionuclide moiety that can be attached to an antibody that functions to deliver a cytotoxic dose of radiation, such as, e.g., a radionuclide therapeutic agent, to a target of interest, such as, e.g., a tumor. Suitable radionuclide therapeutic agents include radionuclides that emit beta particle radiation, alpha particle radiation, Auger electron radiation, or a combination of any two or more thereof. Examples of suitable radionuclide therapeutic agents include $^{125}I$, $^{131}I$, $^{177}Lu$, $^{186}Re$, $^{225}Ac$, $^{225}Ra$, or a combination of any two or more thereof.

The term "immunoimaging" refers to imaging IFN-γ in vivo in a subject via detection of a labeled anti-IFN-γ antibody conjugate to produce an image indicative of the location and/or level of IFN-γ in the subject, wherein the location and/or level of IFN-γ in the subject is indicative of activated T cells.

Embodiments of the present disclosure are directed toward antibody conjugates, including labeled-antibody conjugates and therapeutic radionuclide-antibody conjugates, to methods for imaging, to mouse models, and to methods for assessing the effect of a composition or immune-mediated treatment for cancer, injury or infection, particularly human cancer, human injury or human infection.

I. Antibody Conjugates

In one or more embodiments, the disclosure relates to antibody conjugates. In embodiments, antibody conjugates include both labeled-antibody conjugates and therapeutic radionuclide-antibody conjugates. In embodiments, labeled-antibody conjugates include an antibody that specifically recognizes and binds to IFN-γ, and at least one detection label conjugated to the antibody, wherein the at least one detection label includes a radionuclide tracer.

Suitable antibodies that specifically recognize and bind to IFN-γ may be prepared by standard techniques known to those of ordinary skill in the art. In embodiments, the antibody is an isolated antibody. In embodiments, the antibody is selected from a monoclonal antibody, an antibody fragment, or combination thereof. In embodiments, the antibody is a monoclonal antibody expressed by a hybridoma cell line or by CHO cells, NS0 cells, Sp2/0 cells, HEK cells, BHK cells, or PER.C6 cells.

In embodiments, the antibody is an antibody fragment. In further embodiments, the antibody is a Fab fragment. Antibody fragments that recognize specific epitopes can be produced by standard techniques known to those of ordinary skill in the art. For example, F(ab')$_2$ fragments can be produced by pepsin digestion of the antibody molecule. (See e.g., U.S. Pat. Nos. 4,036,945 and 4,331,647 and references contained therein; see also Nisonoff et al., Arch Biochem. Biophys. 89:230 (1960); Porter, Biochem. J. 73:119 (1959), Edelman et al., in Methods in Enzymology Vol. 1, page 422 (Academic Press 1967), and Coligan et al. Current Protocols in Immunology, Vol. 1, pages 2.8.1-2.8.10 and 2.10.-2.10.4 (John Wiley & Sons 1991)). Alternatively, Fab' expression libraries can be constructed (see e.g., Huse et al., 1989, Science, 246:1274-1281) to allow rapid and easy identification of monoclonal Fab' fragments with desired specificity.

In embodiments, a single chain Fv molecule (i.e., scFv) includes a $V_L$ domain and a $V_H$ domain. The $V_L$ and $V_H$ domains may associate to form a target binding site. In embodiments, $V_L$ and $V_H$ domains are covalently linked by a peptide linker (i.e., L). In embodiments, a scFv molecule is denoted as either $V_L$-L-$V_H$ if the $V_L$ domain is the N-terminal part of the scFv molecule, or as $V_H$-L-$V_L$ if the $V_H$ domain is the N-terminal part of the scFv molecule. scFv molecules can be produced by standard techniques known to those of ordinary skill in the art. (See U.S. Pat. Nos. 4,704,692, 4,946,778, R. Raag and M. Whitlow, "Single Chain Fvs." FASEB Vol 9:73-80 (1995) and R. E. Bird and B. W. Walker, Single Chain Antibody Variable Regions, TIBTECH, Vol 9:132-137 (1991)).

Other antibody fragments, such as, e.g., single domain antibody fragments, are also known to those of ordinary skill in the art. Single domain antibodies (i.e., VHH) may be obtained, for example, from camels, alpacas or llamas by standard immunization techniques known to those of ordinary skill in the art. (See, e.g., Muyldermans et al., TIBS 26:230-235, 2001; Yau et al., J Immunol Methods 281:161-75, 2003; Maass et al., J Immunol Methods 324:13-25, 2007). In embodiments, the VHH has potent antigen-binding capacity and can interact with novel epitopes that may be inaccessible to conventional $V_H$-$V_L$ pairs. (See e.g., Muyldermans et al., 2001). In embodiments, alpaca serum IgG contains about 50% camel heavy chain only IgG antibodies (i.e., HCAbs) (see e.g., Maass et al., 2007). In embodiments, alpacas may be immunized with known antigens, such as, e.g., TNF-α, and VHH's can be isolated that bind to and neutralize the target antigen (see e.g., Maass et al., 2007). PCR primers that amplify virtually all alpaca VHH coding sequences have been identified and may be used to construct alpaca VHH phage display libraries, which can be used for antibody fragment isolation by standard biopanning techniques well known to those of ordinary skill in the art. (See Maass et al., 2007).

In embodiments, an antibody fragment is produced by proteolytic hydrolysis of a full-length antibody and/or by expression in E. coli, CHO cells, or another host of DNA coding for the antibody fragment. In embodiments, antibody fragments can be obtained by pepsin or papain digestion of full-length antibodies by standard techniques known to those of ordinary skill in the art. For example, an antibody fragment can be produced by enzymatic cleavage of antibodies with pepsin to provide an ~100 kDa fragment denoted F(ab')$_2$. This fragment can be further cleaved using a thiol reducing agent, and optionally a blocking group for the sulfhydryl groups resulting from cleavage of disulfide linkages, to produce a ~50 kDa Fab' monovalent fragment. In alternative embodiments, an enzymatic cleavage using papain produces two monovalent Fab fragments and an Fc fragment directly.

In embodiments, antibody fragments may include peptides coding for a single complementary determining region (i.e., CDR). In embodiments, a CDR is a segment of the variable region of an antibody that is complementary in structure to the epitope to which the antibody binds and is more variable than the rest of the variable region. Accordingly, in embodiments, a CDR is referred to as a hypervariable region. In embodiments, a variable region includes three CDRs. In embodiments, CDR peptides can be produced by constructing genes encoding the CDR of an antibody of interest. Such genes may be prepared, for example, by using the polymerase chain reaction (i.e., PCR) to synthesize the variable region from RNA of antibody-producing cells. (See e.g., Larrick et al., Methods: A Companion to Methods in Enzymology 2:106 (1991); Courtenay-Luck, "Genetic Manipulation of Monoclonal Antibodies," in Monoclonal Antibodies: Production, Engineering and Clinical Application, Ritter et al. (eds), pages 166-179 (Cambridge University Press 1995); and Ward et al., "Genetic Manipulation and Expression of Antibodies," in Monoclonal Antibodies: Principles and Applications, Birch et al., (eds.), pages 137-185 (Wiley-Liss, Inc. 1995).

According to embodiments, the antibody conjugate is an anti-IFN-γ diabody that specifically recognizes and binds to IFN-γ. A diabody included in a labeled-antibody conjugate is a noncovalent dimer of single-chain Fv (scFv) fragment that has the heavy chain variable ($V_H$) and light chain variable ($V_L$) regions connected by a linker, such as a peptide linker. According to embodiments, the diabody includes heavy chain variable region ($V_H$) having the amino acid sequence disclosed herein as SEQ ID NO:11 and light chain variable region ($V_L$) having the amino acid sequence disclosed herein as SEQ ID NO:12. The linker used is too short to allow pairing between the two domains on the same chain, such that the linked $V_H$-$V_L$ domains are forced to pair with complementary domains of another chain, creating two antigen-binding sites. Diabodies are described more fully in, for example, EP 404,097; WO 93/11161; and Hollinger et al., Proc. Natl. Acad. Sci. USA, 90: 6444-6448 (1993). An exemplary linker is SGGGGS (SEQ ID NO:13). According to embodiments, an scFv included in an anti-IFN-γ diabody that specifically recognizes and binds to IFN-γ has SEQ ID NO:14. According to embodiments, an scFv included in an anti-IFN-γ diabody that specifically recognizes and binds to IFN-γ has SEQ ID NO:15.

Variants of the scFv of SEQ ID NO:14 and/or SEQ ID NO:15 can also be included in an anti-IFN-γ diabody in labeled-antibody conjugate according to embodiments.

A functional variant of the scFv of SEQ ID NO:14 has at least about 85%, 90%, 91%, 92%, 93%, 94%, 95%, 96%, 97%, 98%, 99%, or greater, sequence identity with the amino acid sequence set forth in SEQ ID NO:14 wherein the diabody including the variant or variants specifically recognizes and binds to IFN-γ.

A functional variant of the scFv of SEQ ID NO:15 has at least about 85%, 90%, 91%, 92%, 93%, 94%, 95%, 96%, 97%, 98%, 99%, or greater, sequence identity with the amino acid sequence set forth in SEQ ID NO:15 wherein the diabody including the variant or variants specifically recognizes and binds to IFN-γ.

The diabody including scFv of SEQ ID NO:14 and/or SEQ ID NO:15 or a variant of either thereof can be isolated or generated recombinantly or synthetically.

Mutations can be introduced using standard molecular biology techniques such as site-directed mutagenesis and PCR-mediated mutagenesis to produce a diabody including a variant of the scFv SEQ ID NO:14 and/or SEQ ID NO:15. One of skill in the art will recognize that one or more amino acid mutations can be introduced without altering the functional properties of the diabody.

Variants of the diabody $V_H$ and $V_L$ domains of SEQ ID NO:11 and SEQ ID NO:12 can also be included in a labeled-antibody conjugate according to embodiments.

A functional variant of the diabody $V_H$ and $V_L$ domains of SEQ ID NO:11 and SEQ ID NO:12 has at least about 85%, 90%, 91%, 92%, 93%, 94%, 95%, 96%, 97%, 98%, 99%, or greater, sequence identity with the amino acid sequences set forth in SEQ ID NO:11 and SEQ ID NO:12 wherein the diabody including the variant or variants specifically recognizes and binds to IFN-γ.

The diabody including $V_H$ and $V_L$ domains of SEQ ID NO:11 and SEQ ID NO:12 or a variant of either thereof can be isolated or generated recombinantly or synthetically.

Mutations can be introduced using standard molecular biology techniques such as site-directed mutagenesis and PCR-mediated mutagenesis to produce a diabody including a variant of $V_H$ and $V_L$ domains of SEQ ID NO:11 and SEQ ID NO:12. One of skill in the art will recognize that one or more amino acid mutations can be introduced without altering the functional properties of the diabody.

Conservative amino acid substitutions can be made in the diabody sequences of SEQ ID NO:11, SEQ ID NO:12, and/or SEQ ID NO:14, to produce functional variants. Conservative amino acid substitutions are art recognized substitutions of one amino acid for another amino acid having similar characteristics. For example, each amino acid can be described as having one or more of the following characteristics: electropositive, electronegative, aliphatic, aromatic, polar, hydrophobic, and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine, and valine; aromatic amino acids include phenylalanine, tyrosine, and tryptophan; polar amino acids include aspartate, glutamate, histidine, lysine, asparagine, glutamine, arginine, serine, threonine, and tyrosine; and hydrophobic amino acids include alanine, cysteine, phenylalanine, glycine, isoleucine, leucine, methionine, proline, valine, and tryptophan; and conservative substitutions include substitutions among amino acids within each group. Amino acids can also be described in terms of steric effects or relative size, e.g., alanine, cysteine, aspartate, glycine, asparagine, proline, threonine, serine, and valine are all typically considered to be small.

To determine the percent identity of two amino acid sequences, the sequences are aligned for optimal comparison purposes (e.g., gaps can be introduced in a first amino acid or nucleotide sequence for optimal alignment with a second amino acid or nucleotide sequence using the default parameters of an alignment software program). The amino acids at corresponding amino acid positions are then compared. When a position in the first sequence is occupied by the same amino acid as the corresponding position in the second sequence, then the sequences are identical at that position. The percent identity between the two sequences is a function of the number of identical positions shared by the sequences (i.e., % identity=number of identical aligned positions÷total number of aligned positions·100%). In some embodiments, the two sequences have the same length.

The determination of percent identity between two sequences can be accomplished using a mathematical algorithm. A non-limiting example of a mathematical algorithm utilized for the comparison of two sequences is the algorithm of Karlin and Altschul, 1990, PNAS USA 87:2264-68, e.g., as modified as in Karlin and Altschul, 1993, PNAS USA 90:5873-77. In calculating percent identity, only exact matches are typically counted.

Other methods of cleaving antibodies, such as, e.g., separation of heavy chains to form monovalent light-heavy chain fragments, further cleavage of fragments, or other enzymatic, chemical or genetic techniques may also be used, so long as the antibody fragments specifically bind to the antigen that is recognized by the intact antibody.

The detection label or radionuclide therapeutic agent is conjugated directly, or indirectly, to the antibody to produce an antibody conjugate. Suitable linkers, chelating agents and methods of use for conjugation of a detection label or radionuclide therapeutic agent to an antibody are well-known in the art, see for example, Shan S. Wong et al., Chemistry of Protein and Nucleic Acid Cross-Linking and Conjugation, Second Edition, CRC Press, 2011.

According to aspects of the present disclosure, an antibody conjugate is an imaging agent which can be used in diagnostic procedures as well as for localization of activated T cells. Imaging can be performed by many procedures well-known to those having ordinary skill in the art, for example, by positron emission tomography (PET), single photon emission computed tomography (SPECT), Cerenkov imaging, photoacoustic imaging, ultrasound imaging, optical coherent tomography, optical imaging, including fluorescence imaging, and/or bioluminescence imaging, or a combination of any two or more thereof.

In embodiments, the labeled-antibody conjugates include at least one detection label conjugated to the antibody, wherein the at least one detection label includes a radionuclide tracer. In embodiments, the at least one detection label is a combination of a radionuclide tracer and a fluorophore.

In embodiments, the radionuclide tracer is selected from $^{11}C$, $^{13}N$, $^{15}O$, $^{18}F$, $^{44}Sc$, $^{45}Ti$, $^{52}Mn$, $^{64}Cu$, $^{68}Ga$ $^{76}Br$, $^{82}Rb$, $^{86}Y$ $^{89}Zr$, $^{99m}Tc$, $^{186}In$, $^{124}I$, $^{131}I$, $^{186}Re$, $^{43}K$, $^{52}Fe$, $^{57}Co$, $^{67}Cu$, $^{67}Ga$ $^{77}Br$, $^{81}Rb$, $^{81m}Kr$, $^{87m}Sr$, $^{89}Zr$, $^{113m}In$, $^{123}I$, $^{125}I$, $^{127}Cs$, $^{129}Cs$, $^{132}I$, $^{177}Lu$, $^{186}Re$, $^{197}Hg$, $^{203}Pb$, $^{206}Bi$, $^{225}Ac$, $^{225}Ra$, or combination of any two or more thereof. In illustrative, non-limiting embodiments, the radionuclide tracer is $^{89}Zr$.

In embodiments wherein the detection label is a radionuclide tracer, the radionuclide tracer is optionally conjugated to the antibody with a bifunctional chelator. In embodiments wherein the radionuclide tracer is $^{11}C$, $^{13}N$, $^{18}F$, $^{76}Br$, $^{123}I$, $^{124}I$, or $^{125}I$, a bifunctional chelator is not required for conjugation to the antibody wherein $^{11}C$, $^{13}N$, $^{18}F$, $^{76}Br$, $^{123}I$, $^{124}I$, or $^{125}I$, can be directly conjugated to the antibody with standard techniques known to those of ordinary skill in the art. In embodiments, the bifunctional chelator includes a chelator attached to a first linking group. Suitable chelators and first linking groups are known to those of ordinary skill in the art. In embodiments, the bifunctional chelator includes a chelator selected from DFO, NOTA, DOTA, EDTA, DOPA, DTPA, NODA, or a combination of any two or more thereof. In illustrative, non-limiting embodiments, the bifunctional chelator is p-SCN-Bn-DFO.

In embodiments, the bifunctional chelator is attached to the antibody. In further embodiments, the radionuclide tracer is complexed to the bifunctional chelator, wherein the bifunctional chelator is covalently attached to the antibody. In embodiments, the bifunctional chelator is attached to the antibody by reacting the bifunctional chelator with the antibody by standard techniques known to those of ordinary skill in the art. In embodiments, an ion of the radionuclide tracer is complexed to the bifunctional chelator by standard techniques known to those of ordinary skill in the art. In illustrative, non-limiting embodiments, (1) the bifunctional chelator p-SCN-Bn-DFO is reacted with the anti-IFN-γ antibody at a ratio of about 5:1 in saline solution at a pH ~ 9 for about 1 hour at about 37° C. for covalent attachment thereof, and (2) the radionuclide tracer $^{89}Zr^{4+}$ is reacted with the bifunctional chelator p-SCN-Bn-DFO covalently attached to the antibody at a pH ~ 7.0-7.2 for about 1 hour at room temperature to form a radiolabeled-antibody conjugate.

In embodiments, the labeled-antibody conjugates include at least one detection label conjugated to the antibody, wherein the at least one detection label includes a radionuclide tracer. In embodiments, the at least one detection label also includes a fluorophore. In embodiments, the fluorophore is a fluorescent dye. In embodiments, the fluorophore emits fluorescence in the visible (i.e., 400-700 nm) or near-infrared (i.e., 700-1400 nm) region.

In embodiments, the antibody conjugates include therapeutic radionuclide-antibody conjugates. In embodiments, therapeutic radionuclide-antibody conjugates include an antibody that specifically recognizes and binds IFN-γ, a bifunctional chelator conjugated to the antibody, and a radionuclide therapeutic agent complexed to the bifunctional chelator. In embodiments, the antibody is as described herein with regard to labeled-antibody conjugates. Additionally, in embodiments, the bifunctional chelator is as described herein with regard to labeled-antibody conjugates.

In embodiments, the therapeutic radionuclide-antibody conjugate includes a radionuclide therapeutic agent complexed to the bifunctional chelator. In embodiments, the radionuclide therapeutic agent is selected from $^{125}I$, $^{131}I$, $^{177}Lu$, $^{186}Re$, $^{225}Ac$, $^{225}Ra$, or a combination of any two or more thereof. In embodiments, the bifunctional chelator is attached to the antibody. In further embodiments, the radionuclide therapeutic agent is complexed to the bifunctional chelator, wherein the bifunctional chelator is covalently attached to the antibody. In embodiments, the bifunctional chelator is attached to the antibody by reacting the bifunctional chelator with the antibody. Then, in embodiments, an ion of the radionuclide therapeutic agent is complexed to the bifunctional chelator.

In embodiments, the therapeutic radionuclide-antibody conjugate includes a labeled-antibody conjugate attached to a therapeutic moiety. The therapeutic moiety can be, without limitation, a small molecule drug, an oligonucleotide or polynucleotide, such as an antisense oligonucleotide or polynucleotide, an siRNA, an mRNA, an miRNA, an shRNA, a peptide or protein. According to embodiments, a therapeutic moiety is attached to, enclosed in or partially enclosed in, a particle.

An included particle can be selected from among a lipid particle; a polymer particle; an inorganic particle; and an inorganic/organic particle. A mixture of particle types can also be included. The particles can be of any shape, size, composition, or physicochemical characteristics compatible with administration to a subject. The particles can be organic or inorganic particles, such as glass or metal and can be particles of a synthetic or naturally occurring polymer, such as polystyrene, polycarbonate, silicon, nylon, cellulose, agarose, dextran, and polyacrylamide.

In particular aspects, the particle is a lipid particle including, but not limited to, liposomes, micelles, unilamellar or mulitlamellar vesicles; polymer particles such as hydrogel particles, polyglycolic acid particles or polylactic acid particles; inorganic particles such as calcium phosphate particles such as described in for example U.S. Pat. No. 5,648,097; and inorganic/organic particulate carriers such as described for example in U.S. Pat. No. 6,630,486. Further description of liposomes and methods relating to their preparation and use may be found in Liposomes: A Practical Approach (The Practical Approach Series, 264), V. P. Torchilin and V. Weissig (Eds.), Oxford University Press; 2nd ed., 2003.

An included particle is typically formulated such that the particle has a diameter, or longest dimension, in the range of about 1 nm-10 microns. In particular aspects, an included particle is a nanoparticle, formulated such that the nanoparticle has a diameter, or longest dimension, in the range of about 1 nm-about 1000 nm. Further aspects of nanoparticles are described in S. M. Moghimi et al., FASEB J. 2005, 19, 311-30; Choi, et al., Mol Imaging. 2010 December; 9(6): 291-310; and Bogart et al., ACS Nano, 2014, 8 (4), pp 3107-3122.

II. Methods for Imaging

In one or more embodiments, the disclosure discloses methods for imaging. In embodiments, methods for imaging include: (a) administering a labeled-antibody conjugate to a subject, wherein the labeled-antibody conjugate includes: an antibody that specifically recognizes and binds to IFN-γ, and at least one detection label conjugated to the antibody, wherein the at least one detection label includes a radionuclide tracer; and (b) detecting the presence of the labeled-antibody conjugate in the subject in vivo by imaging. In embodiments, the labeled-antibody conjugate is as described herein with regard to antibody conjugates. In further embodiments, the antibody and the at least one detection label are as described herein with regard to antibody conjugates.

In embodiments, the methods include administering a labeled-antibody conjugate to a subject. In embodiments, the methods include administering an effective amount of a labeled-antibody conjugate to a subject. The labeled-antibody conjugate may be administered by any suitable route known to those of ordinary skill in the art. In embodiments, administration of the labeled-antibody conjugate is by intravenous, intraarterial, intraperitoneal, intramuscular, subcutaneous, intrapleural, intrathecal, intratumoral, perfusion through a regional catheter, and/or direct intralesional injection. In embodiments wherein the labeled-antibody conjugate is administered by injection, the administration may be by continuous infusion, by single bolus, and/or by multiple boluses. In some embodiments, administering the radiolabeled-antibody conjugate is non-immunogenic to the subject. In embodiments, the subject is a mammal. In some embodiments, the subject is a mammal selected from humans, non-human primates, canines, felines, murines, bovines, equines, ovines, porcines, and lagomorphs. In illustrative, non-limiting embodiments, the subject is a mouse or a human.

In embodiments, the labeled-antibody conjugate administered to a subject includes a radionuclide tracer. In some embodiments, the labeled-antibody conjugate administered to a subject includes a radionuclide tracer only, i.e. without a fluorophore.

In embodiments, the radionuclide tracer is selected from $^{11}C$, $^{13}N$, $^{15}O$, $^{18}F$, $^{44}Sc$, $^{45}Ti$, $^{52}Mn$, $^{64}Cu$, $^{68}Ga$, $^{76}Br$, $^{82}Rb$, $^{86}Y$, $^{89}Zr$, $^{99m}Tc$, $^{111}In$, $^{124}I$, $^{131}I$, $^{186}Re$, $^{43}K$, $^{52}Fe$, $^{57}Co$, $^{67}Cu$, $^{67}Ga$, $^{77}Br$, $^{81}Rb$, $^{81m}Kr$, $^{87m}Sr$, $^{89}Zr$, $^{113m}In$, $^{123}I$, $^{125}I$, $^{127}Cs$, $^{129}Cs$, $^{132}I$, $^{177}Lu$, $^{186}Re$, $^{197}Hg$, $^{203}Pb$, $^{206}Bi$, $^{225}Ac$, $^{225}Ra$, or combination of any two or more thereof.

In illustrative, non-limiting embodiments, the radionuclide tracer is $^{89}Zr$.

In alternative embodiments, the labeled-antibody conjugate administered to a subject includes a fluorophore. In embodiments, the fluorophore is a fluorescent dye.

In embodiments, the methods for imaging include detecting the presence of the labeled-antibody conjugate in the subject in vivo by imaging. In embodiments, the presence of the labeled-antibody conjugate is detected in real time. In embodiments, the presence of the labeled-antibody conjugate is detected non-invasively and/or minimally-invasively.

In embodiments wherein the labeled-antibody conjugate includes a radionuclide tracer, the presence of the labeled-antibody conjugate may be detected in vivo by PET imaging, SPECT imaging, or combination thereof. In embodiments wherein the radionuclide tracer is selected from $^{11}C$, $^{13}N$, $^{15}O$, $^{18}F$, $^{64}Cu$, $^{68}Ga$, $^{76}Br$, $^{82}Rb$, $^{86}Y$, $^{89}Zr$, $^{124}I$ or a combination of any two or more thereof, the presence of the labeled-antibody conjugate may be detected in vivo by PET imaging. In embodiments wherein the radionuclide tracer is selected from $^{99m}Tc$, $^{111}In$, $^{131}I$, $^{186}Re$, or a combination of any two or more thereof, the presence of the labeled-antibody conjugate may be detected in vivo by SPECT imaging.

In embodiments wherein the labeled antibody conjugate includes a fluorophore, the presence of the labeled-antibody conjugate may be detected in vivo by optical imaging. Various in vivo optical imaging techniques are known to those of ordinary skill in the art. (See e.g., Ntziachristos, Annu. Rev. Biomed. Eng. 2006, 8:1-33; Troyan, S. L. et al., Ann. Surg. Oncol. 16, 2943-2952 (2009); Luker, G. D. & Luker, K. E., J. Nucl. Med. 49, 1-4 (2008); Tromberg, B. J. et al., Med. Phys. 35, 2443-2451 (2008), and their potential applicability to imaging-guided diagnostic and surgical methods has been proposed in several preclinical studies; Kirsch, D. G. et al., Nat. Med. 13, 992-997 (2007); von Burstin, J. et al., Int. J Cancer 123, 2138-2147 (2008); and U.S. Pat. No. 9,409,923). In embodiments, in vivo optical imaging is selected from confocal microscopy, planar imaging, fluorescence molecular tomography, complete projection tomography, fluorescence tomography direct imaging, two-photon in vivo imaging or a combination of any two or more thereof. In further embodiments, planar imaging is selected from epi-illumination (i.e., photographic) imaging, trans-illumination imaging, tomographic imaging, or a combination of any two or more thereof.

In embodiments wherein the presence of the labeled-antibody conjugate is detected by in vivo optical imaging, the fluorophore may be selected such that it emits fluorescence in the visible or near-infrared region. In illustrative, non-limiting embodiments, fluorophores emitting fluorescence in the visible or near-infrared region may be selected from fluorescein, Cy2, Cy3, Cy3B, Cy3.5, Cy5, Cy5.5, Cy7, Texas Red® (Molecular Probes, Inc., Eugene, Oreg.), AlexaFluor® (Molecular Probes, Inc., Eugene), AlexaFluor 350, AlexaFluor 405, AlexaFluor 430, AlexaFluor 488, AlexaFluor 500, AlexaFluor 532, AlexaFluor 546, AlexaFluor 568, AlexaFluor 594, AlexaFluor 610, AlexaFluor 633, AlexaFluor 647, AlexaFluor 660, AlexaFluor 680, AlexaFluor 700, AlexaFluor 750, BODIPY FL, BODIPY R6G, BODIPY TMR, BOPDIPY 530/550, BODIPY 558/568, BODIPY 564/570, BODIPY 576/589, BODIPY 581/591, BODIPY 630/650, BODIPY 650/665, Rhodamine Green™-X (Molecular Probes, Inc.), Rhodamine Red™-X (Molecular Probes, Inc.), Rhodamine 6G, TMR, TAMRA™ (Applied Biosystems), or a combination of any two or more thereof.

In embodiments the presence of the labeled-antibody conjugate is detected by in vivo photoacoustic imaging. In illustrative, non-limiting embodiments, photoacoustic dyes included in the conjugate may be selected from Methylene blue, Evan's blue, Trypan blue, Patent blue, Indocyanine Green, IRDye800CW, DiR, Cy7, Cy7.5, and porphyrins or a combination of any two or more thereof.

In embodiments wherein the labeled antibody conjugate includes a combination of a radionuclide tracer and a fluorophore, the presence of the labeled-antibody conjugate may be detected in vivo by a combination of PET or SPECT and optical imaging.

In embodiments wherein the labeled antibody conjugate includes a combination of a radionuclide tracer and a fluorophore, the presence of the labeled-antibody conjugate may be detected in vivo by a combination of PET or SPECT and photoacoustic imaging.

In embodiments the presence of the labeled-antibody conjugate may be detected in vivo by a combination of any two or more of: PET, SPECT, Cerenkov imaging, photoacoustic imaging, ultrasound imaging, optical coherent tomography, optical imaging, including fluorescence imaging, and/or bioluminescence imaging.

According to embodiments, a method for imaging a subject includes 1) administering a labeled-antibody conjugate to a subject, wherein the labeled-antibody conjugate includes: an antibody that specifically binds to IFN-γ, and a detection label conjugated to the antibody, wherein the detection label is a radionuclide tracer or fluorophore; and 2) detecting the presence of the labeled-antibody conjugate in the subject in vivo by imaging. According to particular embodiments, the subject has cancer. According to particular embodiments, the cancer is bladder cancer, brain tumors, breast cancer, cervical cancer, colorectal cancer, kidney cancer, leukemia, lung cancer, melanoma, myeloma, pancreatic cancer, gastric cancer, intestinal cancer, esophageal cancer, mesothelioma cancer, endometrial cancer, ovarian cancer, head and neck cancer, bone cancer, sarcoma, cholangiocarcinoma, gall bladder cancer, testicular cancer, thyroid cancer, or prostate cancer.

According to particular embodiments, the subject has an inflammatory condition or a disease associated with inflammation, such as, but not limited to, infection, tissue injury, Alzheimer's disease, obesity, stroke, heart attack, Hepatitis C, and Crohn's disease.

Combination Treatments

Combinations of a labeled-antibody conjugate and at least one therapeutic agent are administered according to aspects of the present invention. In some embodiments, a labeled-antibody conjugate and at least one additional active agent are administered to a subject to treat cancer in a subject in need thereof. In still further aspects, a labeled-antibody conjugate and at least two additional active agents are administered to a subject to treat cancer in a subject in need thereof.

The term "additional active agent" is used herein to denote a chemical compound, a mixture of chemical compounds, a biological macromolecule (such as a nucleic acid, an antibody, a protein or portion thereof, e.g., a peptide). The additional active agent can be, without limitation, a small molecule drug, an oligonucleotide or polynucleotide, such as an antisense oligonucleotide or polynucleotide, an siRNA, an mRNA, an miRNA, an shRNA, a peptide or protein. An additional active agent can be a therapeutic agent or a diagnostic agent according to embodiments.

Additional active agents which are therapeutic agents included in aspects of methods and compositions of the present invention include, but are not limited to, antibiotics, antivirals, antineoplastic agents, analgesics, antipyretics, antidepressants, antipsychotics, anti-cancer agents, antihistamines, anti-osteoporosis agents, anti-osteonecrosis agents, antiinflammatory agents, anxiolytics, chemotherapeutic agents, diuretics, growth factors, hormones, non-steroidal antiinflammatory agents, steroids and vasoactive agents.

According to embodiments, combination treatments include: (1) administration of pharmaceutical compositions that include a labeled antibody conjugate in combination with one or more additional active agents; (2) co-administration of a labeled antibody conjugate with one or more additional active agents wherein the labeled antibody conjugate and the one or more additional active agents are formulated in the same composition and (3) co-administration of a labeled antibody conjugate with one or more additional active agents wherein the labeled antibody conjugate and the one or more additional therapeutic agents have not been formulated in the same composition. When using separate formulations, the labeled antibody conjugate and the one or more additional active agents may be administered at the same time or at different times.

An adjunct anti-cancer treatment can be administered in combination with a labeled antibody conjugate, such as prior to, simultaneously with or after administration of the labeled antibody conjugate, such as an anti-cancer radiation treatment of a subject or an affected area of a subject's body.

An additional active agent can be an anti-cancer agent according to embodiments, such as a targeted therapy agent or chemotherapeutic.

Anti-cancer agents are described, for example, in Goodman et al., Goodman and Gilman's The Pharmacological Basis of Therapeutics, 8th Ed., Macmillan Publishing Co., 1990.

Anti-cancer agents illustratively include acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, dromostanolone, duazomycin, edatrexate, eflornithine, elsamitrucin, enloplatin, enpromate, epipropidine, epirubicin, erbulozole, esorubicin, estramustine, etanidazole, etoposide, etoprine, fadrozole, fazarabine, fenretinide, floxuridine, fludarabine, fluorouracil, flurocitabine, fosquidone, fostriecin, fulvestrant, gemcitabine, hydroxyurea, idarubicin, ifosfamide, ilmofosine, interleukin II (IL-2, including recombinant interleukin II or rIL2), interferon alfa-2a, interferon alfa-2b, interferon alfa-n1, interferon alfa-n3, interferon beta-Ia, interferon gamma-Ib, iproplatin, irinotecan, lanreotide, letrozole, leuprolide, liarozole, lometrexol, lomustine, losoxantrone, masoprocol, maytansine, mechlorethamine hydrochloride, megestrol, melengestrol acetate, melphalan, menogaril, mercaptopurine, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, pyrazofurin, riboprine, rogletimide, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, verteporfin, vinblastine, vincristine sulfate, vindesine, vinepidine, vinglycinate, vinleurosine, vinorelbine, vinrosidine, vinzolidine, vorozole, zeniplatin, zinostatin, zoledronate, and zorubicin.

According to embodiments, the additional active agent is an anti-cancer immunotherapy agent. According to embodiments, the anti-cancer immunotherapy agent is an immune checkpoint inhibitor, a cytokine, a vaccine, an adoptive cell transfer therapy, or any therapeutic wherein the mechanism of action of the therapeutic is an increased number of tumor-infiltrating lymphocytes in the subject and/or an increased activation state of a tumor-infiltrating lymphocyte population in the subject. According to embodiments, the immune checkpoint inhibitor is a PD-1 inhibitor, PD-L1 inhibitor, or CTLA-4 inhibitor. According to embodiments, the immune checkpoint inhibitor selected from atezolizumab, avelumab, durvalumab, ipilimumab, nivolumab, pembrolizumab, and an antigen-binding fragment of any one of the foregoing. According to embodiments, the subject is human and the antibody specifically binds to human IFN-γ.

According to embodiments, an anti-cancer immunotherapy agent is administered to a subject and a labeled antibody conjugate is administered simultaneously or subsequently followed by detecting the presence of the labeled-antibody conjugate in the subject in vivo by imaging to image IFN-γ and thereby monitor the effectiveness of the treatment with the anti-cancer immunotherapy agent. According to embodiments, the subject received an anti-cancer immunotherapy prior to administering and detecting the presence of the labeled-antibody conjugate, and wherein the mechanism of action of the immunotherapy results in an increased number of tumor-infiltrating lymphocytes in the subject and/or an increased activation state of a tumor-infiltrating lymphocyte population in the subject; or wherein administering and detecting the presence of the labeled-antibody conjugate is performed prior to administration of a therapy to determine the state of active immunity in the subject. Thus, efficacy of the anti-cancer immunotherapy is monitored non-invasively and in real-time in the subject.

In embodiments, significant binding of the labeled-antibody conjugate to the IFN-γ antigen indicates the presence of activated lymphocytes and/or human cancer cells. In embodiments, significant binding of the labeled-antibody conjugate to the IFN-γ antigen indicates the presence of a localized immune response in the subject. In embodiments, PET imaging is quantitative wherein a correlation is determined between uptake of the radionuclide tracer quantified by radioactivity measurements of excised tissues and uptake estimated noninvasively by PET. Thus, efficacy of the anti-cancer immunotherapy is monitored non-invasively and in real-time in the subject.

According to embodiments, an anti-inflammation immunotherapy agent is administered to a subject and a labeled antibody conjugate is administered simultaneously or subsequently followed by detecting the presence of the labeled-antibody conjugate in the subject in vivo by imaging to image IFN-γ and thereby monitor the effectiveness of the treatment with the anti-inflammation immunotherapy agent. According to embodiments, the subject received an anti-inflammation immunotherapy prior to administering and detecting the presence of the labeled-antibody conjugate, and wherein the mechanism of action of the immunotherapy results in an increased number of activated lymphocytes in the subject and/or an increased activation state of an activated lymphocyte population in the subject; or wherein administering and detecting the presence of the labeled-antibody conjugate is performed prior to administration of a therapy to determine the state of active immunity in the subject. Thus, efficacy of the anti-inflammation immunotherapy is monitored non-invasively and in real-time in the subject.

In embodiments, significant binding of the labeled-antibody conjugate to the IFN-γ antigen indicates the presence of activated lymphocytes. In embodiments, significant binding of the labeled-antibody conjugate to the IFN-γ antigen indicates the presence of a localized immune response in the subject. In embodiments, PET imaging is quantitative wherein a correlation is determined between uptake of the radionuclide tracer quantified by radioactivity measurements of excised tissues and uptake estimated noninvasively by PET. In embodiments, PET imaging is quantitative wherein uptake of the radionuclide tracer is quantified by analysis of acquired images. Thus, efficacy of the anti-inflammation immunotherapy is monitored non-invasively and in real-time in the subject.

According to embodiments, methods for imaging a subject include administering a labeled-antibody conjugate to a subject, wherein the labeled-antibody conjugate comprises: an antibody that specifically binds to IFN-γ, and a detection label conjugated to the antibody, wherein the detection label is a radionuclide tracer or fluorophore; and detecting the presence of the labeled-antibody conjugate in the subject in vivo by imaging.

According to embodiments, a labeled-antibody conjugate is administered to a subject prior to immunotherapy treatment, wherein the labeled-antibody conjugate includes an antibody that specifically binds to IFN-γ, and a detection label conjugated to the antibody, wherein the detection label is a radionuclide tracer or fluorophore; and the presence of the labeled-antibody conjugate in the subject is detected in vivo by imaging to establish a baseline reading indicative of a baseline level of IFN-γ to determine the state of active immunity in the subject. An immunotherapy is then administered wherein the mechanism of action of the immunotherapy results in an increased number of activated lymphocytes in the subject and/or an increased activation state of an activated lymphocyte population in the subject. The labeled-antibody conjugate is then administered to a subject again after the administration of the immunotherapy to establish a post-treatment reading indicative of a subsequent level of IFN-γ to determine the state of active immunity in the subject. The steps of administration of the immunotherapy and administration/detection of the labeled-antibody conjugate may be performed 2, 3, 4, 5, 6, 7, 8, 9, 10, or more times, over a period of treatment time in the range of 1, 2, 3, 4, 5, 6, 7, 8, 9, 10, 11, 12, 13, 14, 15, 16, 17, 18, 19, 20, 21, 22, 23, 24 or more hours, 1, 2, 3, 4, 5, 6, 7, or more days, 1, 2, 3, 4, 5, 6, 7, 8, or more weeks, 2, 3, 4, 5, 6, 7, 8, 9, 10, 11, 12, 13, 14, 15, 16, 17, 18, 19, 20, 21, 22, 23, 24 or more months, 2, 3, 4, 5, 6, 7, 8, 9, 10, 15, 20 or more years, depending on the course of the disease and the course of treatment.

According to embodiments, a labeled-antibody conjugate is administered to a subject prior to immunotherapy treatment of cancer in a subject having or suspected of having cancer, wherein the labeled-antibody conjugate includes an antibody that specifically binds to IFN-γ, and a detection label conjugated to the antibody, wherein the detection label is a radionuclide tracer or fluorophore; and the presence of the labeled-antibody conjugate in the subject is detected in vivo by imaging to establish a baseline reading indicative of a baseline level of IFN-γ to determine the state of active immunity in the subject. An anti-cancer immunotherapy is then administered wherein the mechanism of action of the anti-cancer immunotherapy results in an increased number of tumor-infiltrating lymphocytes in the subject and/or an increased activation state of a tumor-infiltrating lymphocyte population in the subject. The labeled-antibody conjugate is then administered to a subject again after the administration of the anti-cancer immunotherapy to establish a post-treatment reading indicative of a subsequent level of IFN-γ to determine the state of active immunity in the subject. The steps of administration of the anti-cancer immunotherapy and administration/detection of the labeled-antibody conjugate may be performed 2, 3, 4, 5, 6, 7, 8, 9, 10, or more times, over a period of treatment time in the range of 1, 2, 3, 4, 5, 6, 7, 8, 9, 10, 11, 12, 13, 14, 15, 16, 17, 18, 19, 20, 21, 22, 23, 24 or more hours, 1, 2, 3, 4, 5, 6, 7, or more days, 1, 2, 3, 4, 5, 6, 7, 8, or more weeks, 2, 3, 4, 5, 6, 7, 8, 9, 10, 11, 12, 13, 14, 15, 16, 17, 18, 19, 20, 21, 22, 23, 24 or more months, 2, 3, 4, 5, 6, 7, 8, 9, 10, 15, 20 or more years, depending on the course of the disease and the course of treatment.

III. Mouse Models

In one or more embodiments, the disclosure discloses mouse models.

In embodiments, the mouse models include: a mouse having a human cancer xenograft and a labeled-antibody conjugate, wherein the labeled-antibody conjugate includes: an antibody that specifically recognizes and binds to IFN-γ, and at least one detection label conjugated to the antibody, wherein the at least one detection label is selected from a radionuclide tracer or a fluorophore. In embodiments, the labeled-antibody conjugate is as described herein with regard to antibody conjugates and methods of imaging.

In embodiments, the mouse model has a human cancer xenograft. In embodiments, the human cancer xenograft is transplanted into the mouse. In embodiments, the human cancer xenograft is established from human cancer cells, human cancer tissues, or combination thereof. In embodiments, the human cancer xenograft includes human cancer cells and/or human cancer tissues of primary cancer and/or metastatic cancer. In embodiments, the human cancer xenograft includes human cancer cells and/or human cancer tissues of primary cancer and/or metastatic cancer selected from brain cancer, melanoma, colon cancer, kidney cancer, prostate cancer, breast cancer, gastric cancer, pancreatic cancer, ovarian cancer and testicular cancer.

In embodiments, the mouse model having a human cancer xenograft is immunodeficient and further includes engrafted human hematopoetic stem cells such that the mouse has a "humanized" immune system which produces human IFN-γ.

In embodiments, the methods include determining the effect of the composition or treatment on the growth of a human cancer xenograft in the mouse. In embodiments, the effect of the composition or treatment on the growth of the human cancer xenograft is determined by imaging. In embodiments, suitable imaging techniques include those described herein with regard to imaging methods. In embodiments, the effect of the composition or treatment is determined by comparing the growth of the human cancer xenograft in the mouse administered the composition or treatment to growth of a human cancer xenograft in a mouse not administered the composition or treatment.

In embodiments, the mouse models include: a mouse having an injury or infection and a labeled-antibody conjugate, wherein the labeled-antibody conjugate includes: an antibody that specifically recognizes and binds to IFN-γ, and at least one detection label conjugated to the antibody, wherein the at least one detection label is selected from a radionuclide tracer or a fluorophore. In embodiments, the labeled-antibody conjugate is as described herein with regard to antibody conjugates and methods of imaging immune-mediated treatment for injury or infection.

In embodiments, the mouse models include: an immune competent mouse having a murine cancer, such as an allograft or induced murine tumor, and a labeled-antibody conjugate, wherein the labeled-antibody conjugate includes: an antibody that specifically recognizes and binds to murine IFN-γ, and at least one detection label conjugated to the antibody, wherein the at least one detection label is selected from a radionuclide tracer or a fluorophore. In embodiments, the labeled-antibody conjugate is as described herein with regard to antibody conjugates and methods of imaging.

Examples

The following non-limiting examples illustrate the methods and compositions of the present disclosure.

Mice

Female BALB/c mice (6-8 week old) were purchased from Charles River Laboratories (Wilmington, Mass.). Heterozygous BALB/NeuT (NeuT) mice were in-house bred. NeuT male mice, which express a transforming rat neu, develop atypical ductal hyperplasia in 1-2 parotid glands by 6 weeks of age which progresses to multifocal acinic cell adenocarcinoma in situ at about 19 weeks of age.

Radiochemistry

All antibodies were obtained from eBioscience (San Diego, Calif.) whereas the non-specific IgG isotype controls were purchased from Jackson ImmunoResearch (Westgrove, Pa.) and Thermo Fisher (Waltham, Mass.) unless otherwise stated. Chelators were obtained from Macrocyclics (Plano, Tex.). Radioisotopes were obtained from 3D Imaging, LLC (Little Rock, Ark.). Synthesis of $^{89}$Zr-anti-CD3, $^{89}$Zr-anti-IFN-γ, and non-specific $^{89}$Zr-anti-IgG was achieved as described herein. For this synthesis, p-SCN-Bn-Desferrioxamine (DFO, Macrocyclics, Plano, Tex.) was incubated with 145-2C11 (anti-CD38, Armenian hamster, IgG, eBioscience, San Diego, Calif.), or AN-18 (anti-IFNγ, rat IgG1, kappa, eBioscience, San Diego, Calif.) at a ratio of 1:5 (Ab:DFO) in phosphate buffered saline at pH ~9 for 1 h at 37° C. and purified via centrifugation with molecular weight column filter (MWCO: 30 kDa, GE Vivaspin 500). Facile $^{89}$Zr-radiolabeling (3D Imaging, Little Rock, Ark.) of the 145-2C11- or AN-18-conjugates proceeded in a neutral pH environment in saline at room temperature after 1 h of incubation. Unbound $^{89}$Zr ($t_{1/2}$=3.27 d) was removed via centrifugation with molecular weight column filters (MWCO: 30 kDa, GE Vivaspin 500). Labeling yields of >85% were achieved as monitored through radio-instant thin layer chromatography (iTLC, MiniScan, Eckert and Ziegler, Berlin, Germany) within 1 h. A radiochemical purity of >98% was obtained after filtration based on iTLC. Specific activities of 4.20±0.12 mCi/mg for $^{89}$Zr-anti-IFN-γ and 3.98±0.08 mCi/mg for $^{89}$Zr-anti-CD3 were achieved.

PET Imaging

Tumor-bearing animals were injected intravenously (i.v.). with the radiolabeled antibody (~180-240 μCi/mouse, 42.8-57.1 μg in 150 μL sterile saline) in the lateral tail vein. Imaging was acquired from 4-120 h post-injection (p.i.). The animals were anesthetized with 3-5% isoflurane (Baxter Healthcare, Deerfield, Ill.) in air for induction, then lowered to 1.5-2% for maintenance. Images were acquired with a microPET R4 camera (Siemens Medical Solutions, USA formerly Concorde Microsystems). Manually drawn 3-dimensional volumes-of-interest (VOI) were selected to determine maximum and mean percent injected dose per gram (% ID/g) in various tissues. Images were decay-corrected to the time of injection and analyzed for labeled-antibody conjugate uptake using ASIpro VM™ software v. 6.3.3.0.

Detecting Elevated IFN-γ in Mice Treated with the TLR9 Agonist CpG-ODN

IFN-γ was systemically induced in naïve BALB/c mice by intramuscular (i.m.) injection of 100 μg CpG-ODN (CpG-oligodeoxynucleotides, Integrated DNA Technologies, Coralville, Iowa). Within an hour of treatment, the mice were injected with $^{89}$Zr-anti-IFN-γ in the lateral tail vein for imaging (180-240 μCi/mouse, 49.9±7.2 μg). PET imaging was conducted at 72 h p.i. Labeled-antibody conjugate uptake within the spleen and peripheral immune tissues were analyzed and compared against a control, untreated group.

Biodistribution and Competitive Inhibition Blocking Assay

Mice were injected i.v. in the lateral tail vein with $^{89}$Zr-anti-IFN-γ (20-30 μCi, 4.7-7.1 μg) in 100-150 μL saline followed by euthanasia via $CO_2$ asphyxiation after 72 h p.i., the time point identified at which tumor-to-background is sufficient. For blocking studies, 80 μg of cold AN-18 was co-injected with the probe in a separate cohort of mice. Select organs were harvested post-sacrifice, weighed and measured for bound radioactivity with a gamma counter (Perkin Elmer 2480 Wizard 2). The % ID/g was calculated as the % of activity bound to the tissue normalized against total administered activity per gram of tissue weight.

In Vitro $^{89}$Zr-Anti-IFN-γ Internalization Assay

TUBO cells ($4.5 \times 10^5$) were plated into 6 well plates in triplicate and allowed to adhere overnight. In separate wells, cells were either left untreated or incubated with recombinant IFN-γ (10 ng/mL) for 15 minutes before being washed 3 times with PBS. $^{89}$Zr-anti-IFN-γ (150 ng, 0.63 nCi) was added and cells were incubated for 1 h at 37° C. Following the incubation period, the media was collected and the cells were rinsed with 1× phosphate buffered saline (PBS) twice. Surface-bound activity was removed by washing the cells in 100 mM acetic acid+100 mM glycine (1:1, pH 3.5) at 4° C. The cells were then lysed with 1 M NaOH. All washes (media plus PBS, acid and alkaline) were collected in separate tubes and measured for bound activity using a gamma counter (Perkin Elmer). The %-internalized activity was calculated as the ratio of the activity of the lysate and the total activity collected from the media, PBS, acid and base washes, normalized to 450,000 cells counted using a Countess II Automated Cell Counter (Thermo Fisher).

Tumor Inoculation

The neu$^+$ TUBO line cloned from a spontaneous mammary tumor in a female NeuT mouse was obtained through Dr. Guido Forni (U. Torino, Torino, Italy). Mice were inoculated in the #4 mammary fat pad with $2.5 \times 10^5$ tumor cells. Tumor growth was monitored by palpation and caliper measurement. Tumor volume was calculated as $v=(l \times w^2)/2$.

DNA Vaccination

The HER2/neu DNA vaccine consists of 20 μg of pGM-CSF (encoding murine GM-CSF) and 50 μg pE2TM (encoding the extracellular and transmembrane regions of human HER2) in 50 μL PBS, which is injected i.m. into each gastrocnemius followed immediately by application of electrode gel and square wave electroporation using a BTX830 (BTX Harvard Apparatus, Holliston, Mass.). For NeuT vaccination, mice were depleted of Tregs by intraperitoneal (i.p.) injection of 500 μg anti-CD25 mAb PC61 10 days prior to the first vaccination.

Quantitative Real-Time PCR

Tumor tissue was snap frozen in liquid nitrogen. Total tumor RNA was collected by Trizol preparation (Thermo Fisher, Waltham, Mass.) after homogenization. cDNA was synthesized with ProtoScript II reverse transcriptase (New England Biolabs, MA). Real-time qPCR was conducted with iTaq Universal SYBR Green Supermix (Bio-Rad Laboratories, Hercules, Calif.) using 10 ng cDNA/well and 500 nM primers specific to the indicated gene (Life Tech, Carlsbad, Calif.). Primer sequences used are: CD3 forward primer: CACTCTGGGCTTGCTGATGG, SEQ ID NO:1; CD3 reverse primer: TCATAGTCTGGGTTGGAACAGG, SEQ ID NO:2; CD8 forward primer: GCTGGTAGTCTGCATCCTGCTTC, SEQ ID NO:3; CD8 reverse primer: TTGCTAGCAGGCTATCAGTGTTGTG, SEQ ID NO:4; IFN-γ forward primer: GAGCTCATTGAATGCTTGGC, SEQ ID NO:5; IFN-γ reverse primer: GCGTCATTGAATCACACCTG, SEQ ID NO:6; PD-1 forward primer: CGTCCCTCAGTCAAGAGGAG, SEQ ID NO:7; PD-1 reverse primer: GTCCCTAGAAGTGCCCAACA, SEQ ID NO:8; GAPDH forward primer: AAGCTCACTGGCATGGCCTTC, SEQ ID NO:9; and GAPDH reverse primer: TGCTTCACCACCTTCTTGATGTC, SEQ ID NO: 10.

Relative mRNA quantities are calculated by $2^{-\Delta CT}$ compared to GAPDH.

ELISA

Tumor tissue was homogenized in standard RIPA buffer with protease inhibitor cocktail (Sigma-Aldrich). Protein concentration was measured by BCA assay (ThermoFisher). High protein binding plates (ThermoFisher) were coated with 3 μg/mL anti-mouse-IFN-γ mAb clone AN-18 (eBioscience) in coating buffer (0.1 M $Na_2HPO_4$, pH to 9.0) and washed prior to addition of samples or standard curve using recombinant mouse IFN-γ (Peprotech, Rocky Hill, N.J.) in duplicate. IFN-γ was detected with biotin-conjugated anti-mouse IFN-γ clone R4-6A2 (eBioscience), avidin-HRP (ThermoFisher), and TMB substrate (ThermoFisher).

Serum IgG Measurement

Serum HER2- and neu-specific IgG were quantified by flow cytometry with a BD FACSCanto II flow cytometer (Becton Dickinson, Franklin Lakes, N.J.), using HER2 over-expressing SKOV3 cells or neu transfected 3T3/NKB cells. Serum was incubated with the appropriate cell line at a 1:100 dilution, followed by washes and detection with PE-conjugated anti-mouse IgG secondary antibody and additional washes prior to detection by flow cytometry. Standard curves for HER2 and neu were run using antibody clones TA-1 and 7.16.4, respectively. Regression analysis was conducted using standard curves of anti-HER2 mAb TA-1 (Calbiochem, Burlington, Mass.) or anti-neu mAb 7.16.4 (Calbiochem, Burlington, Mass.).

IFN-γ ELISPOT

HER2- and neu-specific IFN-γ production was measured by ELISPOT assay. For this, recombinant HER2 or neu (10 μg/mL, Sino Biologicals, Beijing, China) were incubated with splenocytes for 48 h in round-bottom wells, followed by transfer to anti-IFN-γ coated (clone AN-18, eBioscience) ELISPOT plates (Millipore Sigma, Burlington, Mass.) for an additional 48 h. Spots were detected by biotinylated anti-IFN-γ (clone R4-6A2, eBioscience) and avidin-HRP (Becton Dickinson, Franklin Lakes, N.J.), followed by enumeration with an ImmunoSpot analyzer (Cellular Technology Limited, Cleveland, Ohio). Results are expressed as spot forming units (SFU) per $10^6$ cells.

Treatment with Anti-Neu mAb 7.16.4

Mice bearing TUBO tumors were injected i.p. 5 times every 3-4 days with sterile-filtered ascites containing 1 mg anti-neu mAb 7.16.4 diluted in PBS to a final volume of 300 μL.

Immunohistochemistry (IHC) and H&E Staining

IHC was performed using anti-CD8 (clone D4W2Z, Cell Signaling) antibody. After euthanasia, tumors were harvested and fixed in formalin before being embedded in paraffin. Blocks were sectioned into 4 μm sections using a Sakura Accu-Cut SRM microtome (Catalog #: SRM-200 CV) and adhered onto positively charged slides (Histomax Plus, VWR). Slides were then incubated for 12 minutes at 65° C. and deparrafinized in washes of xylene and graded alcohols. Antigen retrieval was performed in PT module buffer (TA-250-PM4X, Fisher) for CD8 (1:200). Primary antibody incubations were performed for 1 h at room temperature in a humidified chamber. Secondary antibody incubations and DAB were performed following manufacturers protocols. CD8 T cell enumeration was conducted by a blinded board certified pathologist. Each tumor sample was screened for hotspots of CD8 lymphocytes using a Nikon Eclipse Ci microscope at 100× magnification. The number of CD8+ T lymphocytes were counted in the three regions of highest infiltration at 400× magnification with a 0.55 mm field diameter, and an average was calculated. For H&E staining, tissue sections were subjected to xylenes, graduated alcohol and distilled water washes. They were then stained with hematoxylin (TA-125-MH, Fisher) for 5 minutes, rinsed with an acid wash for 1 minute and a bluing agent for 15 seconds. Eosin staining was applied to slides for 1 minute and slides were rinsed in 95% ethanol three times. Lastly, sections went through a series of graded alcohol and xylenes steps to dehydrate sections in preparation for mounting with Permount (UN1294, Fisher). Pictures were taken with a Spot Idea camera using Spot 5.2 software (Spot, Sterling Heights, Mich.).

Tumor Dissociation and Flow Cytometry

TUBO tumors from untreated BALB/c mice were dissociated using the GentleMACs Dissociator and mouse tumor dissociation kit (Miltenyi, Germany) following the manufacturer protocol. Cells were stained with a combination of either: FITC-conjugated CD45 mAb (clone 30-F11), APC-conjugated TCRα mAb (clone H57-597), and eFluor780-conjugated viability dye or FITC-conjugated CD45 mAb (clone 30-F11), PE-Cy7-conjugated CD8 mAb (clone 53-6.7), APC-conjugated PD-1 mAb (J43), and eFluor780-conjugated viability dye. All antibodies/dyes were purchased from eBioscience (San Diego, Calif.). Samples were analyzed on a BD FACSCantoII flow cytometer (Becton Dickinson, Franklin Lakes, N.J.) and samples were gated on the viable fraction.

Statistical Analyses

Statistical analyses were conducted using GraphPad Prism 7. Data shown are presented as mean±standard deviation. All tests use one-way ANOVA (estimating a different variance for each group) with Tukey's post-test unless otherwise noted. Weekly tumor growth rate for each mouse was calculated by regression analysis of log tumor growth from day 14, when T cells become active after the initial vaccination, until the final measurement on day 38, versus time in weeks. The relationship between the estimated growth rate per week (slope from the regression analysis) for each mouse and the $^{89}$Zr-anti-IFN-γ labeled-antibody conjugate uptake measured at day 28 is assessed using Pearson's correlation. *p<0.05, p<0.01, *p<0.001.

Results $^{89}$Zr-Anti-IFN-γ PET Labeled-Antibody Conjugate Identifies Localized IFN-γ Production The rat mAb AN-18 to murine IFN-γ was labeled with $^{89}$Zr using desferrioxamine as the chelate to produce $^{89}$Zr-anti-IFN-γ in good yields and purities. In mice treated with CpG-ODN to stimulate IFN-γ, whole-body PET images were acquired 72 h p.i., a time point identified to exhibit reliable labeled-antibody conjugate uptake in the tumor, with low liver and blood pool background (FIG. 7A, FIG. 7B, FIG. 8A, FIG. 8B). VOIs drawn on splenic tissues demonstrated higher labeled-antibody conjugate accumulation (3.50±0.61% ID/g, n=3) in CpG-ODN-treated groups compared to untreated controls (Ctrl: 0.83±0.12% ID/g, n=3) (FIG. 1A).

Figure 1B:
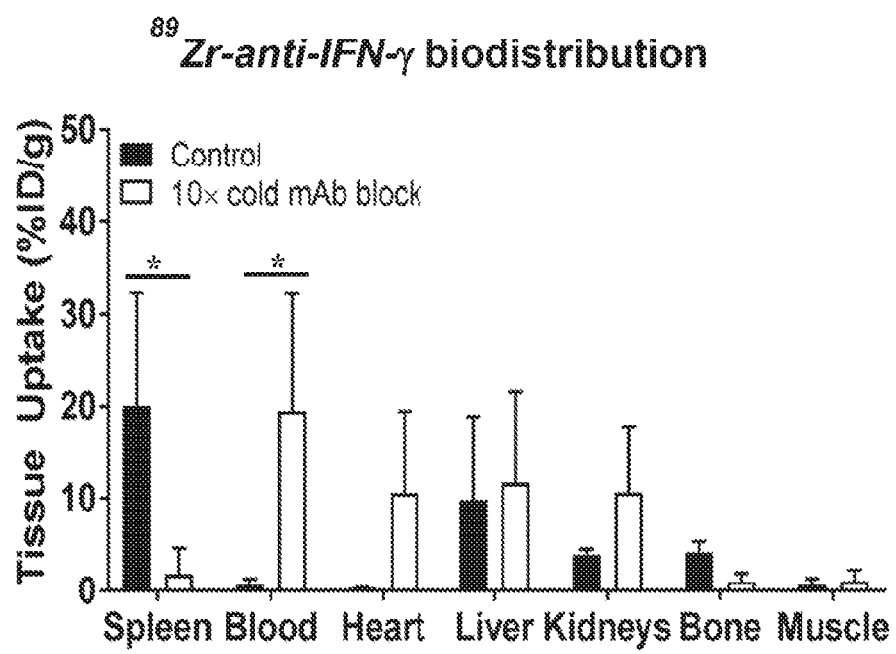
FIG. 1B is a graph showing that tissue distribution of $^{89}$Zr-anti-IFN-γ at 72 h p.i. demonstrated lower probe accumulation in the spleen upon competitive saturation with 10× cold AN-18 mAb (n=4 each)

Tissue distribution of $^{89}$Zr-anti-IFN-γ at 72 h p.i. demonstrated 20.04±12.2% ID/g uptake in the spleen (FIG. 1B, Table 1).

TABLE 1

|  | Control<br>Mean ± S.D. | 10x mAb block<br>Mean ± S.D. | p-value |
| --- | --- | --- | --- |
| Spleen | 20.04 ± 12.20 | 1.88 ± 2.74 | 0.0061 |
| Blood | 0.67 ± 0.69 | 19.46 ± 12.69 | 0.0043 |
| Heart | 0.30 ± 0.04 | 10.57 ± 8.91 | 0.2956 |
| Liver | 9.77 ± 9.12 | 11.69 ± 9.82 | 0.9999 |
| Kidneys | 3.93 ± 0.60 | 10.64 ± 7.18 | 0.7755 |
| Bone | 4.19 ± 1.18 | 1.01 ± 0.94 | 0.9951 |
| Muscle | 0.73 ± 0.65 | 1.08 ± 1.23 | >0.9999 |

Figure 1C:
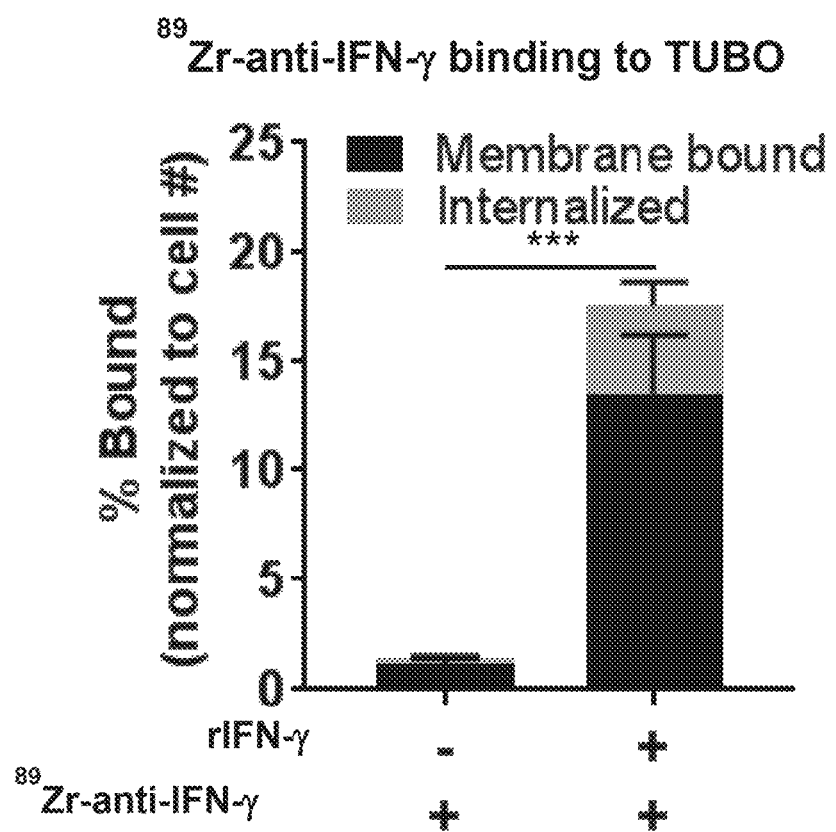
FIG. 1C is a graph showing results of testing $^{89}$Zr-anti-IFN-γ receptor-localized IFN-γ binding in vitro. TUBO cells were incubated with $^{89}$Zr-anti-IFN-γ alone (n=5), or with recombinant IFN-γ (rIFN-γ) and washed before addition of $^{89}$Zr-anti-IFN-γ (n=5). Activity was measured by a gamma counter and adjusted.

Uptake within the blood circulation (0.67±0.69% ID/g), as well as tissues responsible for excretion, liver (9.77±9.12% ID/g), and kidneys (3.93±0.6% ID/g) were low. There was also low uptake in the bone and muscle. Specificity was further confirmed through competitive binding experiment where a decrease in spleen uptake was observed (20.04±12.20 vs. 1.88±2.74% ID/g, n=4, p=0.0061) with 10× cold mAb blockade, consequently increasing non-specific tissue accumulation in the blood (19.46±12.69% ID/g, p=0.0043), heart (10.57±8.91, p=0.30), and liver (11.69±9.82% ID/g, p=0.99). Notable differences in splenic uptake in the imaging and tissue distribution (10-fold lower mass) are due to "mass effects", wherein a greater mass of protein administered potentially saturated receptor binding sites and rendered slower pharmacokinetics. Since IFN-γ is a soluble protein, the mechanism of localized IFN-γ imaging was investigated. Plated TUBO tumor cells were exposed to IFN-γ and/or $^{89}$Zr-anti-IFN-γ labeled-antibody conjugate in quintuplicate followed by analysis of membrane binding and internalization (FIG. 1C). TUBO cells incubated with $^{89}$Zr-anti-IFN-γ alone show limited labeled-antibody conjugate surface binding (1.13±0.28%) and internalization (0.29±0.13%). When TUBO is pre-incubated with IFN-γ, enhanced $^{89}$Zr-anti-IFN-γ surface binding (13.62±2.60%) and internalization (3.93±1.07%) is observed (membrane: p=0.00039, internalized: p=0.0015). Detection of labeled-antibody conjugate binding to TUBO cells after IFN-γ exposure suggests localized imaging may be due to sequestration of IFN-γ on its receptor in vivo.

Figure 1D:
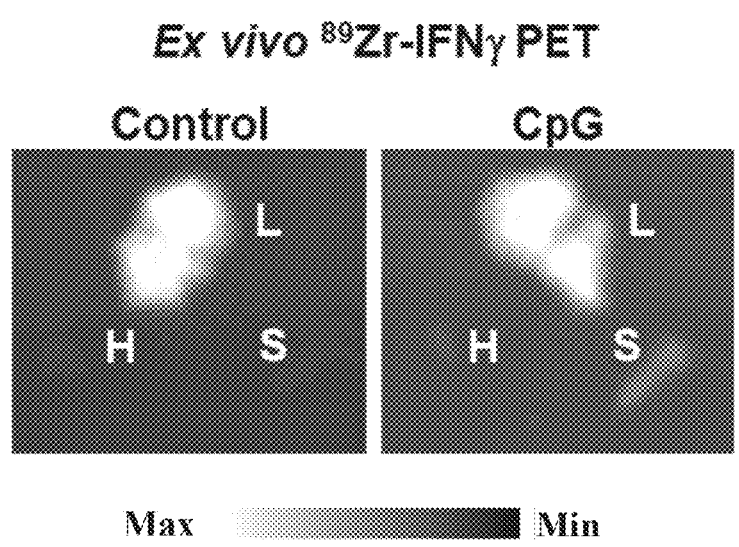
FIG. 1D is a pair of images showing liver (L), heart (H), and spleen (S) removed from mice used in the experiments described for FIG. 1C and imaged ex vivo.

As further verification of labeled-antibody conjugate uptake, the spleen, liver, heart and spleen tissues were removed and scanned ex vivo (FIG. 1D).

IFN-γ PET Detects Active Anti-Tumor Immunity In Situ in a Syngeneic Tumor Model

Figure 2A:
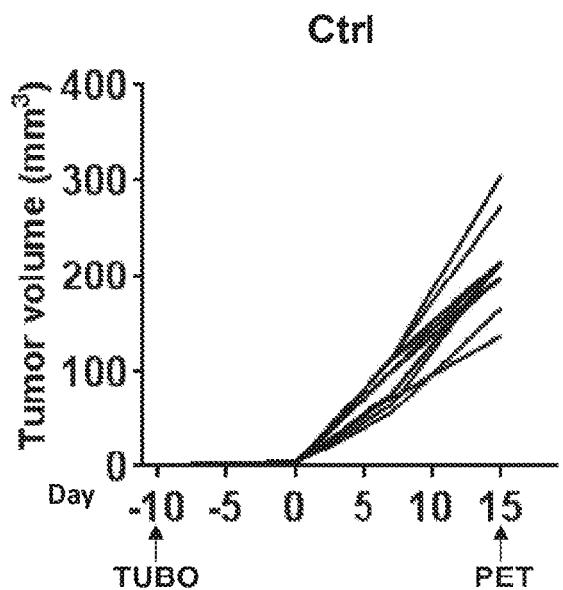
FIG. 2A is a graph showing results of Positron Emission Tomography (PET) evaluation of immunotherapy response in orthotopic TUBO mammary tumors by measurement of tumor volume of untreated control mice, Ctrl, n=11. TUBO cells were inoculated 10 days prior to the start of vaccinations, given on days 0 and 14. PET imaging was conducted on day 15 (Ctrl)
Figure 2B:
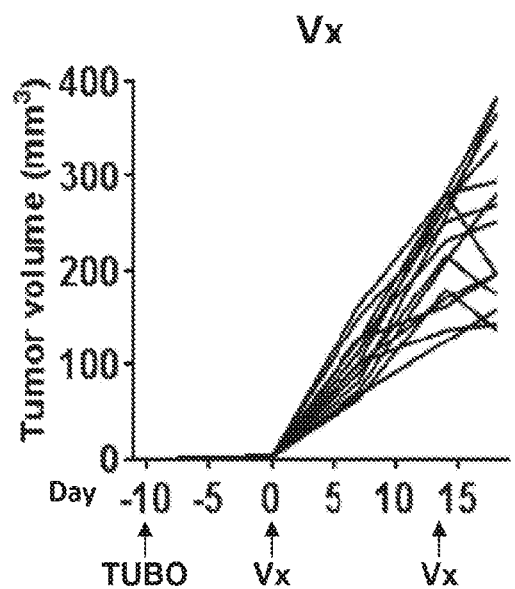
FIG. 2B is a graph showing results of PET evaluation of immunotherapy response in orthotopic TUBO mammary tumors by measurement of tumor volume of vaccinated mice, Vx, n=12. TUBO cells were inoculated 10 days prior to the start of vaccinations, given on days 0 and 14. PET imaging was conducted on day 21 (Vx)
Figure 9A:
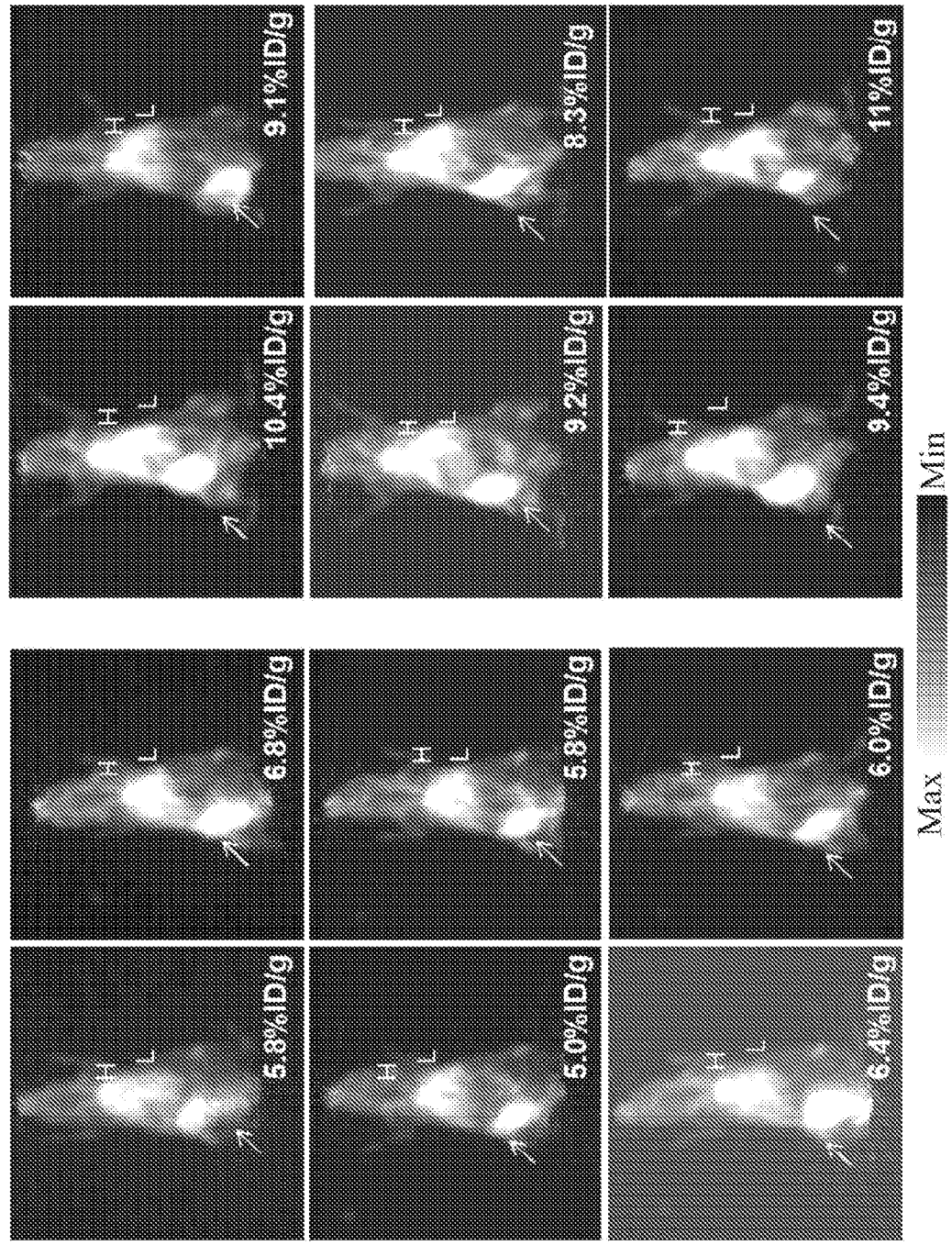
FIG. 9A shows MIP images of $^{89}$Zr-anti-IFNγ detection in all control (left) and vaccinated (right) TUBO bearing mice.

To test the capacity of $^{89}$Zr-anti-IFN-γ as a non-invasive measure of anti-tumor immune response, neu+ TUBO tumor bearing BALB/c mice were imaged after receiving two rounds of HER2/neu DNA vaccination as detailed in FIG. 2A and FIG. 2B. This vaccine induces HER2-specific humoral and T cell responses and ~10% equivalent of cross-reactive anti-neu T cells without cross-reactive neu-specific antibody. Tumor volumes began to stabilize or regress within 1 week after the second vaccination compared to untreated TUBO-bearing mice (FIG. 2A and FIG. 2B). Mice were injected with $^{89}$Zr-anti-IFN-γ labeled-antibody conjugate for PET imaging (FIG. 2C, FIG. 2D and FIG. 9A) at 72 h p.i. A nearly two-fold increase in tumor uptake was observed in vaccinated (Vx: 10.07±1.50% ID/g, n=6) versus control mice (Ctrl: 5.97±0.61% ID/g, n=6, p=0.0001). A $^{89}$Zr-labeled rat IgG isotype control labeled-antibody conjugate demonstrated similar tumor accumulation (72 h p.i.) in both untreated (5.27±0.79% ID/g) and vaccinated (5.93±0.85% ID/g) mice. This suggests baseline intratumoral IFN-γ levels are low without treatment. The notable low accumulation of the isotype control labeled-antibody conjugate after vaccination supports the specificity of the IFN-γ labeled-antibody conjugate and suggests increased $^{89}$Zr-anti-IFN-γ uptake is not simply due vascular permeability and retention effects post-ITx.

Detection of Tumor Infiltrating Lymphocytes Via CD3 immunoPET

Figure 2C:
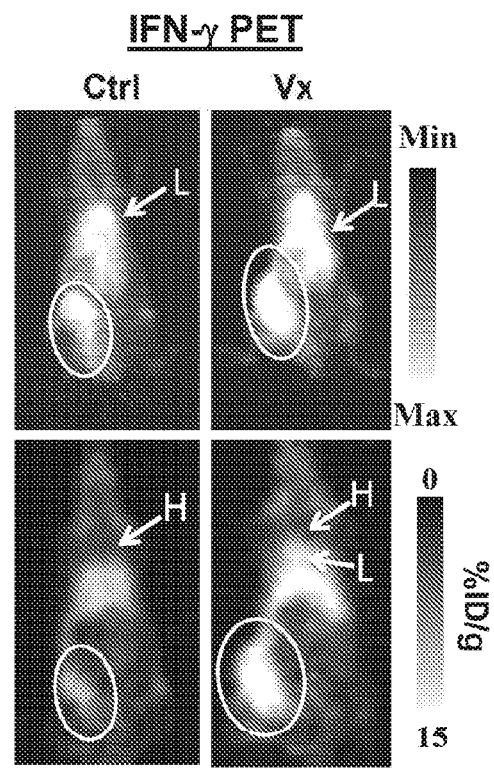
FIG. 2C shows representative whole body maximum intensity projections (MIP, top row) and planar (bottom row) images of control (Ctrl, left panels, n=6) and vaccinated (Vx, right panels, n=6) mice with $^{89}$Zr-anti-IFN-γ labeled-antibody conjugate. White circle=tumor, L=liver, H=heart.
Figure 2D:
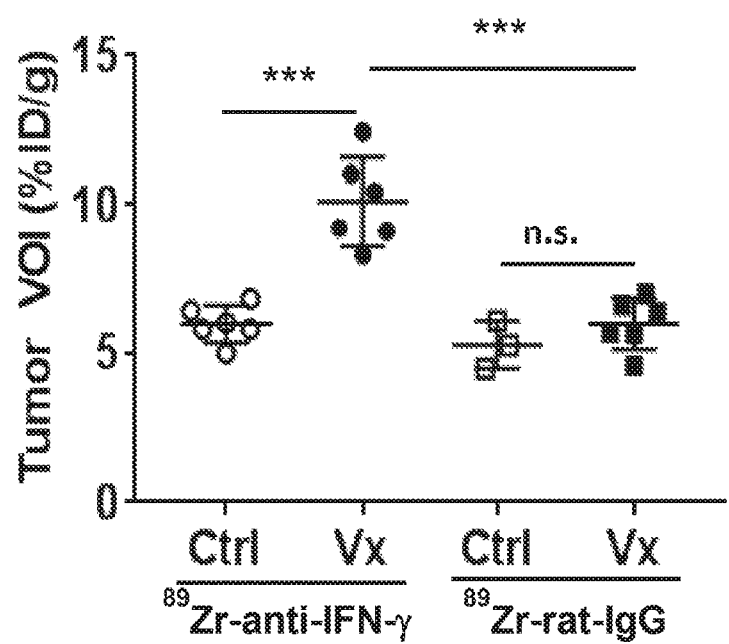
FIG. 2D is a graph showing tumor VOIs measured for each mouse from experiments described in FIG. 2C with a $^{89}$Zr-anti-IFN-γ labeled-antibody conjugate (left, n=6, untreated control; n=6, vaccinated control) or a $^{89}$Zr labeled rat IgG isotype control (right) included for each treatment group (n=3, untreated control; n=6, vaccinated control)
Figure 2E:
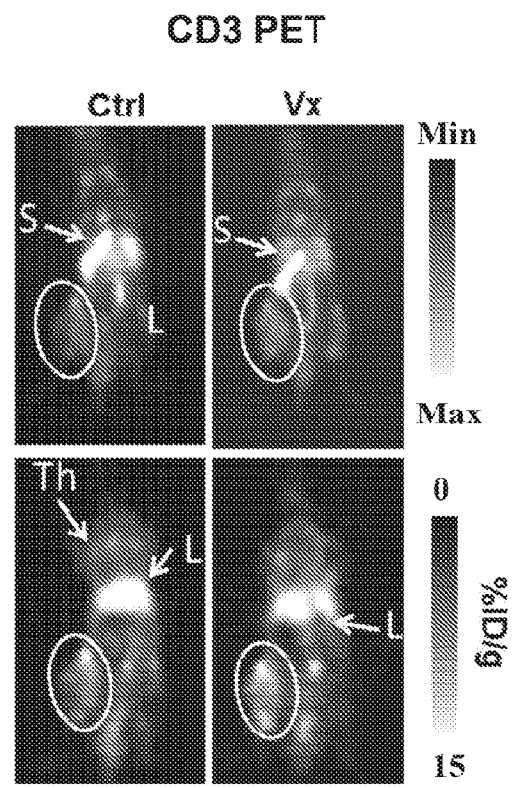
FIG. 2E shows representative MIP images (top panels) and planar sections (bottom panels) of $^{89}$Zr-anti-CD3 PET in control (left, n=5) and vaccinated mice (middle, n=6). White circle=tumor, L=liver, S=spleen, Th=Thymus.
Figure 2F:
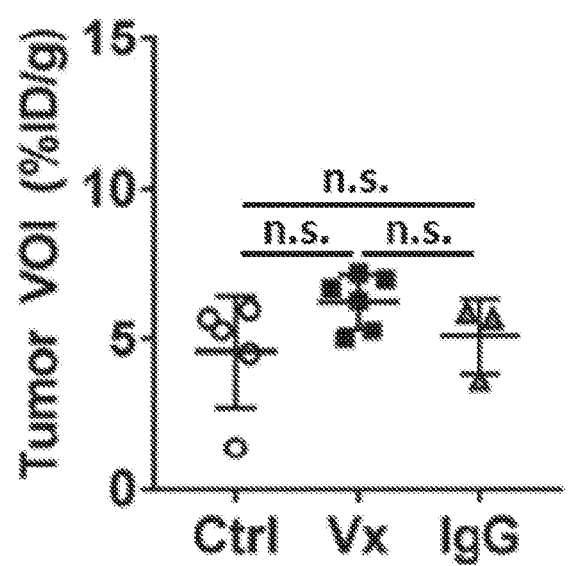
FIG. 2F is a graph showing tumor VOIs measured for each mouse from experiments described in FIG. 2E (Ctrl, Vx, left (n=5) and middle (n=6)) and including results from a non-specific $^{89}$Zr labeled Armenian hamster IgG isotype control was used to measure tumor VOI in a separate group of untreated mice (IgG, right, n=3)
Figure 9B:
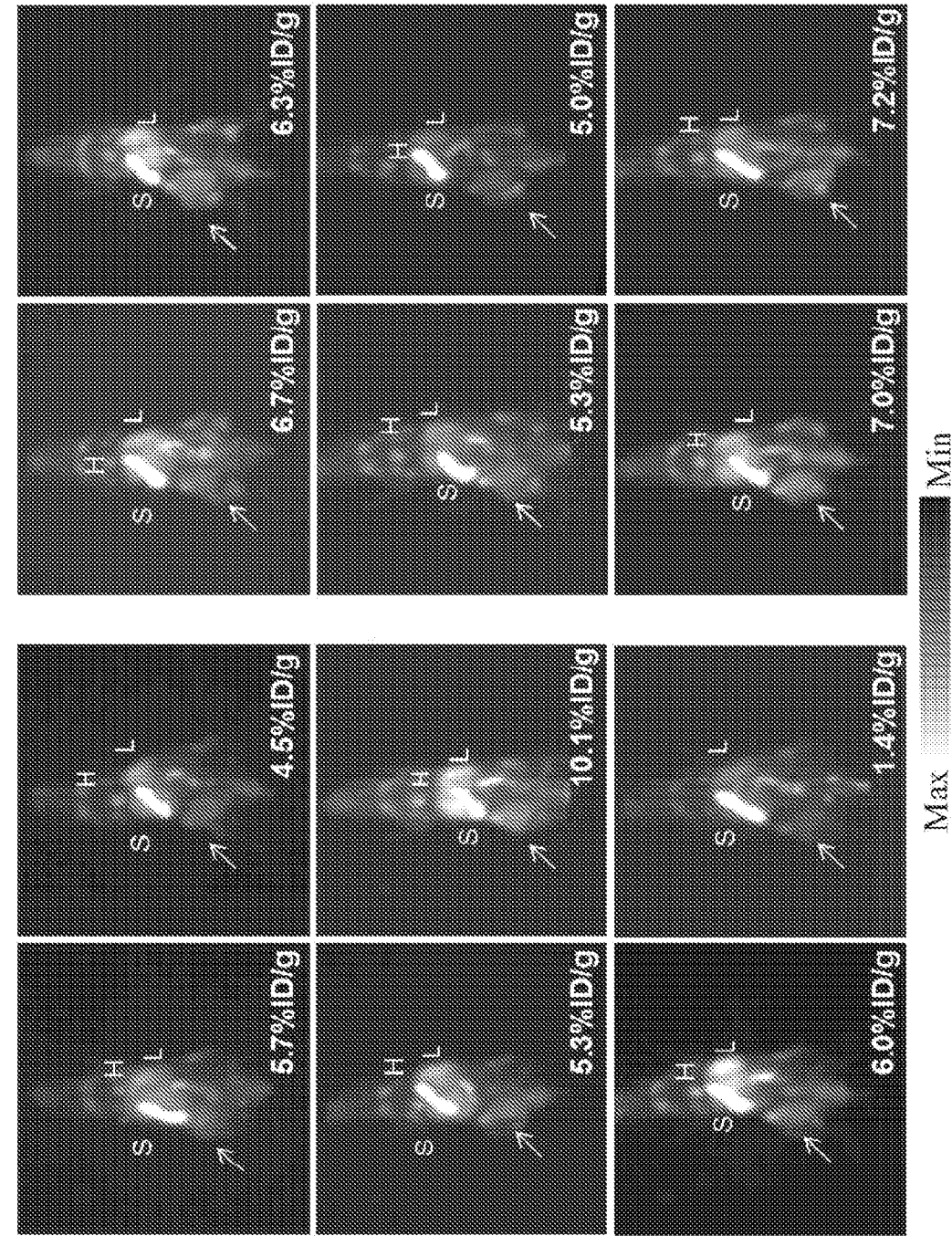
FIG. 9B shows MIP images of $^{89}$Zr-anti-CD3 detection in all control (left) and vaccinated (right) TUBO bearing mice.
Figure 10A:
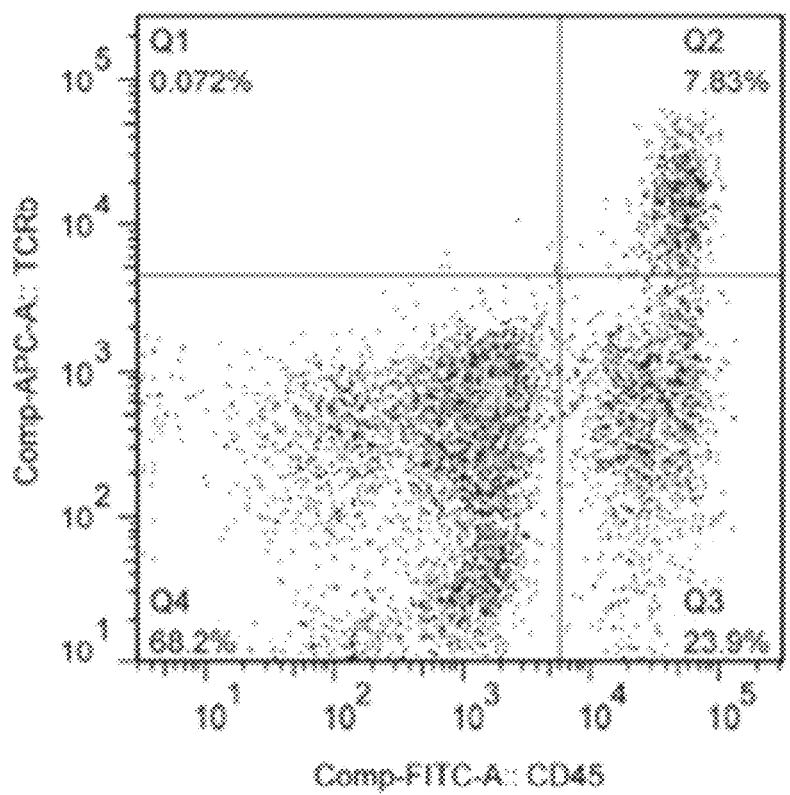
FIG. 10A is a plot of flow cytometry results showing T cell detection in TUBO-bearing BALB/c mice. Tumors from untreated TUBO-bearing mice were dissociated and stained with CD45, to detect total leukocyte infiltrates, and the T cell receptor beta chain (TCRβ), to identify the T cell fraction, by flow cytometry.
Figure 10B:
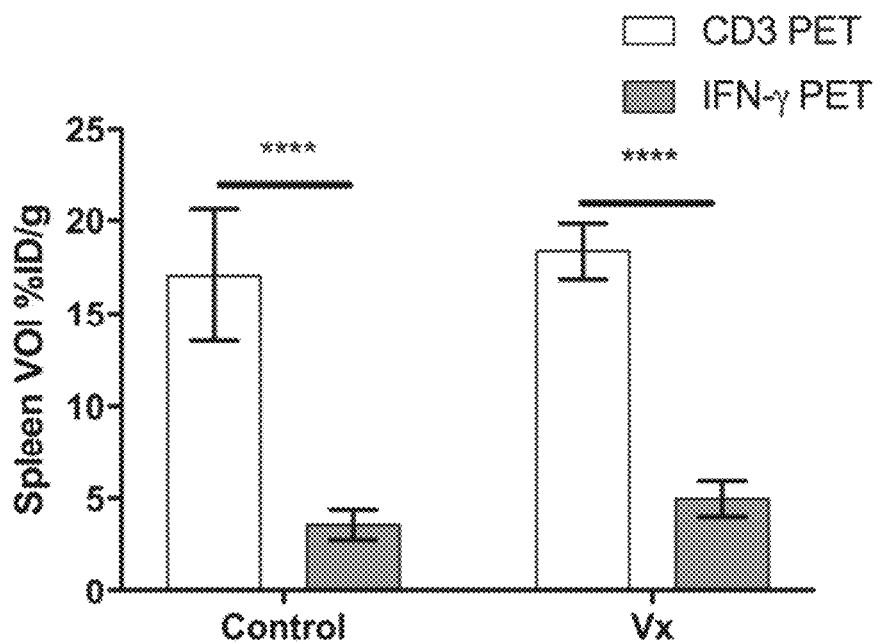
FIG. 10B is a graph showing Spleen VOIs calculated for each TUBO-bearing mouse imaged with either $^{89}$Zr-anti-IFNγ or $^{89}$Zr-anti-CD3.

Total T cell presence in the tumor microenvironment was assessed in separate groups of mice via immunoPET imaging of CD3+ tumor infiltrating lymphocytes using $^{89}$Zr-anti-CD3 (FIG. 2E, FIG. 2F, and FIG. 9B). Vaccinated tumors exhibited a modest, insignificant increase of CD3 labeled-antibody conjugate binding compared to control (6.25±0.37% ID/g, n=6 vs. 4.58±0.83% ID/g, n=5, p=0.16). Both cohorts failed to demonstrate a significant change in uptake compared to Armenian hamster isotype control IgG (5.90±1.26% ID/g, n=3, p=0.87 (Ctrl), p=0.49 (Vx)). Untreated TUBO tumors have endogenous T cell infiltrates as detected by flow cytometry upon dissociation (FIG. 10A). However, CD3 immunoPET suboptimally detected these TILs in both untreated and vaccinated mice with measured VOIs similar to the non-specific IgG tumor accumulation. This may be due to excessive uptake by the spleen, a T cell-homing secondary lymphoid tissue (Ctrl: 17.06±3.56% ID/g, Vx: 18.36±1.49% ID/g, FIG. 10B), which can act as a labeled-antibody conjugate "sink." In contrast, limited splenic accumulation was observed with the IFN-γ PET probe (Ctrl: 3.58±0.81% ID/g, p<0.0001, Vx: 4.97±0.97% ID/g, p<0.0001).

Ex Vivo Validation Via IHC, qPCR, and ELISA

Figure 3A:
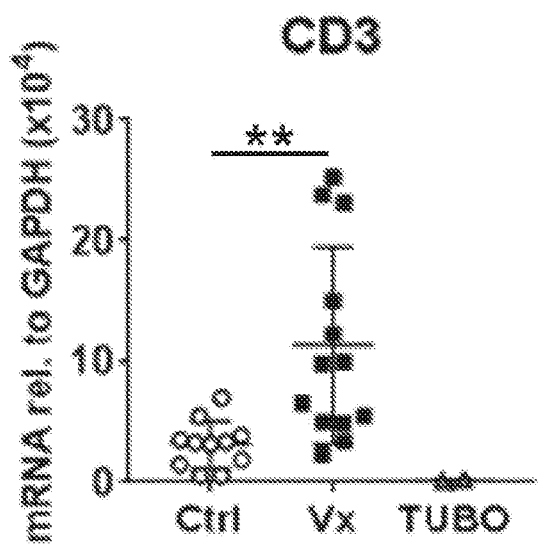
FIG. 3A is a graph showing results of mRNA analysis of TUBO mammary tumors removed after imaging. For this, total RNA was obtained from Ctrl (n=11) and Vx (n=13) tumor tissue analyzed by qPCR with primers specific to CD3. Cultured TUBO cells serve as control (n=2)
Figure 3B:
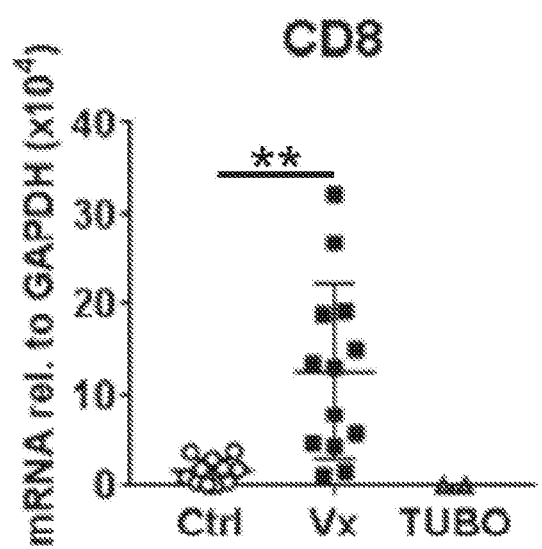
FIG. 3B is a graph showing results of mRNA analysis of TUBO mammary tumors removed after imaging. For this, total RNA was obtained from Ctrl (n=11) and Vx (n=13) tumor tissue a analyzed by qPCR with primers specific to CD8. Cultured TUBO cells serve as control (n=2)
Figure 3C:
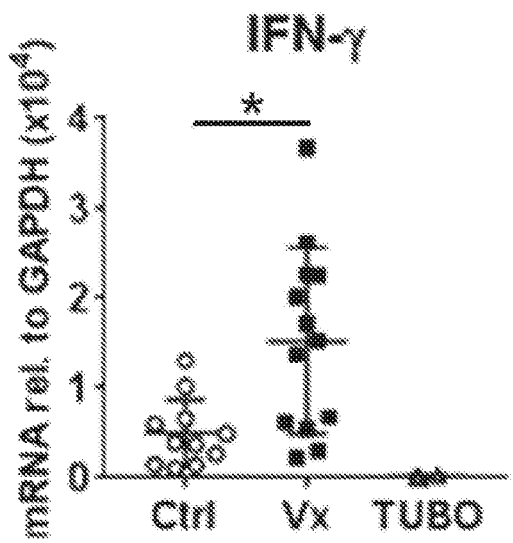
FIG. 3C is a graph showing results of mRNA analysis of TUBO mammary tumors removed after imaging. For this, total RNA was obtained from Ctrl (n=11) and Vx (n=13) tumor tissue a analyzed by qPCR with primers specific to IFN-γ. Cultured TUBO cells serve as control (n=2)
Figure 3D:
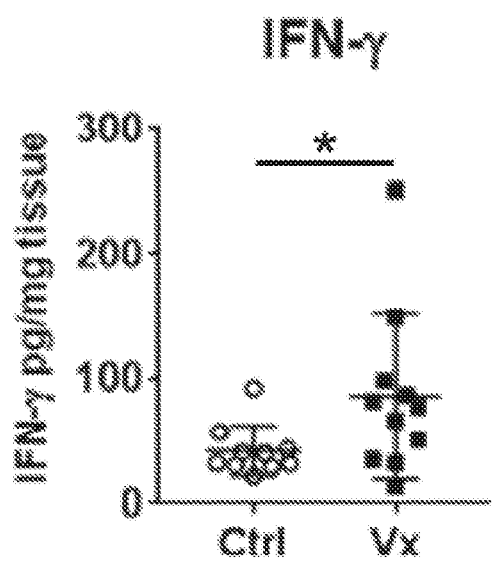
FIG. 3D is a graph showing results of an IFN-γ ELISA conducted with protein lysates of TUBO tumor segments of control Ctrl (n=10) and Vx (n=11) mice.
Figure 11A:
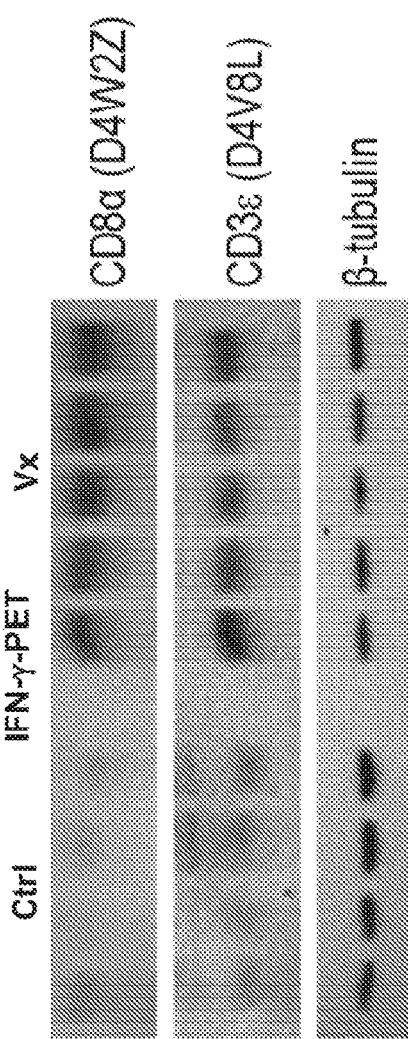
FIG. 11A shows an image demonstrating immunoblot detection of T cell markers in imaged TUBO-bearing mice. Western blots from lysed decayed tumor tissues post-IFN-γ PET were conducted to analyze presence of CD3 and CD8 protein in the Vx vs Ctrl mice. Beta-tubulin is detected as a gel loading control.
Figure 11B:
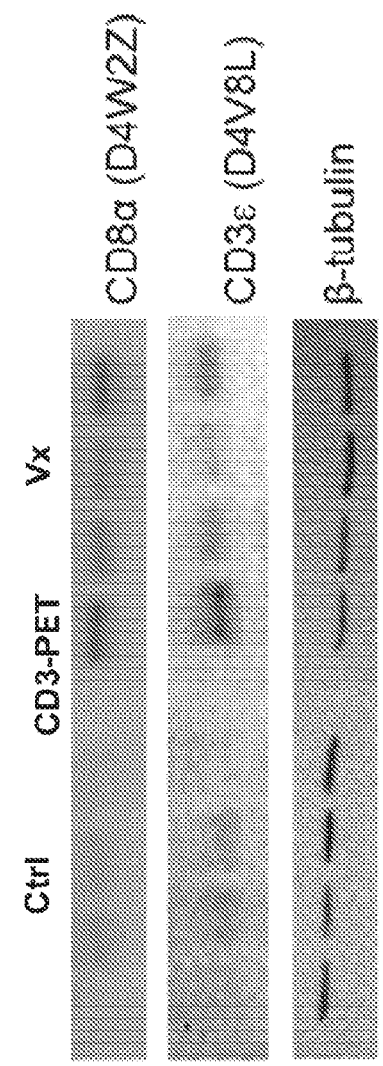
FIG. 11B shows an image demonstrating immunoblot detection of T cell markers in imaged TUBO-bearing mice. Western blots from lysed decayed tumor tissues post-CD3 PET were conducted to analyze presence of CD3 and CD8 protein in the Vx vs Ctrl mice. Beta-tubulin is detected as a gel loading control.

Upon completion of imaging, tissues were collected for ex vivo validation. Tumor tissue was assessed to verify CD3+ and CD8$^+$ T cell presence, as well as expression of IFN-γ. Transcripts levels of CD3, CD8 and IFN-γ were increased in tumor tissue after vaccination (FIG. 3A, FIG. 3B, FIG. 3C, respectively, Ctrl: n=11, Vx: n=13), in concordance with the PET imaging data. Cultured TUBO cell cDNA is included as a negative control. CD3 and CD8 proteins were increased after treatment (FIG. 11A and FIG. 111B) and intratumoral IFN-γ protein was also confirmed and quantitated by ELISA (FIG. 3D). ELISA results showed higher total IFN-γ in Vx (n=11) versus Ctrl (n=10) TUBO tumors (85.37±65.89 vs. 41.69±20.12 µg/mg tissue, p=0.043).

Figure 3E:
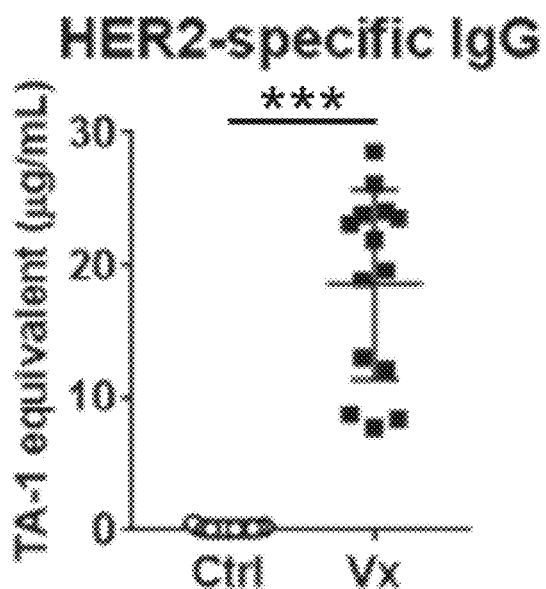
FIG. 3E is a graph showing results of measurement of HER2-specific IgG in serum of TUBO-bearing mice by flow cytometry (Ctrl: n=13, Vx: n=14)
Figure 3F:
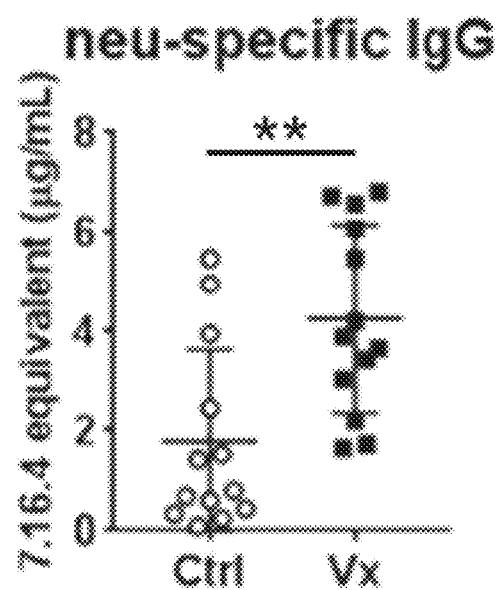
FIG. 3F is a graph showing results of measurement of neu-specific IgG in serum of TUBO-bearing mice by flow cytometry (Ctrl: n=13, Vx: n=14)
Figure 3G:
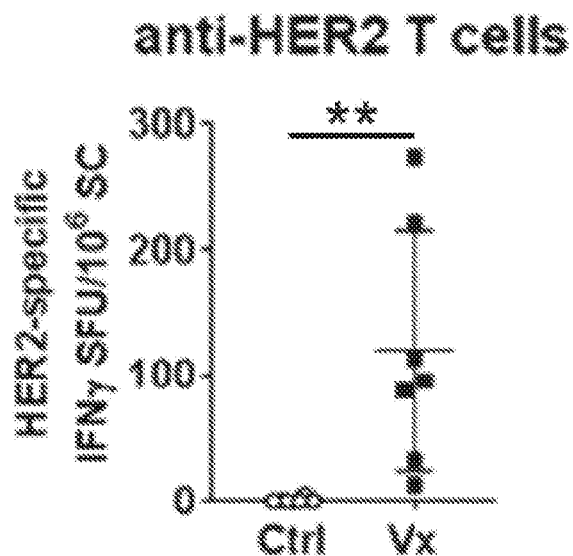
FIG. 3G is a graph showing results of measurement of HER2-responsive T cells by IFN-γ ELISPOT (Ctrl: n=6, Vx: n=7)
Figure 3H:
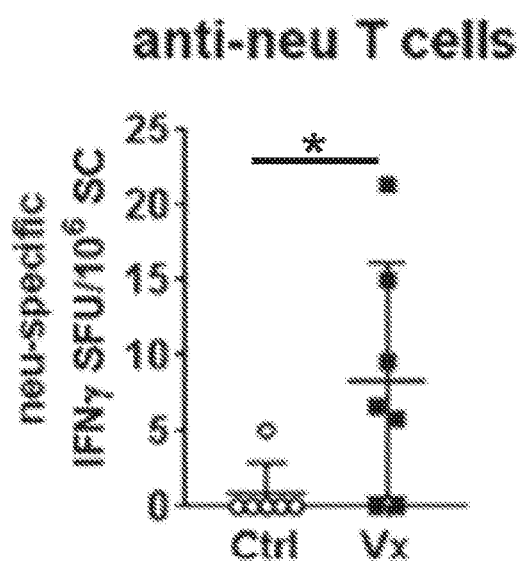
FIG. 3H is a graph showing results of measurement of neu-responsive T cells by IFN-γ ELISPOT (Ctrl: n=6, Vx: n=7)

Peripheral vaccine-induced immunity was measured by HER2/neu-specific serum IgG (FIG. 3E and FIG. 3F) and splenic T cell responses (FIG. 3G and FIG. 3H). HER2-specific IgG was only detected in vaccinated mice (18.68±7.40 µg/mL, n=14, p<0.0001). TUBO tumors constitutively express the cell surface oncogene neu, which is foreign in wild-type BALB/c mice. Neu-specific IgG is detected in unvaccinated control TUBO-bearing mice (1.58±1.60 µg/mL, n=13), which is further increased in vaccinated animals (6.18±7.34 µg/mL, n=14, p=0.0019). While the HER2 DNA vaccine itself does not induce anti-neu IgG, tumor cell killing likely enhances immune activity to this foreign antigen. Detection of HER2-specific IFN-γ-producing T cells was restricted to vaccinated mice, similar to anti-HER2 IgG (119.40±95.18/10$^6$ splenocytes (SC), n=7, vs. 0.83±2.04/10$^6$ SC in untreated controls, n=6, p=0.0012). Peripheral anti-neu T cells were detected in all vaccinated animals (8.33±7.75/10$^6$ SC) while only 1 of 4 untreated controls showed T cell responsiveness to neu (0.83±2.04/10$^6$ SC, p=0.033). The absolute quantities of HER2 and neu-specific IgG and T cells were ~10-fold lower than similarly vaccinated non-tumor-bearing mice. This may be due to tumor-associated immune suppression by myeloid-derived suppressor cells or regulatory T cells (Tregs), which are reportedly increased in TUBO-bearing mice.

Detection of ITx Response in a Spontaneous Tumor Model

Figure 4A:
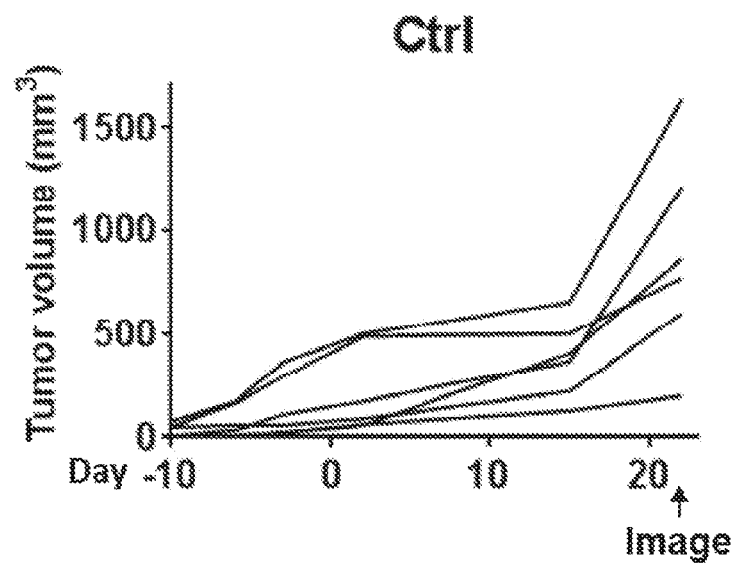
FIG. 4A is a graph showing results of PET detection of anti-tumor immunity in spontaneous tumor-bearing NeuT mice in which control, untreated mice (Ctrl, n=6) were imaged by PET after palpable tumors were permitted to grow 31 days.
Figure 4B:
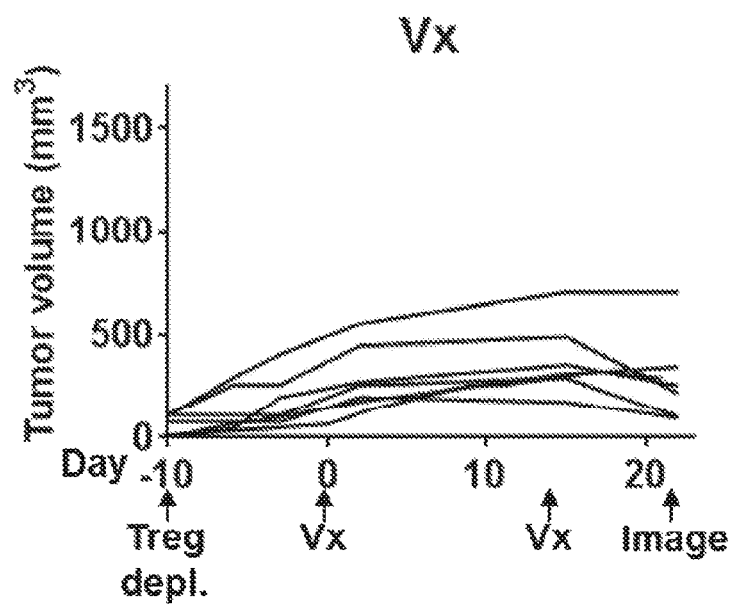
FIG. 4B is a graph showing results of PET detection of anti-tumor immunity in spontaneous tumor-bearing vaccinated NeuT mice (Vx, n=7), which, upon detection of palpable spontaneous salivary tumors, regulatory T cells (Treg) were depleted 10 d prior to the first vaccination. These mice received two HER2/neu DNA vaccinations 14 d apart. PET imaging was conducted 7 days after the final vaccination.
Figure 4C:
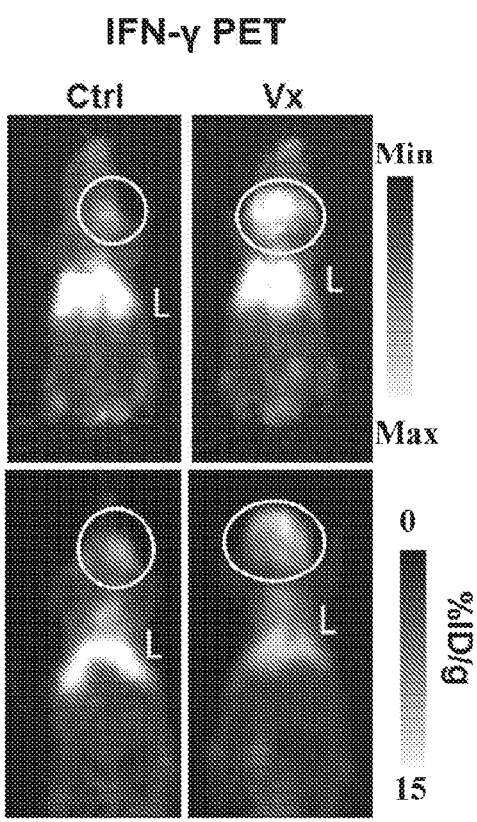
FIG. 4C shows representative whole body maximum intensity projections (MIP, top row) and planar (bottom row) images of control (left panels, n=3) and HER2/neu DNA-vaccinated (right panels, n=4) NeuT mice with $^{89}$Zr-anti-IFN-γ PET labeled-antibody conjugate. White circle=tumor, L=liver.
Figure 4D:
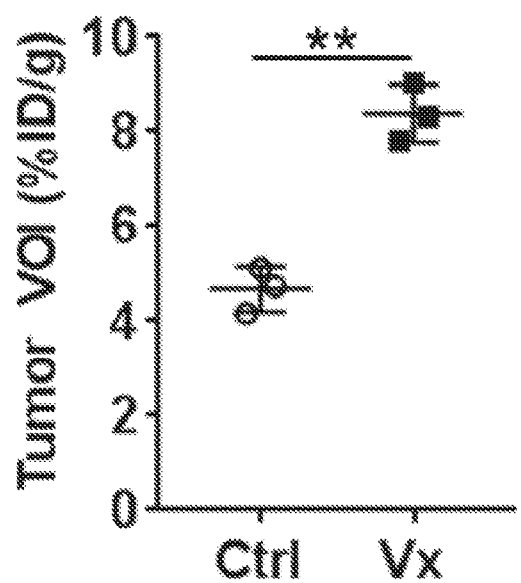
FIG. 4D is a graph showing tumor VOIs were calculated for each mouse studied for the experiment described in FIG. 4C.
Figure 4E:
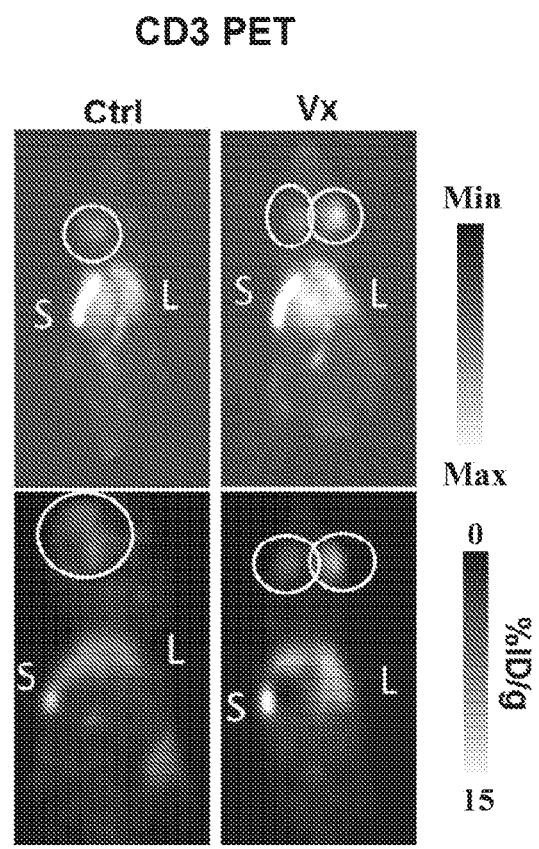
FIG. 4E shows representative whole body maximum intensity projections (MIP, top row) and planar (bottom row) images of control (left panels, n=3) and HER2/neu DNA-vaccinated (right panels, n=4) NeuT mice with CD3 PET labeled-antibody conjugate. White circle=tumor, L=liver, S=spleen.
Figure 4F:
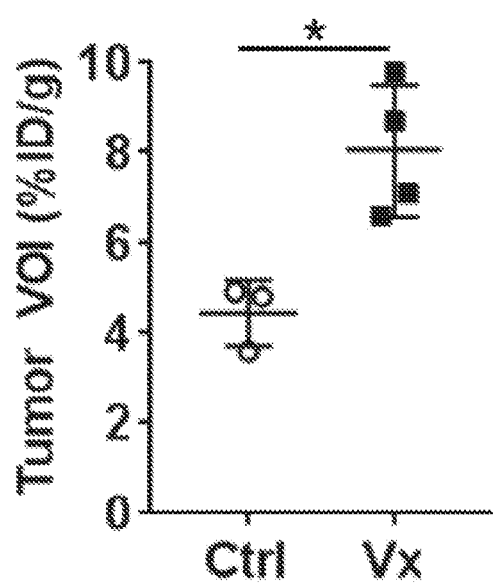
FIG. 4F is a graph showing tumor VOIs were calculated for each mouse studied for the experiment described in FIG. 4E.
Figure 12A:
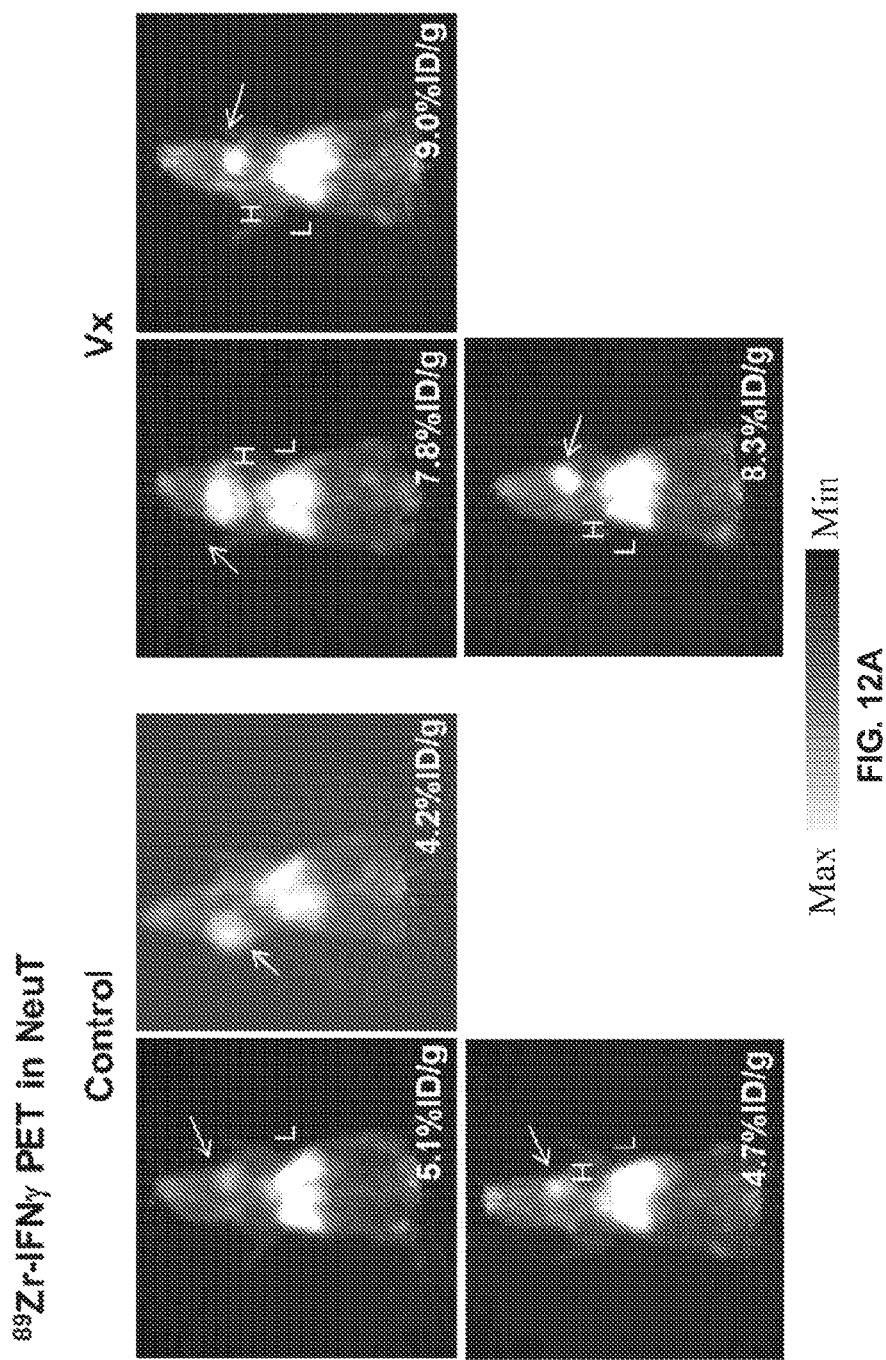
FIG. 12A shows MIP images of $^{89}$Zr-anti-IFNγ detection in all control (left) and vaccinated (right) NeuT mice bearing spontaneous salivary tumors.
Figure 12B:
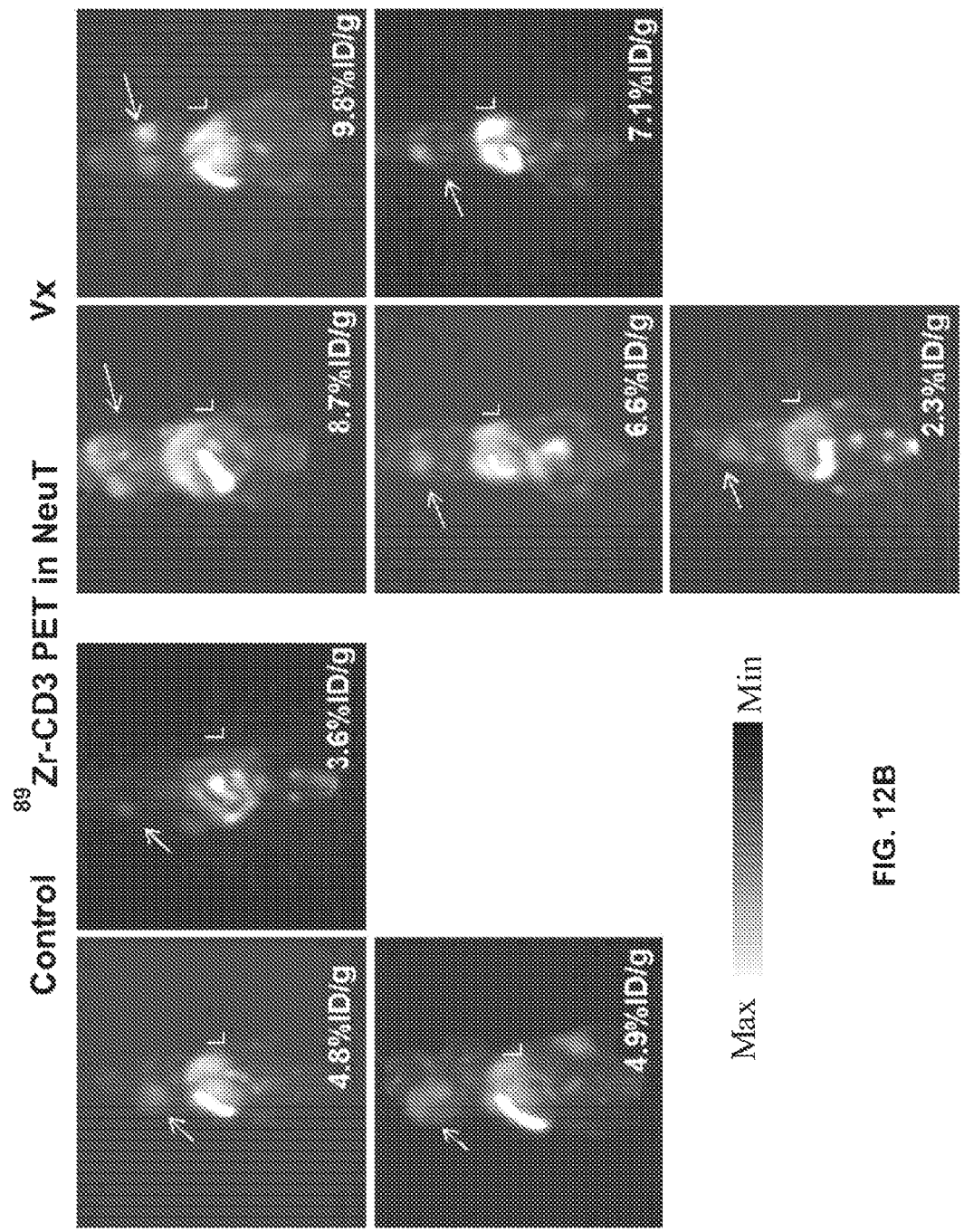
FIG. 12B shows MIP images of $^{89}$Zr-anti-CD3 detection in all control (left) and vaccinated (right) NeuT mice bearing spontaneous salivary tumors.

In this example, the capacity of IFN-γ PET imaging to detect anti-tumor immune activity in a spontaneous tumor setting was tested. Neu transgenic (NeuT) mice are engineered to express a transforming rat neu under direction of the mouse mammary tumor virus promoter, allowing immune system recognition of neu as a self-antigen. Male NeuT mice, which develop 1-2 spontaneous neu+ salivary tumors between 30-40 weeks of age, were used. Once tumors were palpable, Tregs were depleted using anti-CD25 mAb clone PC61 to enhance ITx response given NeuT mice are immune tolerant to rat neu, followed by two HER2/neu DNA vaccinations as detailed in FIGS. 4A and 4B. Vaccination of NeuT mice (n=7) controlled tumor growth rate compared to untreated (n=6) tumor-bearing NeuT mice (FIG. 4A and FIG. 4B, p=0.032). IFN-γ PET of vaccinated tumors displayed a nearly two-fold higher uptake of $^{89}$Zr-anti-IFN-γ (8.37±0.35% ID/g, n=4) vs. control (4.63±0.47% ID/g, n=3, p=0.001), indicating infiltration of functional anti-tumor T cells (FIG. 4C, FIG. 4D, and FIG. 12A). An examination of tumor infiltrates via CD3 PET (FIG. 4E, FIG. 4F, and FIG. 12B) revealed a similar trend (8.05±1.47% ID/g vs. 4.43±0.72% ID/g, n=3 per group, p=0.012).

Figure 5A:
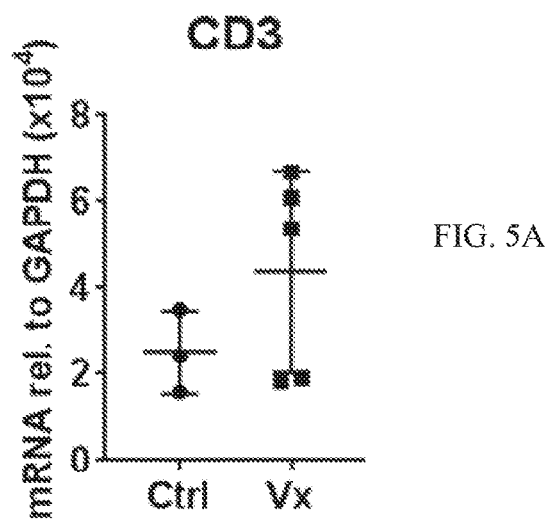
FIG. 5A is a graph showing results of mRNA analysis of spontaneous tumors from NeuT mice removed after imaging. For this, total RNA was obtained from Ctrl (n=3) and Vx (n=3) tumor tissue and analyzed by qPCR with primers specific to CD3.
Figure 5B:
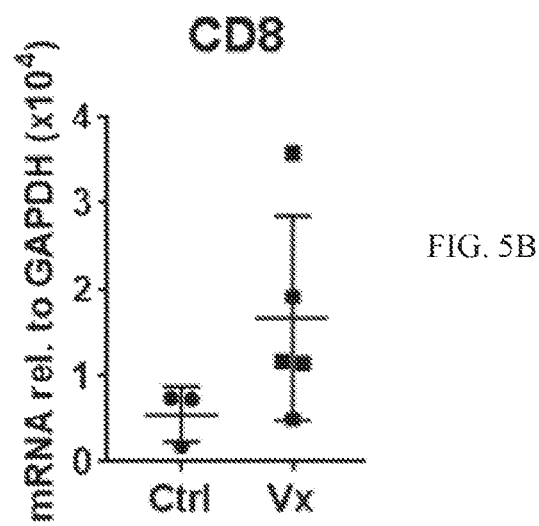
FIG. 5B is a graph showing results of mRNA analysis of spontaneous tumors from NeuT mice removed after imaging. For this, total RNA was obtained from Ctrl (n=3) and Vx (n=3) tumor tissue and analyzed by qPCR with primers specific to CD8.
Figure 5C:
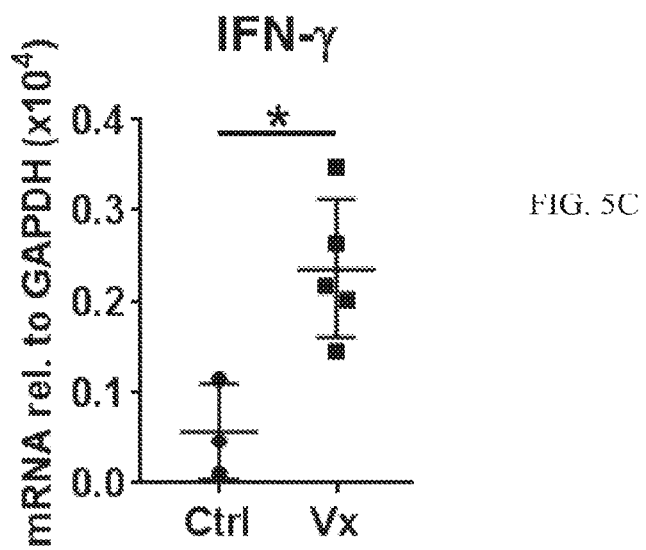
FIG. 5C is a graph showing results of mRNA analysis of spontaneous tumors from NeuT mice after imaging. For this, total RNA was obtained from Ctrl (n n=3) and Vx (n=3) tumor tissue and analyzed by qPCR with primers specific to IFN-γ.
Figure 5D:
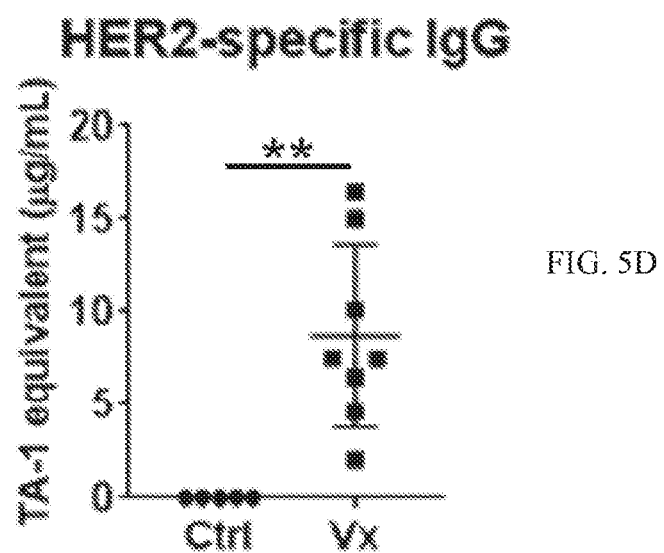
FIG. 5D is a graph showing results of measurement of HER2-specific IgG in serum of NeuT mice by flow cytometry (Ctrl: n=5, Vx: n=8)
Figure 5E:
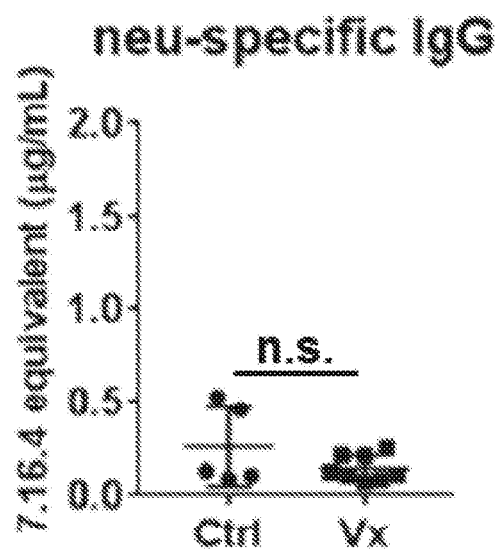
FIG. 5E is a graph showing results of measurement of neu-specific IgG in serum of NeuT mice by flow cytometry (Ctrl: n=5, Vx: n=8)
Figure 5F:
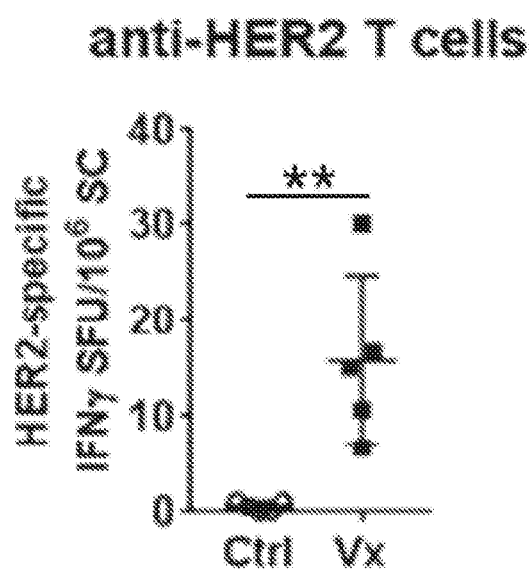
FIG. 5F is a graph showing results of measurement of HER2-responsive T cells of NeuT mice by IFN-γ ELISPOT (Ctrl: n=5, Vx: n=5)
Figure 5G:
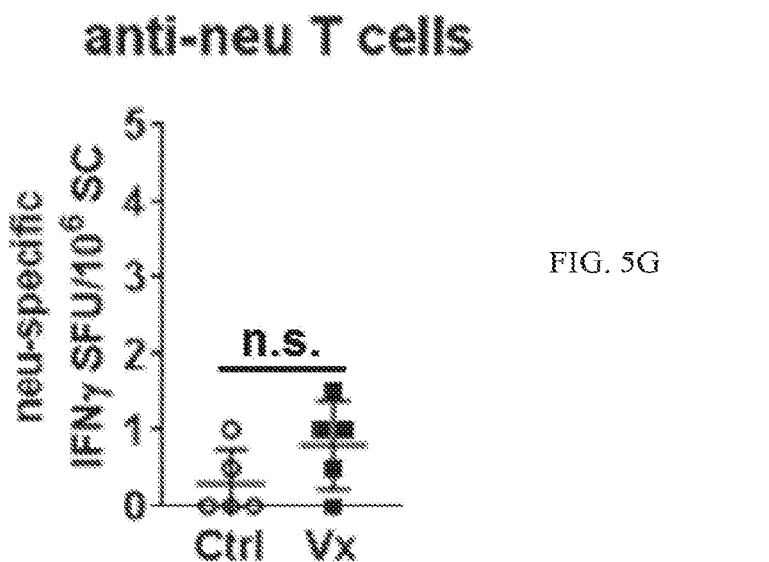
FIG. 5G is a graph showing results of measurement of neu-responsive T cells of NeuT mice by IFN-γ ELISPOT (Ctrl: n=5, Vx: n=5)

Validation of T cell infiltration and IFN-γ production was conducted by qPCR in tumor tissue samples (FIG. 5A, FIG. 5B, and FIG. 5C). CD3 and CD8 detection showed a variable modest, insignificant increase after vaccination, while IFN-γ mRNA increased (Ctrl: n=3, Vx: n=5, p=0.036). Peripheral immune response to the vaccine was evaluated by measuring serum anti-HER2 and anti-neu IgG as well as spleen-resident HER2- and neu-responsive IFN-γ-producing T cells. Tolerance to HER2/neu in NeuT mice was apparent with a comparatively lower ITx response vs. wild-type BALB/c mice bearing TUBO tumors in FIG. 2. HER2-specific IgG was detected in vaccinated animals (FIG. 5D, FIG. 5E, 8.7±4.9 μg/mL, n=8, p=0.0016 vs. Ctrl, n=5), while anti-neu IgG was negligible or absent in all samples tested. Despite increased intratumoral detection of IFN-γ in vaccinated NeuT mice by PET, peripheral T cell response to neu was low (FIG. 5F, FIG. 5G, 15.80±8.84/$10^6$ SC, n=5) with HER2 vaccination, and was not significantly increased relative to untreated control (n=5, p=0.27). T cell response to the cognate vaccine antigen was evident in anti-HER2 T cells (15.80±8.84/$10^6$ SC, n=5, p=0.0079). The ratio of anti-neu to anti-HER2 T cells detected was ~5.1% in NeuT mice, which is two-fold lower relative to that detected in non-immune tolerant BALB/c mice bearing TUBO (10.0%, FIG. 3G and FIG. 3H). These results support the hypothesis that peripheral immune monitoring may be an inadequate measure of anti-tumor immunity with tumor-responsive T cells preferentially localizing within the tumor, demonstrating the utility of in situ analysis methods using PET imaging of anti-IFN-γ.

IFN-γ PET Imaging is an Indicator of Immune Activation Status In Situ

Figure 6A:
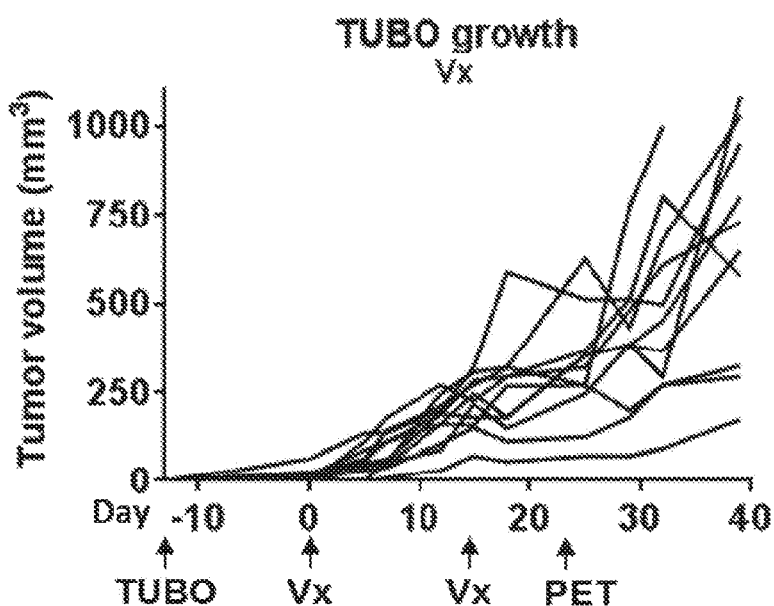
FIG. 6A is a graph showing tumor volume in TUBO-bearing vaccinated BALB/c mice (n=11). TUBO cells were inoculated 13 days prior to the start of vaccinations, to allow for variability in tumor volumes at treatment onset. Vaccines were given on days 0 and 14. PET imaging was conducted on day 28.
Figure 6B:
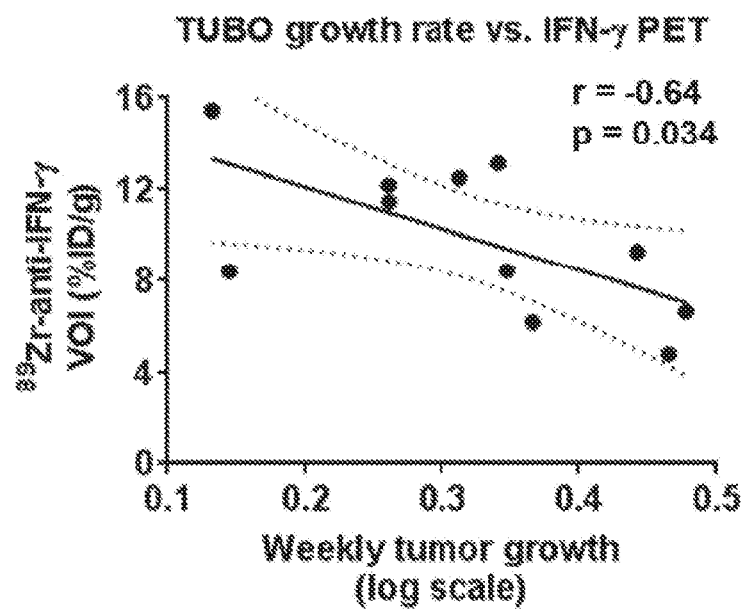
FIG. 6B is a graph showing weekly tumor growth rate, calculated by regression analysis of log tumor growth, versus $^{89}$Zr-anti-IFN-γ labeled-antibody conjugate uptake plotted for each mouse and evaluated by Pearson's correlation.
Figure 13:
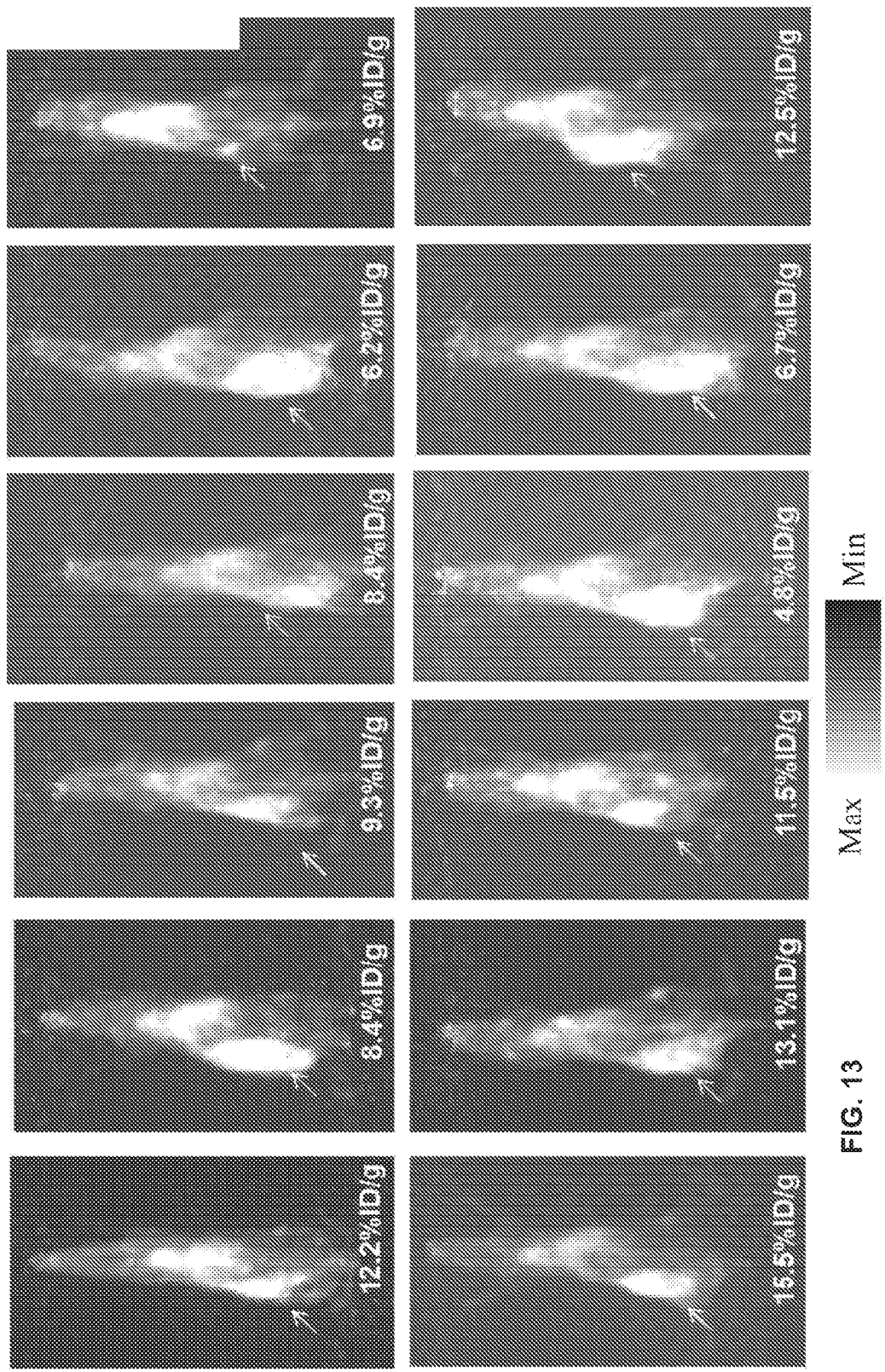
FIG. 13 shows $^{89}$Zr-IFN-γ PET of vaccinated mice for correlation to tumor growth. The MIP images show $^{89}$Zr-anti-IFNγ detection in all vaccinated TUBO mice bearing tumors.
Figure 14A:
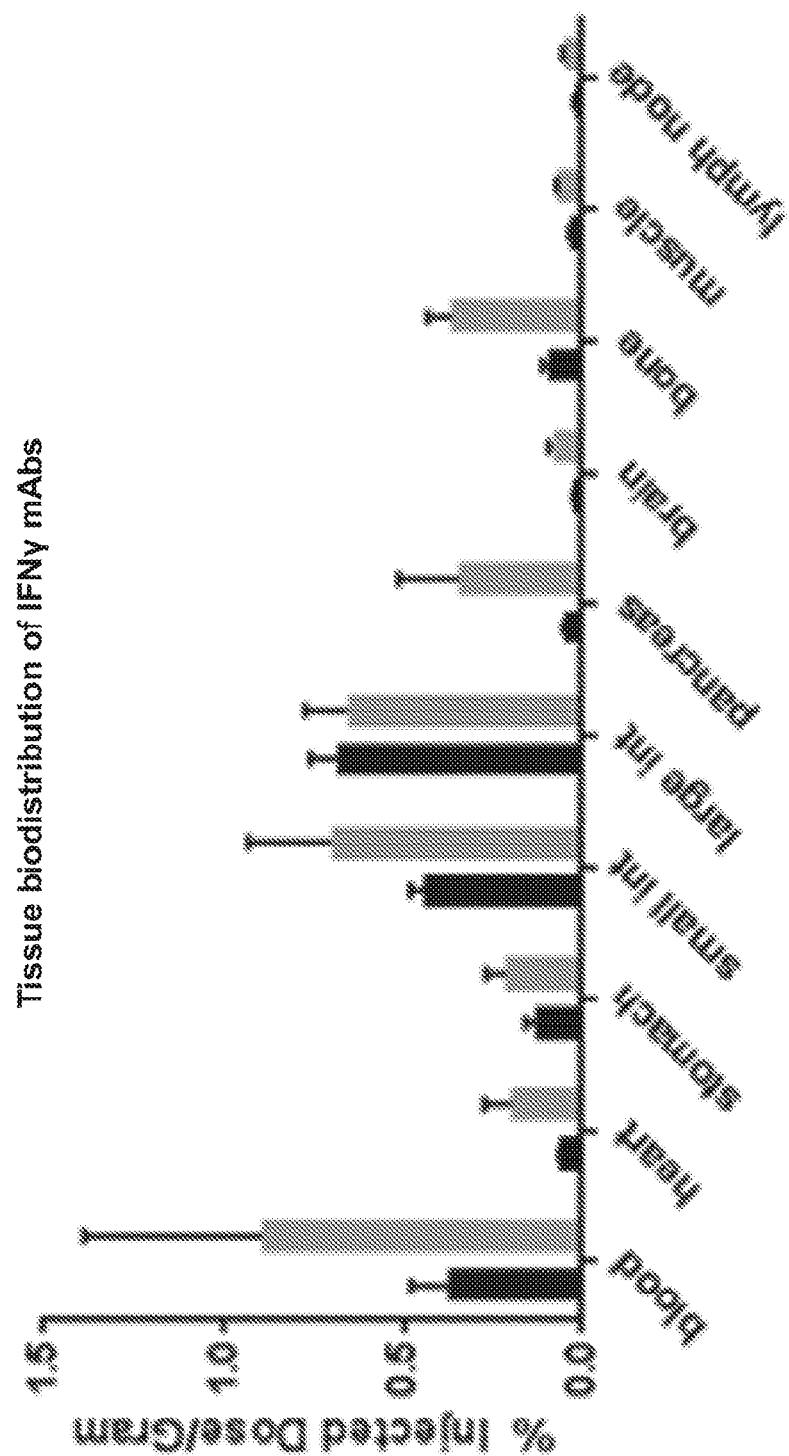
FIG. 14A is a graph showing tissue biodistribution of anti-IFN-γ PET labeled-antibody conjugate. BALB/c mice were treated with 100 μg CpG intramuscular and co-injected with $^{89}$Zr-IFN-γ intravenous (mAb clone AN-18 or XMG1.2). Uptake in blood, heart, stomach, small intestine, large intestine, pancreas, brain, bone, muscle, and lymph node was analyzed by gamma counter 72 hours later.
Figure 14B:
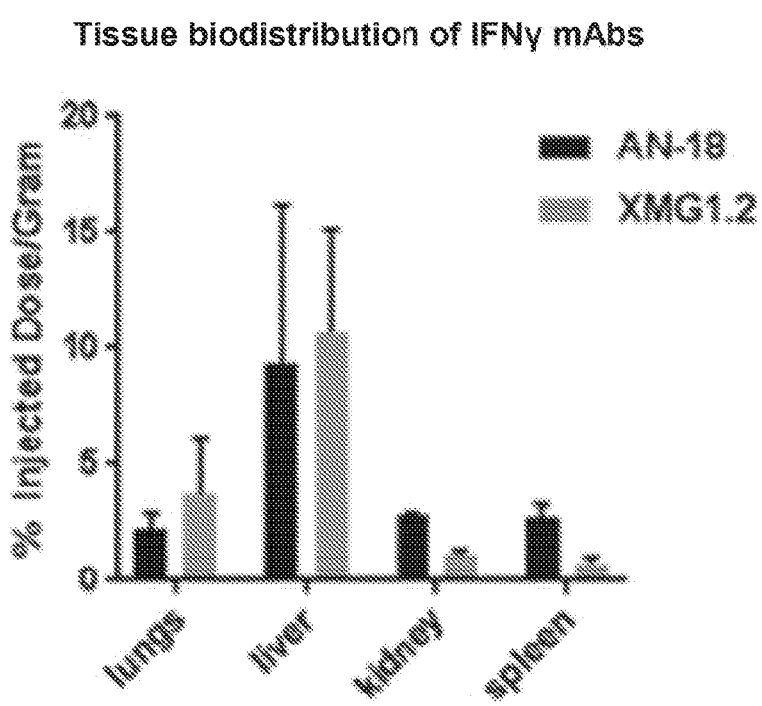
FIG. 14B is a graph showing tissue biodistribution of anti-IFN-γ PET labeled-antibody conjugates. BALB/c mice were treated with 100 μg CpG intramuscular and co-injected with $^{89}$Zr-IFN-γ intravenous (mAb clone AN-18 or XMG1.2). Uptake in lungs, liver, kidney, and spleen, was analyzed by gamma counter 72 hours later.

To test the capacity of $^{89}$Zr-anti-IFN-γ to predict treatment outcomes, BALB/c mice (n=11) bearing variably-sized TUBO tumors were treated with HER2 vaccine, resulting in a range of growth slopes (FIG. 6A). $^{89}$Zr-anti-IFN-γ PET imaging was conducted two weeks after the final vaccination and tumor volume was monitored for an additional ten days. Tumor-localized $^{89}$Zr-anti-IFN-γ labeled-antibody conjugate uptake inversely correlated with tumor growth rate (FIG. 6B and FIG. 13, r=−0.64, 95% CI. (−0.90,−0.06); p=0.034), suggesting IFN-γ PET is an indicator of the effects of ITx on these tumors.

Figure 6C:
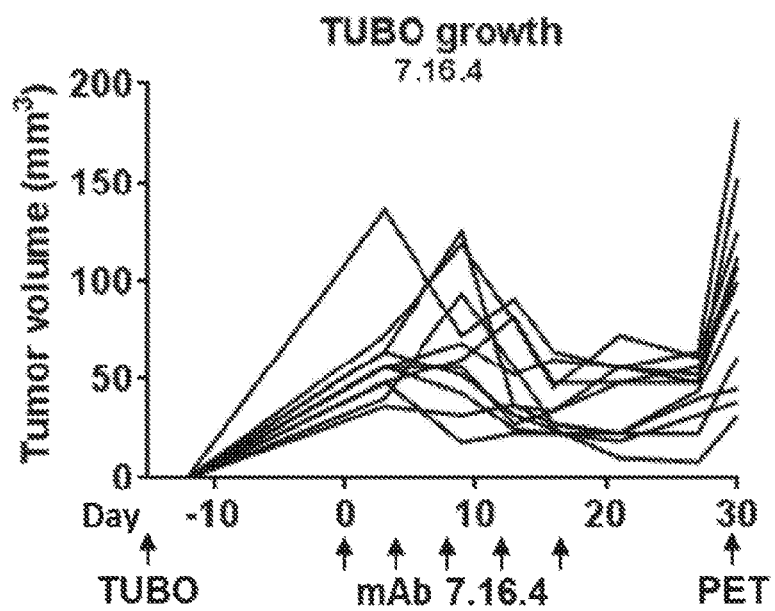
FIG. 6C is a graph showing tumor growth during passive immunotherapy with anti-neu mAb 7.16.4, given as 5 doses at 1.5 mg i.p. every 3-4 days as indicated beginning 15 days after tumor inoculation. $^{89}$Zr-anti-IFN-γ (n=5) or $^{89}$Zr-rat-IgG control (n=6) PET imaging was conducted 30 days after treatment onset.
Figure 6D:
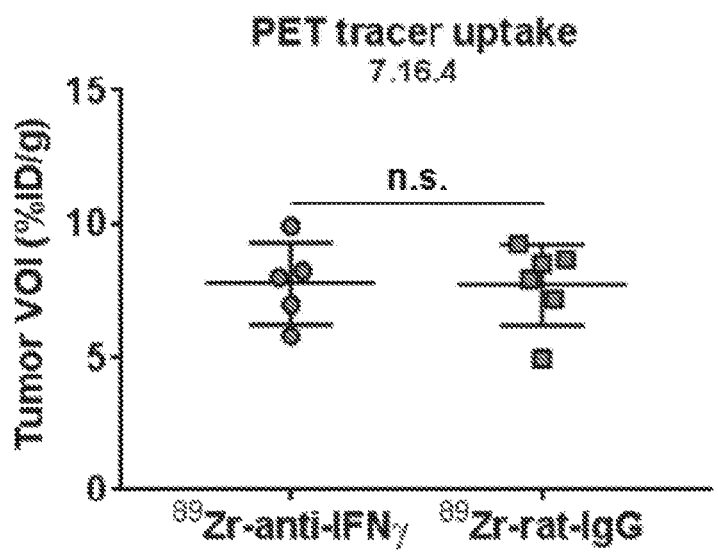
FIG. 6D is a graph showing tumor VOIs calculated for $^{89}$Zr-anti-IFN-γ or $^{89}$Zr-rat-IgG labeled-antibody conjugate in 7.16.4 treated TUBO-bearing mice.

IFN-γ PET was then evaluated in a setting where tumor-infiltrating T cells are present but have become exhausted. TUBO-bearing mice were treated with passive ITx, mAb 7.16.4 to rat neu. This mAb has been shown to inhibit neu signaling in addition to initiating host anti-tumor immunity. Once tumors were established at ~50 mm$^3$, 1 mg doses of 7.16.4 were given i.p. at 3-4 day intervals for a total of 5 treatments, which reduced and stabilized tumor growth (FIG. 6C). $^{89}$Zr-anti-IFN-γ (n=5) or control IgG (n=6) PET imaging was conducted on day 30 after treatment onset, at which time tumor growth had resumed. Tumor uptake of IFN-γ labeled-antibody conjugate was indistinguishable from IgG control, suggesting a lack of immune activity (FIG. 6D). CD8 T cell infiltration was evaluated by IHC, see Table 2 below.

TABLE 2

| Treatment | Avg # CD8 | Std. Dev. |
| --- | --- | --- |
| Ctrl | 3 | 1 |
| mAb 7.16.4 | 36 | 19 |
| Vx | 74 | 25 |

Blinded pathologist enumeration of the three regions with highest infiltration were calculated, showing a 12-fold increase in CD8 T cells after 7.16.4 treatment versus control (Ctrl: 3±1, 7.16.4: 36±19). Vaccinated TUBO tumor had the largest detected CD8 infiltration (74±25). Overall, CD8$^+$ tumor infiltration was intermittent, with high-density regions scattered among areas with no detectable CD8$^+$ TILs.

Figure 6E:
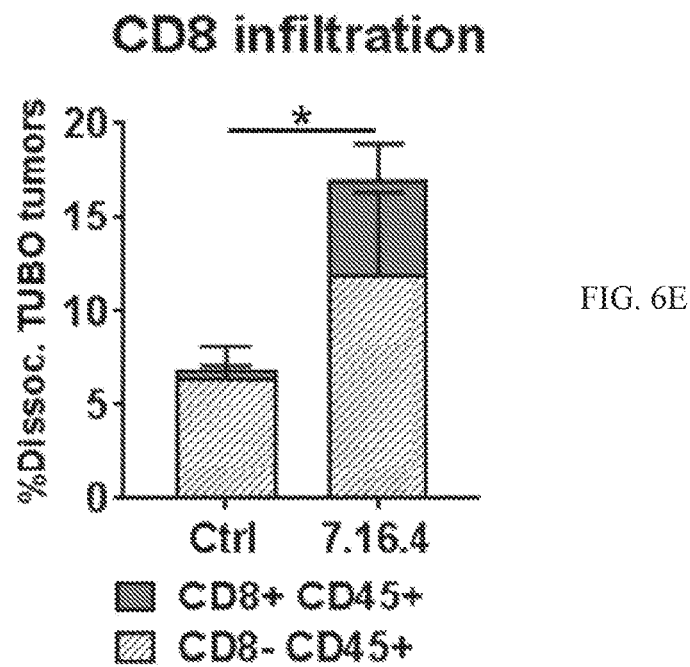
FIG. 6E is a graph showing results relating to control and 7.16.4-treated tumors (n=4 each) which were dissociated and analyzed for T cell infiltration by flow cytometry by staining for CD45 and CD8.
Figure 6F:
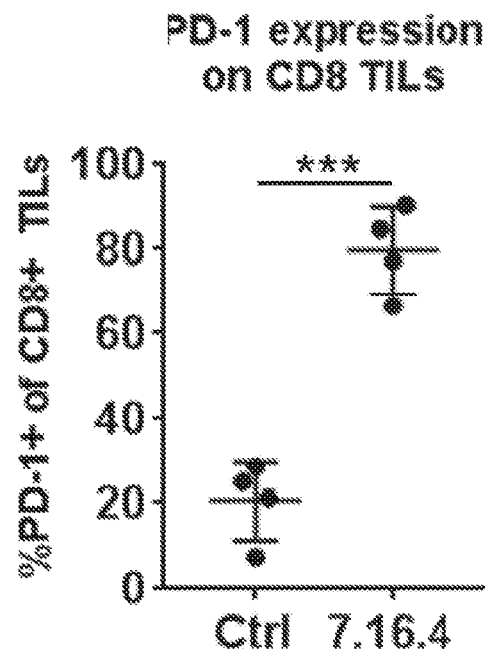
FIG. 6F is a graph showing PD-1 expression analyzed by flow cytometry on CD8+ tumor infiltrates from (FIG. 6F)
Figure 7A:
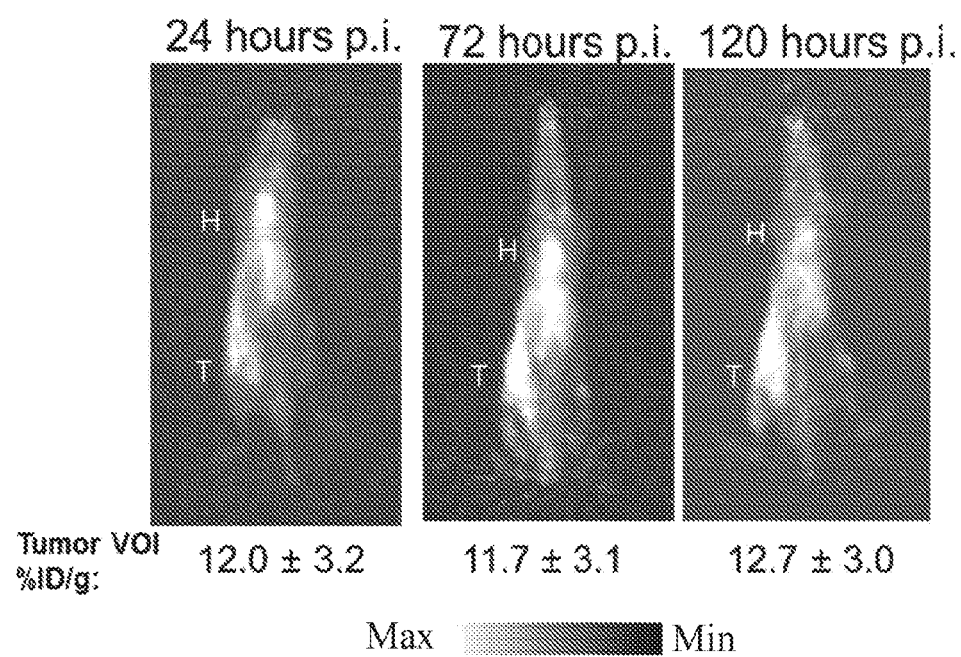
FIG. 7A shows time course imaging of $^{89}$Zr-anti-IFNγ. Mice were injected with $^{89}$Zr-anti-IFNγ and images of MIP are shown for each time point. L=liver, S=spleen.
Figure 7B:
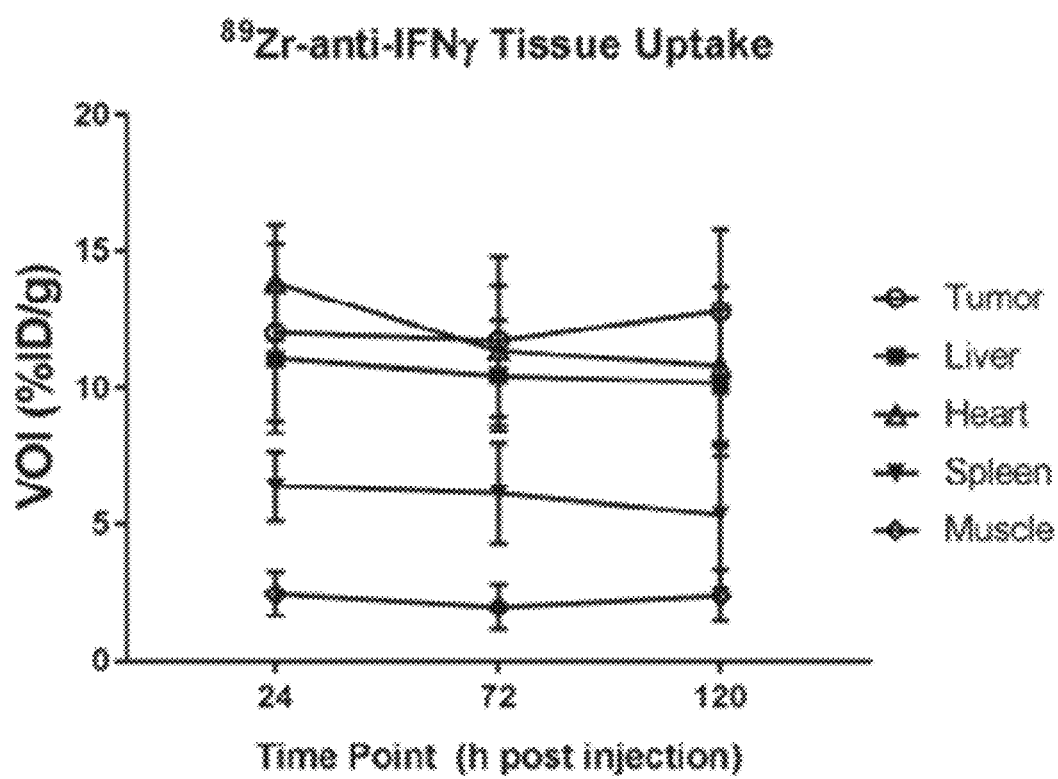
FIG. 7B is a graph of the volumes-of-interest obtained from select tissues over time from 24-120 h p.i.
Figure 8A:
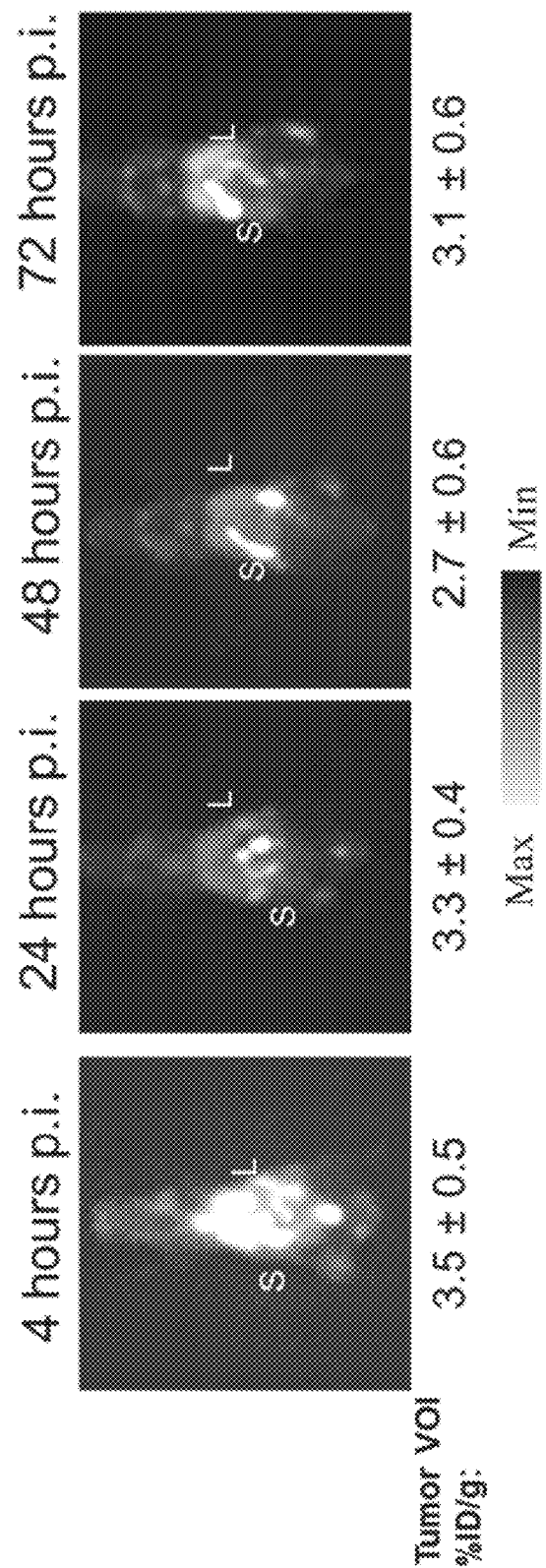
FIG. 8A shows time course imaging of $^{89}$Zr-anti-CD3. Mice were injected with $^{89}$Zr-anti-CD3 and images of MIP are shown for each time point. L=liver, S=spleen.
Figure 8B:
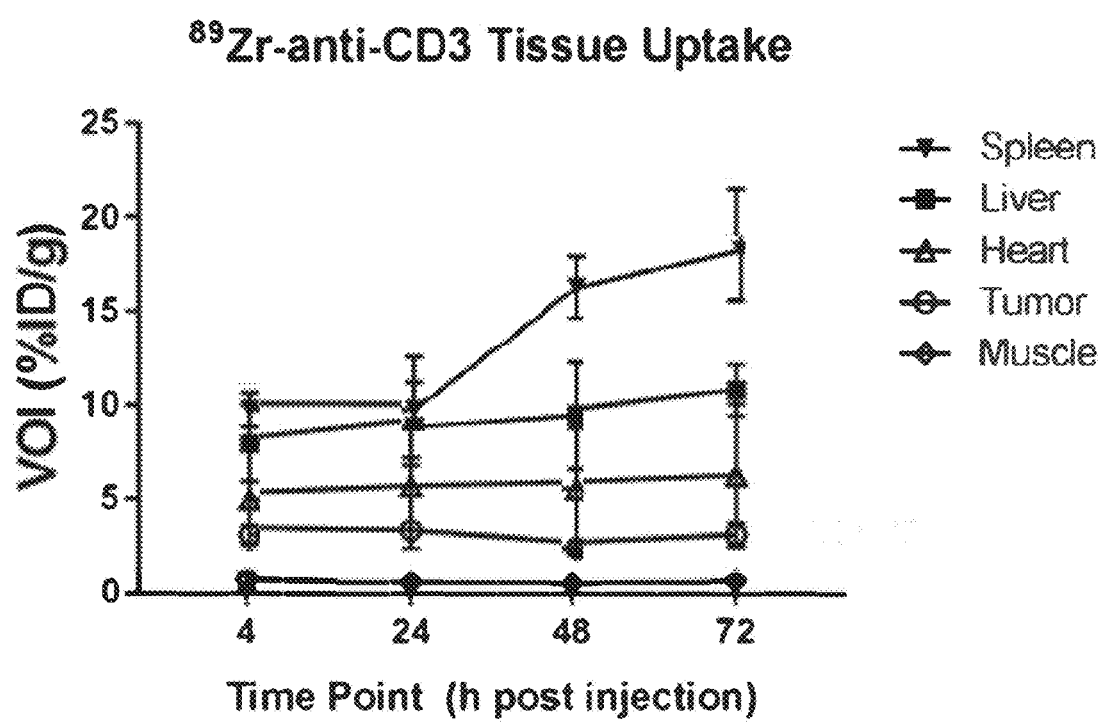
FIG. 8B is a graph of the volumes-of-interest obtained from select tissues over time from 4-72 h p.i.

CD8 T cell infiltration after 7.16.4 therapy was validated by flow cytometry in a parallel cohort of treated and control mice (FIG. 6E, n=4 each). An overall increase in CD45+ infiltrates (Ctrl: 6.84±1.85%, 7.16.4: 16.95±5.88%, p=0.036) and CD8+ T cells (Ctrl: 0.41±0.19%, 7.16.4: 4.96±1.96%, p=0.018) was detected after mAb treatment. The majority of CD8+ TTLs expressed the T cell exhaustion marker PD-1 (FIG. 6F, 79.7±10.3%) compared to control tumors (20.5±9.3%, p=0.0001). Collectively these results suggest this treatment model promotes an inactive and exhausted CD8 T cell status despite tumor infiltration, leading to reduced IFN-γ production which can be detected by $^{89}$Zr-anti-IFN-γ PET imaging.

To date, a variety of monoclonal antibodies have been commercially developed against mouse and human IFN-γ. For the studies presented here, anti-mouse IFN-γ clone AN-18 was utilized, and clone XMG1.2 was also tested in a biodistribution study. BALB/c mice were treated with a single intramuscular injection of 100 μg CpG-ODN and tissue biodistribution was measured after 72 h. From these results, it is not anticipated that the clone of IFN-γ antibody would significantly impact its efficacy as a PET labeled-antibody conjugate.

IFN-γ Diabody Production

From the derived sequence of the anti-IFNγ (clone: AN18), homodimers of the single chain Fv were produced using CHO cells as expression system (Neoclone, LLC). Octet analysis of the binding affinity (Kd) for the diabody was 37.9±5.5 nM vs. 28.2±0.66 nM for the full-length AN18.

Synthesis and Quality Control of immunoPET Probes

NOTA-PEG4-Tz was made (57±12% yield) by attaching NOTA-Bz-NCS to tetrazine (Tz)-PEG4-NH2 using equimolar ratios in DMSO/TEA solvent for 1 h at room temperature (RT). Purification was done through Cis RP-HPLC. $^{18}$F-labeling proceeded using $^{18}$F-AlF-NOTA method. Briefly, non-carrier added $^{18}$F[F$^-$] will be incubated with 40 nmol AlCl$_3$ in 0.4 M KHCO$_3$ at pH~4 for 10 min. Equimolar NOTA-PEG4-Tz in 3:1 acetonitrile:H$_2$O was added and the solution was incubated for 15 minutes at 90° C. Analytical radio-C18 HPLC monitored the reaction. Purification of $^{18}$F-AlF-NOTA-Tz was made by eluting the product through a C$_{18}$-Solid Phase Extraction cartridge with ethanol. Radiochemical Yield: 14-16% decay-corrected.

Diabody (db) Conjugation to $^{18}$F-AlF-NOTA-Tz

Figure 15:
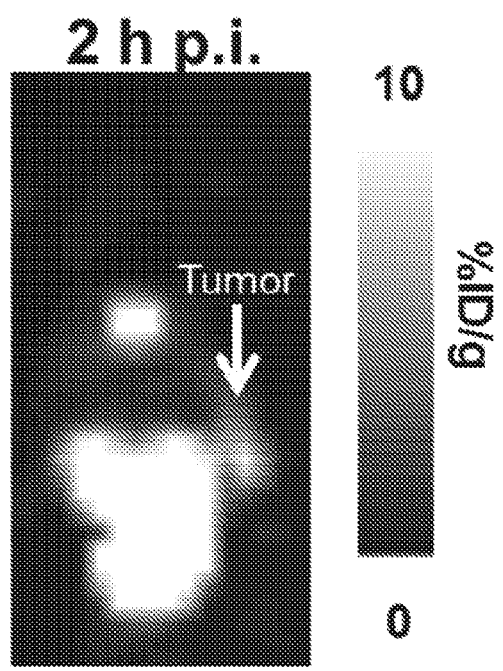
FIG. 15 is an image showing results of injection of 100-150 μCi anti-IFN-γ PET labeled-diabody conjugate into a TUBO-bearing BALB/c mouse after Vx.

Labeling of Dbs (MW: ~50 kDa, NeoClone, WI) is accomplished via inverse electron demand Diels-Alder bioorthogonal click reaction using Tz and transcyclooctene (TCO), which affords a rapid, mild method of labeling a protein, conserving its configuration. The db fragment of anti-IFNγ clone AN18 was attached to TCO-NHS, which was then conjugated to $^{18}$F-AlF-NOTA-Tz at RT in PBS, pH ~ 7 for 15 min. The labeled product was purified through a spin column (MWCO: 10 kDa). Radio-instant thin layer chromatography and size exclusion chromatography (SEC) indicated >95% purities with an overall decay-corrected radiochemical yield of 6-10%. The specific activity was 3.8-4 mCi/mg. 100-150 μCi db tracer was injected into a TUBO-bearing BALB/c mouse after Vx (FIG. 15). Tumor uptake is detected with an ROI of ~8.0% ID/g at 3 h p.i., similar to results obtained with full-length mAb (FIG. 2C). The clearance appears to be through the gall bladder and intestines, a clear shift from the hepatic sink typically observed in full mAbs. This validated labeling method will be maintained throughout the proposed studies. A cold $^{19}$F-IFN-γ db compound will be prepared as reference standard for SEC quality control. Retention of affinity postconjugation is evaluated through binding affinity via surface plasmon resonance.

IFN-γ PET methods of the present invention measure active anti-tumor immunity, providing a predictive tool for non-invasive in situ tumor evaluation. This approach is highly specific to the tumor compared to total T cell imaging due to the fact that IFN-γ is secreted by CTLs within the tumor. Imaging CD3, on the other hand, targets the general T cell population that are not only localized in the tumor but also in other lymphoid tissues.

These results show that $^{89}$Zr-anti-IFN-γ labeled-antibody conjugate uptake can be indicative of response to therapy in both cancer vaccination and TAA-specific mAb models. These results further demonstrate that IFN-γ PET may be more sensitive for determining response to ITx when compared to peripheral immune evaluation. IFN-γ PET has the potential to serve as a universal non-invasive measurement of immune activity in situ for a variety of cancers with virtually any ITx modality with no need for knowledge of specific antigens or cumbersome ex vivo antigen recall assays. Additionally, the utility of IFN-γ PET allows for cancer immune monitoring, and examination of localized inflammatory conditions such as injury, infection, or autoimmune disease.

Collectively, these results suggest it may be optimal to detect activity of immune cell populations instead of mere presence. PET imaging of released, soluble IFNγ displayed higher sensitivity of active anti-tumor immunity detection versus total CD3 imaging. A major drawback to the use of general T cell surface markers for PET imaging is labeled-antibody conjugate uptake in normal secondary lymphoid tissues with dense T cell content, such as the spleen, thymus and lymph nodes, which may limit tumor detection. Importantly, these results indicate non-invasive in situ tumor evaluation by PET more clearly depicts responses to immunotherapy when compared to peripheral immune evaluation by ELISPOT. Unlike peripheral T cell assays, IFN-γ PET also does not require knowledge of specific tumor antigens or cumbersome ex vivo antigen recall assays to determine the extent of immunotherapy response. In addition, a mAb-based labeled-antibody conjugate may locally neutralize IFN-γ activity, which could benefit an anti-tumor response by reducing PD-L1 upregulation. Taken together, these results support the development of IFN-γ PET labeled-antibody conjugates for clinical evaluation of tumor immunotherapy.

Items

Item 1. A method for in vivo immunoimaging IFN-γ as a marker of active T cells in a subject, comprising: administering a labeled-antibody conjugate to a subject, wherein the labeled-antibody conjugate comprises: an antibody that specifically binds to IFN-γ, and a detection label conjugated to the antibody, wherein the detection label is a radionuclide tracer or fluorophore; and detecting the presence of the labeled-antibody conjugate in the subject in vivo by imaging.

Item 2. The method of item 1, wherein the subject has cancer.

Item 3. The method of item 2, wherein the subject received an immunotherapy prior to administering and detecting the presence of the labeled-antibody conjugate, and wherein the mechanism of action of the immunotherapy results in an increased number of tumor-infiltrating lymphocytes in the subject and/or an increased activation state of a tumor-infiltrating lymphocyte population in the subject; or wherein administering and detecting the presence of the labeled-antibody conjugate is performed prior to administration of a therapy to determine the state of active immunity in the subject.

Item 4. The method of item 3, wherein the immunotherapy is an immune checkpoint inhibitor, a cytokine, a vaccine, or an adoptive cell transfer therapy.

Item 5. The method of any one of the preceding items, wherein the subject is human and the antibody specifically binds to human IFN-γ.

Item 6. The method of any one of the preceding items, wherein the antibody is selected from a monoclonal antibody, an antibody fragment, or combination thereof.

Item 7. The method of item 6, wherein the antibody fragment is a Fab fragment.

Item 8. The method of item 6, wherein the antibody fragment is a diabody.

Item 9. The method of any one of the preceding items, wherein the radionuclide tracer is conjugated to the antibody or antibody fragment with a bifunctional chelator or linker.

Item 10. The method of item 9, wherein the bifunctional chelator comprises a chelator selected from N'-{5-[Acetyl(hydroxy)amino]pentyl}-N-[5-({4-[(5-aminopentyl)(hydroxy)amino]-4-oxobutanoyl}amino)pentyl]-N-hydroxysuccinamide (DFO), 1,4,7-triazacyclononane-N,N',N'-triacetic acid (NOTA), 1,4,7,10-tetraazacyclododecane-1,4,7,10-tetraacetic acid (DOTA), ethylenediaminetetraacetic acid (EDTA), 1,4,7,10-tetraazacyclododecane-1,4,7,10-tetraacetic acid (i.e., DOPA), diethylenetriaminepentaacetic acid (DTPA), 2,2'-(7-(1-carboxy-4-((2,5-dioxopyrrolidin-1-yl)oxy)-4-oxobutyl)-1,4,7-triazonane-1,4-diyl)diacetic acid (NODA), or a combination of any two or more thereof.

Item 11. The method of item 9 or item 10, wherein the bifunctional chelator is p-SCN-Bn-DFO.

Item 12. The method of any one of the preceding items, wherein the radionuclide tracer is selected from the group consisting of: $^{11}$C, $^{13}$N, $^{15}$O, $^{18}$F, $^{64}$Cu, $^{68}$Ga, $^{76}$Br, $^{82}$Rb, $^{86}$Y, $^{89}$Zr, $^{99m}$Tc, $^{111}$In, $^{124}$I, $^{131}$I, $^{186}$Re, $^{43}$K, $^{52}$Fe, $^{57}$Co, $^{67}$Cu, $^{67}$Ga, $^{77}$Br, $^{81}$Rb, $^{81m}$Kr, $^{87m}$Sr, $^{113m}$In, $^{123}$I, $^{125}$I, $^{127}$Cs, $^{129}$Cs, $^{132}$I, $^{197}$Hg, $^{203}$Pb, $^{206}$Bi, and combination of any two or more thereof.

Item 13. The method of item 12, wherein the radionuclide tracer is $^{89}$Zr or $^{18}$F.

Item 14. The method of any one of the preceding items, wherein the imaging comprises positron emission tomography (PET) imaging, single photon emission computed tomography (SPECT) imaging, or a both PET and SPECT.

Item 15. The method of item 14, wherein the imaging comprises PET.

Item 16. The method of any one of the preceding items, wherein the labeled-antibody conjugate further comprises a fluorophore.

Item 17. The method of any one of the preceding items, wherein specific binding of the labeled-antibody conjugate to IFN-γ indicates the presence of activated T cells and/or human cancer cells.

Item 18. The method of any one of the preceding items, wherein the presence of the labeled-antibody conjugate is detected in real time.

Item 19. A labeled-antibody conjugate comprising: an antibody that specifically binds to IFN-γ, and a detection label conjugated to the antibody, wherein the detection label is a radionuclide tracer.

Item 20. The labeled-antibody conjugate of item 19, wherein the antibody is isolated.

Item 21. The labeled-antibody conjugate of item 19 or item 20, wherein the antibody is selected from a monoclonal antibody, an antibody fragment, or combination thereof.

Item 22. The labeled-antibody conjugate of item 21, wherein the antibody fragment is a Fab fragment.

Item 23. The labeled-antibody conjugate of item 21, wherein the antibody fragment is a diabody.

Item 24. The labeled-antibody conjugate of any one of items 19 to 23, wherein the radionuclide tracer is conjugated to the antibody with a bifunctional chelator or linker.

Item 25. The labeled-antibody conjugate of item 24, wherein the bifunctional chelator comprises a chelator selected from N'-{5-[Acetyl(hydroxy)amino]pentyl}-N-[5-({4-[(5-aminopentyl)(hydroxy)amino]-4-oxobutanoyl}amino)pentyl]-N-hydroxysuccinamide (DFO), 1,4,7-triazacyclononane-N,N',N'-triacetic acid (NOTA), 1,4,7,10-tetraazacyclododecane-1,4,7,10-tetraacetic acid (DOTA), ethylenediaminetetraacetic acid (EDTA), 1,4,7,10-tetraazacyclododecane-1,4,7,10-tetraacetic acid (i.e., DOPA), diethylenetriaminepentaacetic acid (DTPA), 2,2'-(7-(1-carboxy-4-((2,5-dioxopyrrolidin-1-yl)oxy)-4-oxobutyl)-1,4,7-triazonane-1,4-diyl)diacetic acid (NODA), or a combination of any two or more thereof.

Item 26. The labeled-antibody conjugate of item 24 or item 25, wherein the bifunctional chelator is p-SCN-Bn-DFO or NOTA.

Item 27. The labeled-antibody conjugate of any one of items 19 to 26, wherein the radionuclide tracer is selected from $^{11}$C, $^{13}$N, $^{15}$O, $^{18}$F, $^{64}$Cu $^{68}$Ga, $^{76}$Br, $^{82}$Rb, $^{86}$Y, $^{89}$Zr, $^{99m}$Tc, $^{111}$In, $^{124}$I, $^{131}$I, $^{186}$Re, $^{43}$K, $^{52}$Fe, $^{57}$Co, $^{67}$Cu, $^{67}$Ga $^{77}$Br, $^{81}$Rb, $^{81m}$Kr, $^{87m}$Sr, $^{113m}$In, $^{123}$I, $^{125}$I, $^{127}$Cs, $^{129}$Cs, $^{132}$I, $^{197}$Hg, $^{203}$Pb, $^{206}$Bi, or a combination of any two or more thereof.

Item 28. The labeled-antibody conjugate of any one of items 19 to 27, wherein the radionuclide tracer is $^{89}$Zr or $^{18}$F.

Item 29. The labeled-antibody conjugate of any one of items 19 to 28, wherein the antibody specifically binds to human IFN-γ.

Sequences

```
Diabody heavy chain variable region (V_H)
                                         SEQ. ID NO: 11
LSQVQLKESGPGLVQPSQTLSLTCTVSGFSLDSYNVHWVRQPPGKGLEWMG

RMKYNGDTSYNSALKSRIRISRDTSKNQVFLKMNSLQTDDIGTYYCIRDWH

YGYPSPYFEFWGQGVIVIVTVSSAETTAPSVYPLAPGTALKSNSMVULGCL

VKGYFPEPVINTWNSGALSSGVHTFPAVLQSGINTLTSSVTVPSSTWPSQT

VICNVAIIPASSTKVDKKIVPRNCGGDCKPCICTGSEVSSVFIFPPKPKDV

LTITLTPKVTCVVVDISQDDPEVHFSWFVDDVEVHTAQTRITEEQFNSTFR

SVSELPILHQDWLNGRTFRCKVTSAAFPSIRIEKTISKPEGRTQVPHVYTM

SPTKEEMLQNEVSITCMVKGFYPPDIYVEWQMNGQPQENYKNTPPTMDTDG

SYFLYSKLNVKKEKWQQGNTFTCSVLHEGLHNHHTEKSLSHSPGK

Diabody light chain variable region (V_L)
                                         SEQ ID NO: 12
DVQMTQSPSYLAASPGESVSISCKASKNINTYLAWYQEKPGKTNKLLIYSG

STLQSGTPSRFSGSGSGTDFTLTIRSLEPEDFAVYYCQQHNEYPLTFGSGT

KLEVKRADAAPTVSITPPSTEQLATGGASVVCLMNINFYPRDISVQWKIDG

TERRDGVLDSVTDQDSKDSTYSMSSTLSLTKADYESHNLYTCEVVHKTSSS

PVVKSPNWNEC

Exemplary linker
                                         (SEQ ID NO: 13)
SGGGGS.

scFv SEQ ID NO:14 which can be included in an
anti-11-7N-g diabody
LSQVQLKESGPGLVQPSQTLSLTCTVSGFSLDSYNVHWVRQPPGKGLEWMG

RMKYNGDTSYNSALKSRLRISRDTSKNQVFLKMNSLQTDDTGTYYCTRDWH

YGYPSPYFEFWGQGVNIVTVSSAETTAPSVYPLAPGTALKSNSMVTLGGIN

KGYFPEPVTVTWNSGALSSGVHTFPAVLQSGLYTLTSSVTVPSSTWPSQTV

TCNVAHPASSTKVDKKIVPRNCGGDCKPCICTGSEVSSVFIFPPKPKDVLT

ITLTPKVTCVVVDISQDDPEVHFSWFVDDVEVHTAQTRPPEEQFNSTFRSV

SELPILBQDWLNGRTFRCKVTSAAFPSPIEKTIISKPEGRTQVPHVYTMSP

TKEEMLQNEVSITCMVKGFYPPDIYVEWQMNGQPQENYKNTPPTMDTDGSY

FLYSKLNVKKEKWQQGNTFTCSVLHEGLHNHHTEKSLSHSPGKSGGGGSDV

QMTQSPSYLAASPGESVSISCKASKNINTYLAWYQEKPGKTNKLLIYSGST

LQSGTPSRFSGSGSGTDFTLTIRSLEPEDFAVYYCQQHNEYPLTFGSGTKI

EVKRADAAPTVSIFPPSTEQLATGGASVVCLMNNFYPRDISVQWKIDGTER

RDGVLDSVTDQDSKDSTYSMSSTLSLTKADYESHNLYTCEVVHKTSSSPVV

KSENRNEC scfv SEQ :ID NO: 15 which can be included in an
anti-IFN-g diabody
DVQMTQSPSYLAASPGESVSISCKASKNINTYLAWYQEKPGKTNKLUYSGS

TLQSGTPSRFSGSGSGTDFILTIRSLEPEDFAVYYCQQHNEYPLITGSGIK

LEVKRADAAPTVSIFPPSTEQLATGGASVVCLMNNFYPRDISVQWKIDGIE

RRIXWLDSVTDQDSKDSTYSMSSTLSLTKADYESHNLYTCEVVHKTSSSPV

VKSFNRINECSGGGGSLSQVQLKESGPGLVQPSQTLSLTCTVSGFSLDSYN

VHWVRQPPGKGLEWMGRMKYNGDTSYNSMKSRLRISRDTSKNQWLKNINSL

QTDDTGTYYCTRDWHYGYPSPYFEFWGQGVMVTVSSAETTAPSVYPLAPGT

ALKSNSMVTLGCLVKGYFPEPVTVTWNSGALSSGVHTFPAVLQSGLYTLTS

SVTVPSSTWPSQTVTCNVAHPASSTKVDKKIVPRNCGGDCKPCICTGSEVS

SVFIFPPKPKDVLTITLTPKVICVVVDISQDDPEWIFSWFVDDVEVHTAQT

RPPEEQFNSTFRSVSELPTILHQDWLNGRTFRCKVTSAAFPSPIEKTISKP

EGRTQVPHVYTMSPTKEENILQNEVSITCMVKGFITPDIYVEWQMNGQPQE

NYKNTPPTNIDTDGSNTLYSKLNVKKEKWQQGNTFTCSVLHEGLHNHHTEK

SLSHSPGK
```

All documents cited are incorporated herein by reference; the citation of any document is not to be construed as an admission that it is prior art with respect to the present disclosure.

It is to be further understood that where descriptions of various embodiments use the term "comprising," and/or "including" those skilled in the art would understand that in some specific instances, an embodiment can be alternatively described using language "consisting essentially of" or "consisting of."

While particular embodiments of the present disclosure have been illustrated and described, it would be obvious to one skilled in the art that various other changes and modifications can be made without departing from the spirit and scope of the disclosure. It is therefore intended to cover in the appended claims all such changes and modifications that are within the scope of this disclosure.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Unless otherwise defined, all technical and scientific terms used herein have the same meaning as commonly understood by one of ordinary skill in the art to which the claimed subject matter belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

The invention claimed is:

1. A method for in vivo immunoimaging interferon gamma (IFN-γ) as a marker of active T cells in a subject with cancer, comprising:
   administering a labeled-antibody conjugate to a subject, wherein the labeled-antibody conjugate comprises:
   an antibody that specifically binds to IFN-γ, and
   a detection label conjugated to the antibody, wherein the detection label is a radionuclide tracer selected from $^{11}$C, $^{13}$N, $^{15}$O, $^{18}$F, $^{44}$Sc, $^{45}$Ti, $^{52}$Mn, $^{64}$Cu, $^{68}$Ga, $^{76}$Br, $^{82}$Rb, $^{86}$Y, $^{89}$Zr, $^{111}$In, $^{124}$I, $^{43}$K, $^{52}$Fe, $^{57}$Co, $^{67}$Cu, $^{67}$Ga, $^{77}$Br, $^{81}$Rb, $^{81m}$Kr, $^{87m}$Sr, $^{113m}$In, $^{123}$I, $^{127}$Cs, $^{129}$Cs, $^{132}$I, $^{197}$Hg, $^{203}$Pb, $^{206}$Bi, or a combination of any two or more thereof; and
   detecting the presence of the labeled-antibody conjugate in the subject in vivo by imaging, wherein specific binding of the labeled-antibody conjugate to IFN-γ indicates the presence of activated T cells.

2. The method of claim 1, wherein the subject received an immunotherapy prior to administering and detecting the presence of the labeled-antibody conjugate, and wherein the mechanism of action of the immunotherapy results in an increased number of tumor-infiltrating lymphocytes in the subject and/or an increased activation state of a tumor-infiltrating lymphocyte population in the subject; or wherein administering and detecting the presence of the labeled-antibody conjugate is performed prior to administration of a therapy to determine the state of active immunity in the subject.

3. The method of claim 2, wherein the subject received an immunotherapy prior to administering and detecting the presence of the labeled-antibody conjugate, and wherein the mechanism of action of the immunotherapy results in an increased number of tumor-infiltrating lymphocytes in the subject and/or an increased activation state of a tumor-infiltrating lymphocyte population in the subject; and wherein the immunotherapy is an immune checkpoint inhibitor, a cytokine, a vaccine, or an adoptive cell transfer therapy.

4. The method of claim 1, wherein the subject is human and the antibody specifically binds to human IFN-γ.

5. The method of claim 1, wherein the antibody is selected from a monoclonal antibody, an antibody fragment, or combination thereof.

6. The method of claim 5, wherein the antibody is an antibody fragment, and wherein the antibody fragment is a Fab fragment or a diabody.

7. The method of claim 1, wherein the imaging comprises positron emission tomography (PET) imaging, single photon emission computed tomography (SPECT) imaging, or a both PET and SPECT.

8. The method of claim 1, wherein the presence of the labeled-antibody conjugate is detected in real time.

9. The method of claim 1, wherein the radionuclide tracer is conjugated to the antibody with a bifunctional chelator or linker.

10. The method of claim 9, wherein the radionuclide tracer is conjugated to the antibody with a bifunctional chelator, and wherein the bifunctional chelator comprises a chelator selected from N'-{5-[Acetyl(hydroxy)amino]pentyl}-N-[5-({4-[(5-aminopentyl)(hydroxy)amino]-4-oxobutanoyl}amino)pentyl]-N-hydroxysuccinamide (DFO), 1,4,7-triazacyclononane-N,N',N'-triacetic acid (NOTA), 1,4,7,10-tetraazacyclododecane-1,4,7,10-tetraacetic acid (DOTA), ethylenediaminetetraacetic acid (EDTA), 1,4,7,10-tetraazacyclododecane-1,4,7,10-tetraacetic acid (DOPA), diethylenetriaminepentaacetic acid (DTPA), 2,2'-(7-(1-carboxy-4-((2,5-dioxopyrrolidin-1-yl)oxy)-4-oxobutyl)-1,4,7-triazonane-1,4-diyl)diacetic acid (NODA), or a combination of any two or more thereof.

11. The method of claim 9, wherein the radionuclide tracer is conjugated to the antibody with a bifunctional chelator, and wherein the bifunctional chelator is p-SCN-Bn-DFO or NOTA.

* * * * *

SEQUENCE LISTING

```
<160> NUMBER OF SEQ ID NOS: 15

<210> SEQ ID NO 1
<211> LENGTH: 20
<212> TYPE: DNA
<213> ORGANISM: Artificial Sequence
<220> FEATURE:
<223> OTHER INFORMATION: CD3 forward primer

<400> SEQUENCE: 1
cactctgggc ttgctgatgg                                                   20

<210> SEQ ID NO 2
<211> LENGTH: 22
<212> TYPE: DNA
<213> ORGANISM: Artificial Sequence
<220> FEATURE:
<223> OTHER INFORMATION: CD3 reverse primer

<400> SEQUENCE: 2
tcatagtctg ggttggaaca gg                                                22

<210> SEQ ID NO 3
<211> LENGTH: 23
<212> TYPE: DNA
<213> ORGANISM: Artificial Sequence
<220> FEATURE:
<223> OTHER INFORMATION: CD8 forward primer

<400> SEQUENCE: 3
gctggtagtc tgcatcctgc ttc                                               23

<210> SEQ ID NO 4
<211> LENGTH: 25
<212> TYPE: DNA
<213> ORGANISM: Artificial Sequence
<220> FEATURE:
<223> OTHER INFORMATION: CD8 reverse primer

<400> SEQUENCE: 4
ttgctagcag gctatcagtg ttgtg                                             25

<210> SEQ ID NO 5
<211> LENGTH: 20
<212> TYPE: DNA
<213> ORGANISM: Artificial Sequence
<220> FEATURE:
<223> OTHER INFORMATION: IFN- gamma forward primer

<400> SEQUENCE: 5
gagctcattg aatgcttggc                                                   20
```

```
<210> SEQ ID NO 6
<211> LENGTH: 20
<212> TYPE: DNA
<213> ORGANISM: Artificial Sequence
<220> FEATURE:
<223> OTHER INFORMATION: IFN- gamma reverse primer

<400> SEQUENCE: 6
gcgtcattga atcacacctg                                              20

<210> SEQ ID NO 7
<211> LENGTH: 20
<212> TYPE: DNA
<213> ORGANISM: Artificial Sequence
<220> FEATURE:
<223> OTHER INFORMATION: PD-1 forward primer

<400> SEQUENCE: 7
cgtccctcag tcaagaggag                                              20

<210> SEQ ID NO 8
<211> LENGTH: 20
<212> TYPE: DNA
<213> ORGANISM: Artificial Sequence
<220> FEATURE:
<223> OTHER INFORMATION: PD-1 reverse primer

<400> SEQUENCE: 8
gtccctagaa gtgcccaaca                                              20

<210> SEQ ID NO 9
<211> LENGTH: 21
<212> TYPE: DNA
<213> ORGANISM: Artificial Sequence
<220> FEATURE:
<223> OTHER INFORMATION: GAPDH forward primer

<400> SEQUENCE: 9
aagctcactg gcatggcctt c                                            21

<210> SEQ ID NO 10
<211> LENGTH: 23
<212> TYPE: DNA
<213> ORGANISM: Artificial Sequence
<220> FEATURE:
<223> OTHER INFORMATION: GAPDH reverse primer

<400> SEQUENCE: 10
tgcttcacca ccttcttgat gtc                                          23

<210> SEQ ID NO 11
<211> LENGTH: 449
<212> TYPE: PRT
<213> ORGANISM: Artificial Sequence
<220> FEATURE:
<223> OTHER INFORMATION: Diabody heavy chain variable region

<400> SEQUENCE: 11

Leu Ser Gln Val Gln Leu Lys Glu Ser Gly Pro Gly Leu Val Gln Pro
1               5                   10                  15

Ser Gln Thr Leu Ser Leu Thr Cys Thr Val Ser Gly Phe Ser Leu Asp
            20                  25                  30

Ser Tyr Asn Val His Trp Val Arg Gln Pro Pro Gly Lys Gly Leu Glu
        35                  40                  45

Trp Met Gly Arg Met Lys Tyr Asn Gly Asp Thr Ser Tyr Asn Ser Ala
```

```
            50                  55                  60
Leu Lys Ser Arg Leu Arg Ile Ser Arg Asp Thr Ser Lys Asn Gln Val
 65                  70                  75                  80

Phe Leu Lys Met Asn Ser Leu Gln Thr Asp Thr Gly Thr Tyr Tyr
                 85                  90                  95

Cys Thr Arg Asp Trp His Tyr Gly Tyr Pro Ser Pro Tyr Phe Glu Phe
                100                 105                 110

Trp Gly Gln Gly Val Met Val Thr Val Ser Ser Ala Glu Thr Thr Ala
                115                 120                 125

Pro Ser Val Tyr Pro Leu Ala Pro Gly Thr Ala Leu Lys Ser Asn Ser
                130                 135                 140

Met Val Thr Leu Gly Cys Leu Val Lys Gly Tyr Phe Pro Glu Pro Val
145                 150                 155                 160

Thr Val Thr Trp Asn Ser Gly Ala Leu Ser Ser Gly Val His Thr Phe
                165                 170                 175

Pro Ala Val Leu Gln Ser Gly Leu Tyr Thr Leu Thr Ser Ser Val Thr
                180                 185                 190

Val Pro Ser Ser Thr Trp Pro Ser Gln Thr Val Thr Cys Asn Val Ala
                195                 200                 205

His Pro Ala Ser Ser Thr Lys Val Asp Lys Lys Ile Val Pro Arg Asn
    210                 215                 220

Cys Gly Gly Asp Cys Lys Pro Cys Ile Cys Thr Gly Ser Glu Val Ser
225                 230                 235                 240

Ser Val Phe Ile Phe Pro Pro Lys Pro Lys Asp Val Leu Thr Ile Thr
                245                 250                 255

Leu Thr Pro Lys Val Thr Cys Val Val Val Asp Ile Ser Gln Asp Asp
                260                 265                 270

Pro Glu Val His Phe Ser Trp Phe Val Asp Asp Val Glu Val His Thr
                275                 280                 285

Ala Gln Thr Arg Pro Pro Glu Glu Gln Phe Asn Ser Thr Phe Arg Ser
    290                 295                 300

Val Ser Glu Leu Pro Ile Leu His Gln Asp Trp Leu Asn Gly Arg Thr
305                 310                 315                 320

Phe Arg Cys Lys Val Thr Ser Ala Ala Phe Pro Ser Pro Ile Glu Lys
                325                 330                 335

Thr Ile Ser Lys Pro Glu Gly Arg Thr Gln Val Pro His Val Tyr Thr
                340                 345                 350

Met Ser Pro Thr Lys Glu Glu Met Leu Gln Asn Glu Val Ser Ile Thr
                355                 360                 365

Cys Met Val Lys Gly Phe Tyr Pro Pro Asp Ile Tyr Val Glu Trp Gln
    370                 375                 380

Met Asn Gly Gln Pro Gln Glu Asn Tyr Lys Asn Thr Pro Pro Thr Met
385                 390                 395                 400

Asp Thr Asp Gly Ser Tyr Phe Leu Tyr Ser Lys Leu Asn Val Lys Lys
                405                 410                 415

Glu Lys Trp Gln Gln Gly Asn Thr Phe Thr Cys Ser Val Leu His Glu
                420                 425                 430

Gly Leu His Asn His His Thr Glu Lys Ser Leu Ser His Ser Pro Gly
    435                 440                 445

Lys

<210> SEQ ID NO 12
<211> LENGTH: 214
```

```
<212> TYPE: PRT
<213> ORGANISM: Artificial Sequence
<220> FEATURE:
<223> OTHER INFORMATION: Diabody light chain variable region

<400> SEQUENCE: 12

Asp Val Gln Met Thr Gln Ser Pro Ser Tyr Leu Ala Ala Ser Pro Gly
1               5                   10                  15

Glu Ser Val Ser Ile Ser Cys Lys Ala Ser Lys Asn Ile Asn Thr Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Thr Pro Ser Arg Phe Ser Gly
50                  55                  60

Ser Gly Ser Gly Thr Asp Phe Thr Leu Thr Ile Arg Ser Leu Glu Pro
65                  70                  75                  80

Glu Asp Phe Ala Val Tyr Tyr Cys Gln Gln His Asn Glu Tyr Pro Leu
                85                  90                  95

Thr Phe Gly Ser Gly Thr Lys Leu Glu Val Lys Arg Ala Asp Ala Ala
            100                 105                 110

Pro Thr Val Ser Ile Phe Pro Pro Ser Thr Glu Gln Leu Ala Thr Gly
        115                 120                 125

Gly Ala Ser Val Val Cys Leu Met Asn Asn Phe Tyr Pro Arg Asp Ile
130                 135                 140

Ser Val Gln Trp Lys Ile Asp Gly Thr Glu Arg Arg Asp Gly Val Leu
145                 150                 155                 160

Asp Ser Val Thr Asp Gln Asp Ser Lys Asp Ser Thr Tyr Ser Met Ser
                165                 170                 175

Ser Thr Leu Ser Leu Thr Lys Ala Asp Tyr Glu Ser His Asn Leu Tyr
            180                 185                 190

Thr Cys Glu Val Val His Lys Thr Ser Ser Pro Val Val Lys Ser
        195                 200                 205

Phe Asn Arg Asn Glu Cys
    210

<210> SEQ ID NO 13
<211> LENGTH: 6
<212> TYPE: PRT
<213> ORGANISM: Artificial Sequence
<220> FEATURE:
<223> OTHER INFORMATION: linker

<400> SEQUENCE: 13

Ser Gly Gly Gly Gly Ser
1               5

<210> SEQ ID NO 14
<211> LENGTH: 669
<212> TYPE: PRT
<213> ORGANISM: Artificial Sequence
<220> FEATURE:
<223> OTHER INFORMATION: Diabody single chain variable fragment scFv

<400> SEQUENCE: 14

Leu Ser Gln Val Gln Leu Lys Glu Ser Gly Pro Gly Leu Val Gln Pro
1               5                   10                  15

Ser Gln Thr Leu Ser Leu Thr Cys Thr Val Ser Gly Phe Ser Leu Asp
            20                  25                  30

Ser Tyr Asn Val His Trp Val Arg Gln Pro Pro Gly Lys Gly Leu Glu
```

-continued

```
                35                  40                  45
Trp Met Gly Arg Met Lys Tyr Asn Gly Asp Thr Ser Tyr Asn Ser Ala
 50                  55                  60

Leu Lys Ser Arg Leu Arg Ile Ser Arg Asp Thr Ser Lys Asn Gln Val
 65                  70                  75                  80

Phe Leu Lys Met Asn Ser Leu Gln Thr Asp Thr Gly Thr Tyr Tyr
                     85                  90                  95

Cys Thr Arg Asp Trp His Tyr Gly Tyr Pro Ser Pro Tyr Phe Glu Phe
                100                 105                 110

Trp Gly Gln Gly Val Met Val Thr Val Ser Ser Ala Glu Thr Thr Ala
                115                 120                 125

Pro Ser Val Tyr Pro Leu Ala Pro Gly Thr Ala Leu Lys Ser Asn Ser
130                 135                 140

Met Val Thr Leu Gly Cys Leu Val Lys Gly Tyr Phe Pro Glu Pro Val
145                 150                 155                 160

Thr Val Thr Trp Asn Ser Gly Ala Leu Ser Ser Gly Val His Thr Phe
                165                 170                 175

Pro Ala Val Leu Gln Ser Gly Leu Tyr Thr Leu Thr Ser Ser Val Thr
                180                 185                 190

Val Pro Ser Ser Thr Trp Pro Ser Gln Thr Val Thr Cys Asn Val Ala
                195                 200                 205

His Pro Ala Ser Ser Thr Lys Val Asp Lys Ile Val Pro Arg Asn
210                 215                 220

Cys Gly Gly Asp Cys Lys Pro Cys Ile Cys Thr Gly Ser Glu Val Ser
225                 230                 235                 240

Ser Val Phe Ile Phe Pro Pro Lys Pro Lys Asp Val Leu Thr Ile Thr
                245                 250                 255

Leu Thr Pro Lys Val Thr Cys Val Val Asp Ile Ser Gln Asp Asp
                260                 265                 270

Pro Glu Val His Phe Ser Trp Phe Val Asp Asp Val Glu Val His Thr
                275                 280                 285

Ala Gln Thr Arg Pro Pro Glu Glu Gln Phe Asn Ser Thr Phe Arg Ser
290                 295                 300

Val Ser Glu Leu Pro Ile Leu His Gln Asp Trp Leu Asn Gly Arg Thr
305                 310                 315                 320

Phe Arg Cys Lys Val Thr Ser Ala Ala Phe Pro Ser Pro Ile Glu Lys
                325                 330                 335

Thr Ile Ser Lys Pro Glu Gly Arg Thr Gln Val Pro His Val Tyr Thr
                340                 345                 350

Met Ser Pro Thr Lys Glu Glu Met Leu Gln Asn Glu Val Ser Ile Thr
                355                 360                 365

Cys Met Val Lys Gly Phe Tyr Pro Pro Asp Ile Tyr Val Glu Trp Gln
                370                 375                 380

Met Asn Gly Gln Pro Gln Glu Asn Tyr Lys Asn Thr Pro Pro Thr Met
385                 390                 395                 400

Asp Thr Asp Gly Ser Tyr Phe Leu Tyr Ser Lys Leu Asn Val Lys Lys
                405                 410                 415

Glu Lys Trp Gln Gln Gly Asn Thr Phe Thr Cys Ser Val Leu His Glu
                420                 425                 430

Gly Leu His Asn His His Thr Glu Lys Ser Leu Ser His Ser Pro Gly
                435                 440                 445

Lys Ser Gly Gly Gly Gly Ser Asp Val Gln Met Thr Gln Ser Pro Ser
450                 455                 460
```

Tyr Leu Ala Ala Ser Pro Gly Glu Ser Val Ser Ile Ser Cys Lys Ala
465                 470                 475                 480

Ser Lys Asn Ile Asn Thr Tyr Leu Ala Trp Tyr Gln Glu Lys Pro Gly
                485                 490                 495

Lys Thr Asn Lys Leu Leu Ile Tyr Ser Gly Ser Thr Leu Gln Ser Gly
            500                 505                 510

Thr Pro Ser Arg Phe Ser Gly Ser Gly Ser Gly Thr Asp Phe Thr Leu
            515                 520                 525

Thr Ile Arg Ser Leu Glu Pro Glu Asp Phe Ala Val Tyr Tyr Cys Gln
530                 535                 540

Gln His Asn Glu Tyr Pro Leu Thr Phe Gly Ser Gly Thr Lys Leu Glu
545                 550                 555                 560

Val Lys Arg Ala Asp Ala Ala Pro Thr Val Ser Ile Phe Pro Pro Ser
                565                 570                 575

Thr Glu Gln Leu Ala Thr Gly Gly Ala Ser Val Val Cys Leu Met Asn
            580                 585                 590

Asn Phe Tyr Pro Arg Asp Ile Ser Val Gln Trp Lys Ile Asp Gly Thr
            595                 600                 605

Glu Arg Arg Asp Gly Val Leu Asp Ser Val Thr Asp Gln Asp Ser Lys
610                 615                 620

Asp Ser Thr Tyr Ser Met Ser Ser Thr Leu Ser Leu Thr Lys Ala Asp
625                 630                 635                 640

Tyr Glu Ser His Asn Leu Tyr Thr Cys Glu Val Val His Lys Thr Ser
                645                 650                 655

Ser Ser Pro Val Val Lys Ser Phe Asn Arg Asn Glu Cys
            660                 665

<210> SEQ ID NO 15
<211> LENGTH: 669
<212> TYPE: PRT
<213> ORGANISM: Artificial Sequence
<220> FEATURE:
<223> OTHER INFORMATION: Diabody single chain variable fragment scFv

<400> SEQUENCE: 15

Asp Val Gln Met Thr Gln Ser Pro Ser Tyr Leu Ala Ala Ser Pro Gly
1               5                   10                  15

Glu Ser Val Ser Ile Ser Cys Lys Ala Ser Lys Asn Ile Asn Thr Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Thr Pro Ser Arg Phe Ser Gly
50                  55                  60

Ser Gly Ser Gly Thr Asp Phe Thr Leu Thr Ile Arg Ser Leu Glu Pro
65                  70                  75                  80

Glu Asp Phe Ala Val Tyr Tyr Cys Gln Gln His Asn Glu Tyr Pro Leu
                85                  90                  95

Thr Phe Gly Ser Gly Thr Lys Leu Glu Val Lys Arg Ala Asp Ala Ala
            100                 105                 110

Pro Thr Val Ser Ile Phe Pro Pro Ser Thr Glu Gln Leu Ala Thr Gly
        115                 120                 125

Gly Ala Ser Val Val Cys Leu Met Asn Asn Phe Tyr Pro Arg Asp Ile
    130                 135                 140

Ser Val Gln Trp Lys Ile Asp Gly Thr Glu Arg Arg Asp Gly Val Leu
145                 150                 155                 160

```
Asp Ser Val Thr Asp Gln Asp Ser Lys Asp Ser Thr Tyr Ser Met Ser
                165                 170                 175

Ser Thr Leu Ser Leu Thr Lys Ala Asp Tyr Glu Ser His Asn Leu Tyr
            180                 185                 190

Thr Cys Glu Val Val His Lys Thr Ser Ser Pro Val Val Lys Ser
        195                 200                 205

Phe Asn Arg Asn Glu Cys Ser Gly Gly Gly Ser Leu Ser Gln Val
    210                 215                 220

Gln Leu Lys Glu Ser Gly Pro Gly Leu Val Gln Pro Ser Gln Thr Leu
225                 230                 235                 240

Ser Leu Thr Cys Thr Val Ser Gly Phe Ser Leu Asp Ser Tyr Asn Val
            245                 250                 255

His Trp Val Arg Gln Pro Pro Gly Lys Gly Leu Glu Trp Met Gly Arg
        260                 265                 270

Met Lys Tyr Asn Gly Asp Thr Ser Tyr Asn Ser Ala Leu Lys Ser Arg
    275                 280                 285

Leu Arg Ile Ser Arg Asp Thr Ser Lys Asn Gln Val Phe Leu Lys Met
290                 295                 300

Asn Ser Leu Gln Thr Asp Asp Thr Gly Thr Tyr Tyr Cys Thr Arg Asp
305                 310                 315                 320

Trp His Tyr Gly Tyr Pro Ser Pro Tyr Phe Glu Phe Trp Gly Gln Gly
                325                 330                 335

Val Met Val Thr Val Ser Ser Ala Glu Thr Thr Ala Pro Ser Val Tyr
            340                 345                 350

Pro Leu Ala Pro Gly Thr Ala Leu Lys Ser Asn Ser Met Val Thr Leu
        355                 360                 365

Gly Cys Leu Val Lys Gly Tyr Phe Pro Glu Pro Val Thr Val Thr Trp
370                 375                 380

Asn Ser Gly Ala Leu Ser Ser Gly Val His Thr Phe Pro Ala Val Leu
385                 390                 395                 400

Gln Ser Gly Leu Tyr Thr Leu Thr Ser Ser Val Thr Val Pro Ser Ser
                405                 410                 415

Thr Trp Pro Ser Gln Thr Val Thr Cys Asn Val Ala His Pro Ala Ser
            420                 425                 430

Ser Thr Lys Val Asp Lys Lys Ile Val Pro Arg Asn Cys Gly Gly Asp
        435                 440                 445

Cys Lys Pro Cys Ile Cys Thr Gly Ser Glu Val Ser Ser Val Phe Ile
450                 455                 460

Phe Pro Pro Lys Pro Lys Asp Val Leu Thr Ile Thr Leu Thr Pro Lys
465                 470                 475                 480

Val Thr Cys Val Val Val Asp Ile Ser Gln Asp Asp Pro Glu Val His
                485                 490                 495

Phe Ser Trp Phe Val Asp Asp Val Glu Val His Thr Ala Gln Thr Arg
            500                 505                 510

Pro Pro Glu Glu Gln Phe Asn Ser Thr Phe Arg Ser Val Ser Glu Leu
        515                 520                 525

Pro Ile Leu His Gln Asp Trp Leu Asn Gly Arg Thr Phe Arg Cys Lys
530                 535                 540

Val Thr Ser Ala Ala Phe Pro Ser Pro Ile Glu Lys Thr Ile Ser Lys
545                 550                 555                 560

Pro Glu Gly Arg Thr Gln Val Pro His Val Tyr Thr Met Ser Pro Thr
                565                 570                 575
```

-continued

```
Lys Glu Glu Met Leu Gln Asn Glu Val Ser Ile Thr Cys Met Val Lys
            580                 585                 590

Gly Phe Tyr Pro Pro Asp Ile Tyr Val Glu Trp Gln Met Asn Gly Gln
        595                 600                 605

Pro Gln Glu Asn Tyr Lys Asn Thr Pro Pro Thr Met Asp Thr Asp Gly
    610                 615                 620

Ser Tyr Phe Leu Tyr Ser Lys Leu Asn Val Lys Lys Glu Lys Trp Gln
625                 630                 635                 640

Gln Gly Asn Thr Phe Thr Cys Ser Val Leu His Glu Gly Leu His Asn
                645                 650                 655

His His Thr Glu Lys Ser Leu Ser His Ser Pro Gly Lys
                660                 665
```